(12) United States Patent
Welch et al.

(10) Patent No.: US 6,460,012 B1
(45) Date of Patent: Oct. 1, 2002

(54) NONLINEAR STRUCTURAL CRACK GROWTH MONITORING

(75) Inventors: Donald E. Welch, Oak Ridge; Lee M. Hively, Philadelphia; Ray F. Holdaway, Clinton, all of TN (US)

(73) Assignee: U.T. Battelle, LLC,, Oak Ridge, TN (US)

( * ) Notice: Subject to any disclaimer, the term of this patent is extended or adjusted under 35 U.S.C. 154(b) by 0 days.

(21) Appl. No.: 09/397,185

(22) Filed: Sep. 16, 1999

(51) Int. Cl.$^7$ ................................................. G01L 1/00
(52) U.S. Cl. ........................... 702/182; 702/35; 702/42; 702/43; 702/183; 73/760; 73/799
(58) Field of Search ................................ 702/182, 183, 702/35, 42, 43; 73/760, 788, 799, 786, 583, 802, 602

(56) References Cited

U.S. PATENT DOCUMENTS

| | | | |
|---|---|---|---|
| 4,179,940 A | * 12/1979 | Oertle et al. | 73/808 |
| 4,191,470 A | 3/1980 | Butter | |
| 4,304,135 A | * 12/1981 | Peterson et al. | 73/799 |
| 4,421,979 A | 12/1983 | Asawa et al. | |
| 4,770,492 A | 9/1988 | Levin et al. | |
| 5,479,824 A | * 1/1996 | Torres | 702/43 |
| 5,626,145 A | 5/1997 | Clapp et al. | |
| 5,728,943 A | * 3/1998 | Colter, Jr. et al. | 73/799 |
| 5,743,860 A | 4/1998 | Hively et al. | |
| 5,815,413 A | 9/1998 | Hively et al. | |
| 5,816,530 A | * 10/1998 | Grube | 702/35 |
| 5,857,978 A | 1/1999 | Hively et al. | |

OTHER PUBLICATIONS

Dieter, George E., *Mechanical Metallurgy*, 2d Ed. McGraw–Hill Book Co., New York (19__), pp. 453, 521–522.

Knott, J.F., *Fundamentals of Fracture Mechanics*, Butterworths, London UK (19__), pp. 260–264.

* cited by examiner

Primary Examiner—John S. Hilten
Assistant Examiner—Hien Vo
(74) Attorney, Agent, or Firm—Oscar A. Towler, III; Nexsen Pruet Jacobs & Pollard, LLC

(57) ABSTRACT

A method and apparatus are provided for the detection, through nonlinear manipulation of data, of an indicator of imminent failure due to crack growth in structural elements. The method is a process of determining energy consumption due to crack growth and correlating the energy consumption with physical phenomena indicative of a failure event. The apparatus includes sensors for sensing physical data factors, processors or the like for computing a relationship between the physical data factors and phenomena indicative of the failure event, and apparatus for providing notification of the characteristics and extent of such phenomena.

13 Claims, 71 Drawing Sheets

|  | Specimen | | | |
| --- | --- | --- | --- | --- |
|  | P36-O-45 | P36-O-46 | P36-O-47 | P36-O-48 |
| Cross-sectional area, in.$^2$ | 0.0996 | 0.0993 | 0.1003 | 0.0894 |
| Nominal peak tensile load, lb | 1,480 | 1,478 | 1,190 | 1,188 |
| Nominal peak tensile stress, psi | 14,860 | 14,885 | 11,865 | 13,290 |
| Nominal minimum tensile load, lb | 140 | 147 | 121 | 116 |
| Nominal minimum tensile stress, psi | 1,406 | 1,480 | 1,206 | 1,298 |
| Cycles to failure | 3,686 | 2,417 | 24,506 | 5,763 |

Fig. 4

|  | Specimen | | | |
|---|---|---|---|---|
|  | P36-O-45 | P36-O-46 | P36-O-47 | P36-O-48 |
| Cycles for slope or curvature > UCL | 2,888 | 1,896 | 19,082 | 5,706 |
| Indication based on slope or curvature | Curvature | Curvature | Curvature | Slope |
| Cycles to failure | 3,686 | 2,417 | 24,506 | 5,763 |
| Fatigue life remaining after indication, % | 21.65 | 21.56 | 22.13 | 0.99 |

Fig. 10

|  | Specimen | | | | | | | | | |
| --- | --- | --- | --- | --- | --- | --- | --- | --- | --- | --- |
|  | TM-1 | TM-2 | TM-3 | TM-4 | TM-5 | TM-6 | TM-7 | TM-8 | TM-9 | TM-10 |
| Nominal peak tensile load, lb | 2,340 | 2,340 | 2,340 | 2,340 | 2,340 | 2,340 | 2,340 | 2,760 | 3,000 | 3,120 |
| Nominal peak tensile stress, psi | 52,000 | 52,000 | 52,000 | 52,000 | 52,000 | 52,000 | 52,000 | 61,340 | 66,629 | 71,917 |
| Nominal minimum tensile load, lb | 234 | 234 | 234 | 234 | 234 | 234 | 234 | 276 | 300 | 312 |
| Nominal minimum tensile stress, psi | 5,200 | 5,200 | 5,200 | 5,200 | 5,200 | 5,200 | 5,200 | 6,134 | 6,663 | 7,192 |
| Cycles to failure | 33,133 | 41,955 | 25,404 | 43,750 | 44,727 | 39,969 | 34,682 | 17,142 | 12,362 | 6,938 |
| Cycles of fatigue life remaining after indication | 538 | 738 | 419 | 357 | 578 | 972 | 1,656 | 578 | 213 | 122 |
| Fatigue life remaining after indication, % | 1.62 | 1.76 | 1.65 | 0.82 | 1.29 | 2.43 | 4.78 | 3.37 | 1.72 | 1.76 |

𝔉𝔦𝔤. 13

|  | Specimen | | | | | | | | | |
|---|---|---|---|---|---|---|---|---|---|---|
|  | TM-1 | TM-2 | TM-3 | TM-4 | TM-5 | TM-6 | TM-7 | TM-8 | TM-9 | TM-10 |
| Indication based on: | Curv. | Slope | Slope | Slope | Slope | Slope | Curv. | Slope | Slope | Curv. |
| Cycles for indication > UCL or < LCL | 32,595 | 41,217 | 24,985 | 43,393 | 43,949 | 38,997 | 33,026 | 16,564 | 12,149 | 6,816 |
| Cycles to failure | 33,133 | 41,955 | 25,404 | 43,750 | 44,727 | 39,969 | 34,682 | 17,142 | 12,362 | 6,938 |
| Cycles of life remaining after indication | 538 | 738 | 419 | 357 | 578 | 972 | 1,656 | 578 | 213 | 122 |
| Fatigue life remaining after indication, % | 1.62 | 1.76 | 1.65 | 0.82 | 1.29 | 2.43 | 4.78 | 3.37 | 1.72 | 1.76 |
| Position of failure surface relative to extensometer midspan, 0% = midspan, 100% = span edge | 175% | 175% | 0% | 100% | 100% | 150% | 125% | — | — | — |
| Sense of initial HSE change | Falls | Falls | Falls | Falls | Falls | Rises | Rises | Falls | Falls | Falls |

Fig. 53

|  | Specimen | | | | | | | | |
|---|---|---|---|---|---|---|---|---|---|
|  | MSD-1a | MSD-1b | MSD-2 | MSD-3 | MSD-4 | MSD-5 | MSD-6 | MSD-7 | MSD-8 |
| Nominal peak tensile load, lb | 780 | 2,340 | 2,000 | 2,000 | 2,000 | 2,000 | 1,500 | 1,500 | 1,500 |
| Nominal peak tensile stress, psi | 17,333 | 52,000 | 44,444 | 44,444 | 44,444 | 44,444 | 33,333 | 33,333 | 33,333 |
| Nominal minimum tensile load, lb | 78 | 234 | 200 | 200 | 200 | 200 | 150 | 150 | 150 |
| Nominal minimum tensile stress, psi | 1,733 | 5,200 | 4,444 | 4,444 | 4,444 | 4,444 | 3,333 | 3,333 | 3,333 |
| Cycles to failure | No fail at $10^5$ | 2,550 | 6,888 | 5,829 | 7,923 | 7,891 | 27,008 | 24,180 | 31,795 |
| Cycles of fatigue life remaining after indication |  | 205 | 649 | 833 | 817 | 1,138 | 3,307 | 2,441 | 3,769 |
| Indication based on slope or curvature |  | Slope | Slope | Slope | Curv. | Curv. | Curv. | Curv. | Curv. |
| Fatigue life remaining after indication, % |  | 8.04 | 9.42 | 14.29 | 10.31 | 14.42 | 12.24 | 10.10 | 11.85 |
| HSE plateau value | 0.07 | 0.92 | 0.67 | 0.62 | 0.63 | 0.62 | 0.31 | 0.31 | 0.32 |

Fig. 56

|  | Specimen | | | | | | | |
|---|---|---|---|---|---|---|---|---|
|  | Corroded | TM-1 | TM-2 | TM-3 | TM-4 | TM-5 | TM-6 | TM-7 |
| Indication based on: | Slope | Curv. | Slope | Slope | Slope | Slope | Slope | Curv. |
| Cycles for indication >UCL or <LCL | 48,690 | 32,595 | 41,217 | 24,985 | 43,393 | 43,949 | 38,997 | 33,026 |
| Cycles to failure | 50,546 | 33,133 | 41,955 | 25,404 | 43,750 | 44,727 | 39,969 | 34,682 |
| Cycles of life remaining after indication | 1,856 | 538 | 738 | 419 | 357 | 578 | 972 | 1,656 |
| Fatigue life remaining after indication, % | 3.67 | 1.62 | 1.76 | 1.65 | 0.82 | 1.29 | 2.43 | 4.78 |
| Position of failure surface relative to extensometer midspan, 0% = midspan, 100% = span edge | — | 175% | 175% | 0% | 100% | 100% | 150% | 125% |
| Sense of initial HSE change | Falls | Falls | Falls | Falls | Falls | Falls | Rises | Rises |

Fig. 92

NONLINEAR STRUCTURAL CRACK GROWTH MONITORING

STATEMENT OF GOVERNMENT RIGHTS

This invention was made with Government support under Contract Number DE-AC05-96OR22464 awarded by the United States Department of Energy to Lockheed Martin Energy Research Corporation, and the United States Government has certain rights in this invention.

FIELD OF THE INVENTION

The invention relates generally to determinations of the remaining useful life of structures and structural elements. More particularly, the invention relates to methods and apparatus enabling the nonlinear detection of imminent structural failure due to induced crack growth.

BACKGROUND OF THE INVENTION

Structural elements of any kind are subject to a variety of stresses that will ultimately result in the failure of the element. Examples of stresses are tensile, flexure, or shear stresses resulting from applied loads, the loads being either (a) statically or (b) regularly or irregularly periodically applied. Environmental corrosion can also constitute a stress to the structure. The applied load and environmental stresses, each acting separately or in combination, result in the creation and propagation of cracks in the structural element. The proliferation of cracks eventually causes the failure of the element.

It has long been a goal of those concerned with the useful life and eventual failure of structural elements to accurately predict the imminent failure of such elements. A primary consideration is safety, inasmuch as the failure of an element in, for example, a bridge or a mechanism such as a train car, can have a direct effect on the safety of people using the bridge or riding the train. A second significant concern is economics. While allowing a structural element to approach too closely its estimated time of failure creates the risk of an earlier than expected failure, which is a significant safety risk, repairing or replacing the element too early in its useful life is expensive. Utilizing too large a safety factor can waste a significant portion of the actual useful life of the element, contributing to higher costs for the element and/or the structure of which it is a part.

One type of failure of a structural element is tensile fatigue failure. Tensile fatigue causes the propagation of fatigue cracks, and hence to failure of the element. An analytically simple method of predicting tensile fatigue failure due to fatigue crack growth is to subject a statistically significant number of the structural element in question to empirical and/or experimental end-of-life (EOL) testing. This involves testing to destruction under stress conditions intended to duplicate those expected to be found in actual use. The results enable a determination of a mean value for and the variability in actual time to failure for a given set of loading, frequency, and environmental conditions. A predetermined safety factor can be incorporated in a prediction of structural service life to balance safety against utilizing as much of the useful life of the element as possible.

This method and equivalent methods for predicting failure due to other types of stress, however, are cumbersome, expensive, and time-consuming. Moreover, in the aforementioned fatigue failure method, for example, the material property determination of a mean value and the variability of the number of cycles to failure is also affected by the nature and frequency of the applied loadings and the environmental conditions over the service life of the structure. In addition, for multiple loadings, it requires a knowledge of the critical type of loading. Also, where the safety is concern is very high, such as for a high speed mass transit vehicle, the predictive window provided by such tests is too broad for accurate use with a particular structural member. Imposing a high enough safety factor to counter this breadth simply results in the practical loss of useful life.

An illustrative but not limiting example relates to aircraft frames. The structural lifetime of military and civilian aircraft is ultimately limited by the airframe fatigue life. The precise prediction of the future time of failure is made very difficult because the fatigue crack growth-limited lifetimes may vary by a factor of as much as ten (10) to twenty (20). Imposing a safety factor to account for this variation results in the grounding of many aircraft at times that are far short of the inherent fatigue lifetime thereof in an attempt to limit the possibility of fatigue failure in the theoretically weakest airframe in the fleet.

Prior to about the late 1970's, the design criteria for airframe fatigue life, known as "safe life," were based on experimentally-derived stress-number of cycles to failure (S-N) curves. This technique used the empirical and experimental approach addressed above, and suffers from the same drawbacks. The assumptions that must be made with regard to the effects of unknown or partially known variables in the service life of the airframe require factors of safety to be enforced on the entire fleet to account for the possible extremes in exposure of some members of the fleet. That is, it must be assumed that not only is every structural element as weak as the weakest element tested, but that each airframe will encounter the worst possible environment with respect to adverse effects on the member.

Designers of military aircraft next adopted a fracture mechanics approach, also referred to as "damage tolerance." This method is based on measuring the size of existing cracks in a structural element. Predictive calculations based on these measurements are used to estimate the remaining useful life of the element. Many civilian and military aircraft now nearing the specified airframe lifetimes, however, were designed and built prior to the use of fracture mechanics as design tools. Assessing these aircraft now with a view to using fracture mechanics involves a time and cost prohibitive evaluation. Moreover, even an exhaustive evaluation cannot determine the stress and fatigue history of the structural elements, which makes any predictive calculations inherently suspect. Finally, certain needed variables, such as initial stress resistance and other factors, were simply not measured or calculated for the existing airframes, creating a situation in which predictions either cannot be made or in which certain variables must to themselves be estimated. This adds, of course, an entirely separate degree of uncertainty to the use of this methodology on existing elements. These aircraft now face premature retirement because there are no tools and methods available to assure continued safe operation with confidence.

The current method of crack growth measurement requires periodic, costly nondestructive evaluation (NDE) of these existing airframes and the constituent elements, and concomitant meticulous record keeping to record and track crack growth. The current method also suffers from the inherent uncertainties stated above. In addition, these uncertainties are compounded by three known and routinely encountered factors. First, where multiple cracks are created and are propagated, the stress fields of the multiple cracks can and will interact with each. This interaction makes a determination of a critical crack size, with respect to failure, very difficult. Also, a given structural element is subject to widely varying types and magnitudes of loadings, and in the presence of widely varying degrees of corrosive environments. The compounding nature of these variations makes analytical predictions based on fracture mechanics sufficiently imprecise that, again, large factors of safety are required. These factors introduce variables for which the current methods can only compensate for by introducing large factors of safety, or by requiring additional loading and environmental exposure record keeping. Moreover, it is known that overstress to an element tends to slow, at least temporarily, the rate of crack growth. This is analytically difficult inasmuch as there is no means of detecting, predicting, and accounting for either the overstress or the existence and extent of the slowing. Other variables also affect the method, of which the foregoing are well-known examples.

Thus, despite the need for and importance of accurately predicting failure caused by crack growth, existing methods are cumbersome, expensive, and time-consuming. There are also uncertainties for which no adjustment is currently available. Finally, current methods rely in whole or in part on statistical calculations for a set of elements, rather than for the single element in question. The predictive "window" or interval is thus unacceptably large, leading to structural elements being taken out of service long before the actual end of the useful life thereof. Methodologies providing an improved prediction and thus a higher level of confidence, and apparatus to implement the methodologies, are needed. In addition, methods and apparatus for monitoring individual elements are needed to aid in the task of significantly narrowing the predictive interval of failure.

SUMMARY OF THE INVENTION

It is an object of this invention to provide a method and apparatus for detecting and providing an indication of imminent failure in a structural element.

It is a further object of this invention to provide a method and apparatus for monitoring changes in crack growth rate in structural materials.

It is another object of this invention to provide a method and apparatus for manipulating data in real time to provide a detection of a given stage of crack growth in a structural element where the crack growth is induced by loading, creep, stress, corrosion or a combination thereof.

It is also an object of this invention to provide a method for converting physical data from a structural element into a measure at least proportional to crack growth rate.

Another object of the invention is to provide a method and apparatus for relating crack growth rates in structural elements to an indication of the imminent failure of the elements.

Still another object of this invention is provide a method and apparatus incorporating a unique nonlinear filter for crack growth-related data to enable the accurate detection of significant changes in such data.

It is likewise an object of this invention to provide apparatus for detecting loading and stress factors for a structural element and for creating as an output an indication of the structural status for the structural element.

It is moreover an object of this invention to provide apparatus including sensors associated with a structural element from which data is received and manipulated to provide an indication related to the end of service life for the structural element.

It is also an object of this invention to provide a method and apparatus for monitoring crack growth rate-related data in structural elements to provide an indication of the accelerating crack growth rate indicative of the imminent approach of the end of service life for the structural element.

It is a further object of this invention to provide a method and apparatus for converting load and displacement data for a structural element to a measure of time-dependent absorbed strain energy as a means of monitoring and measuring the rate of crack growth within the structural element.

It is an object of this invention to accomplish the foregoing method and provide the foregoing apparatus in a manner incorporating nonlinear filtering means to monitor crack growth in structural elements and provide an indication of imminent failure in such elements due to such crack growth.

These and other objects of the invention are achieved by providing a method for the nonlinear prediction of failure in a structural element subject to a load, the method including the steps of sensing load- and strain-related data for said structural element, generating a crack-growth function relating said load- and strain- or load- and displacement-related data to an interval, deriving from said crack-growth function at least one indicator function, monitoring trends in said at least one indicator function, and providing an indication when said monitoring detects an end-stage trend in said at least one indicator function.

These and other objects of the invention are achieved by providing a method for the nonlinear prediction of failure in a structural element subject to a load, the method including the steps of sensing load- and strain- or load- and displacement-related data for said structural element, generating a crack-growth function relating said load- and strain- or load- and displacement-related data to an interval, deriving from said crack-growth function at least one indicator function and at least one limit function, monitoring said at least one indicator function and said at least one limit function, and providing an indication when said at least one indicator function and said at least one limit function converge.

These and other objects of the invention are also provided by an apparatus for predicting failure of a structural member, said apparatus having at least one sensor for sensing load- and strain- or load- and displacement-related data representative of a load and strain to which said member is subject; interval counting means for counting a desired interval and providing an interval count associated with said load- and strain- or load- and displacement-related data; processor means operatively connected to said sensor means and said interval counting means for providing a crack growth function relating said load- and strain- or load- and displacement-related data to said interval count; processor means for deriving from said crack growth function at least one indicator function; means for monitoring said at least one indicator function and detecting trends in said function; and output means providing an indication when said monitoring means detects the onset of an end-stage trend in said at least one indicator function.

These and other objects of the invention are also provided by an apparatus for predicting failure of a structural member, said apparatus having at least one sensor for sensing load- and strain- or load- and displacement-related data representative of a load and strain to which said member is subject; interval counting means for counting a desired interval and providing an interval count associated with said load- and strain- or load- and displacement-related data; processor means operatively connected to said sensor means and said interval counting means for providing a crack growth function relating said load- and strain- or load- and displacement-related data to said interval count; processor means for deriving from said crack growth function at least one indicator function and at least one limit function; means for monitoring and comparing said at least one indicator function and said at least one limit function; and output means providing an indication when said at least one indicator function and said at least one limit function converge.

BRIEF DESCRIPTION OF THE DRAWINGS

FIG. 4 is a table (Table 1) showing fatigue test results for experimental coupons P36-O-45, P36-O-46, P36-O-47, and P36-O-48.

FIG. 10 is a table (Table 2) showing experimental results using control limits as an indicator of remaining fatigue life for the samples in Example I, below.

FIG. 13 is a table (Table 3) of the fatigue test results for the aluminum coupon samples discussed in Example II, below.

FIG. 53 is a table (Table 4) containing data regarding slope and curvature as indications of imminent fatigue failure for aluminum test coupons discussed in Example II, below.

FIG. 56 is a table (Table 5) showing fatigue test results for aluminum coupons tested according to Example III, discussed below.

FIG. 92 is a table (Table 6) comparing the fatigue data for a corroded, unnotched aluminum coupon (Sample SM-TN-AL-CO-CS-UN-1 from Example IV below) with the data from Example II (Table 4 in FIG. 53.

DETAILED DESCRIPTION OF THE INVENTION

Figure 1:
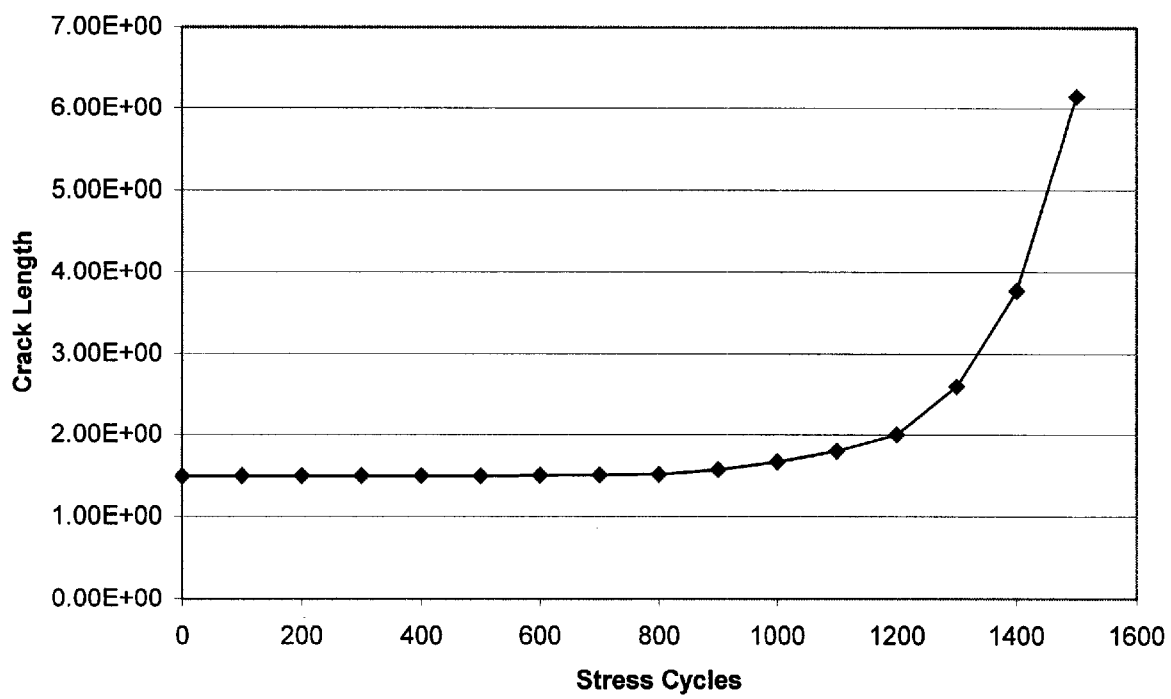
FIG. 1 is a graph showing a typical crack growth curve, with crack length plotted as a function of the number of stress cycles.

It is known that under normal conditions, i.e., in the absence of a catastrophic event, the ultimate failure of a structural element due to loading and/or corrosion is the result of the appearance and growth of cracks in the element. At some point, the number and extent of cracks weaken the element sufficiently that it fails. For a given element, the point of failure can be measured by testing the element to destruction. While such testing cannot be applied to an element in actual use, the destruction of the element being that which is to be avoided, the testing of a sufficient number of elements can provide a statistical model for predicting a point of failure.

Using such a statistical model has severe drawbacks. For the sake of safety, the predicted useful life of a structural element must be limited to the lowest, or earliest, boundary of the statistical point of failure. Thus, the effective useful life of a set of elements is limited to the weakest one of such elements, because to exceed this boundary risks the failure of some number of the set. This is costly, inasmuch as many, and perhaps the majority of the elements, could safely remain in use for a longer time.

The use of such a model also entails the use of costly and time-consuming NDE to compare the condition of a given structural element to the model. Moreover, the model cannot reasonably and reliably predict in advance the occurrence of the problems set forth above, e.g., multiple cracks, to allow an a priori prediction of useful lifetimes for individual structural elements without again requiring large safety factors.

It is thus a goal to develop a method and apparatus that overcome these problems and uncertainties. It is likewise a goal to enable monitoring of crack growth and growth rate in a given structural element. It is also a goal to find and utilize some characteristic of the crack growth itself to predict impending failure of the specific element in question with a high degree of reliability. Rather than relying on group statistics inherently having weakest and strongest members, predictions can be made based on each individual element. The method and apparatus of the current invention achieve these goals.

Cracks and crack growth in structural elements are broadly due to loading, corrosion, or both. Cracks and crack growth due to regularly or irregularly periodic loading is referred to herein as fatigue cracks and fatigue crack growth, respectively. Damage due to a constant loading in the absence of corrosion is referred to as creep. Creep crack growth is a form of crack growth wherein viscous flow under static loading occurs at the crack tip, leading to time-dependent crack growth. Crack growth that is predominantly due to corrosion of an element under static loading is referred to as stress corrosion. The corrosion preferentially attacks the material under high stress at the crack tip, leading to crack extension in a time-dependent fashion.

Structures can be loaded in three ways. These are termed tension, flexure, and shear. Cracks and crack growth caused by these loadings can extend in three ways or modes. There is an opening mode referred to as Mode I created by tensile or flexure forces. The in-plane shear mode (Mode II) is due to in-plane shear forces, and out-of-plane shear mode (Mode III) is due to out-of-plane shear forces such as torsion. The method and apparatus of the current invention are applicable to all three modes of crack extension where subcritical crack growth occurs prior to final fracture or failure.

Corrosion can be caused by a variety of environmental factors. Examples of corrosives are salt, such as in structures exposed to sea water, and pollutants such as oxides of sulfur. Corrosion itself causes crack growth. In structural members also subject to the forces identified above, corrosion is usually observed to exacerbate the crack growth caused by such forces.

A combination, or all, of these load, stress, and corrosion factors may influence crack growth. A structural member may be under a constant load and also subject to a periodic increase or decrease in load. A member or element subject to periodic loading may also be exposed to a corrosive environment. Typically, one cause of crack extension or growth predominates.

Without limiting the invention, it is applicable in its preferred embodiments to the following primary modes of crack extension:

(a) fatigue crack growth, due to alternating loads in the absence of creep and corrosion;

(b) corrosion fatigue crack growth, due to the combined effects of alternating loads and corrosive environments;

(c) creep crack growth, due to steady loads in the absence of corrosion; and (d) stress corrosion crack growth, due to the combined effects of stress and a corrosive environment.

Fatigue and corrosion fatigue crack growth can be considered together, with creep crack growth and stress corrosion crack growth each requiring slightly differing manipulations of data.

The typical crack growth relationships are generally known, and are applicable to a wide variety of materials subject to failure due to crack growth. These materials include, among others, metal and metal alloys and fiber composites. A typical crack growth curve for metals is illustrated in FIG. 1. This graph shows crack length as a function of the number of alternating load or stress cycles. It shows that crack length as a function of cycles remains very low for the majority of the useful life of the material. The length then exhibits a significant perturbation, in this case, an significant upward rise.

Figure 2:
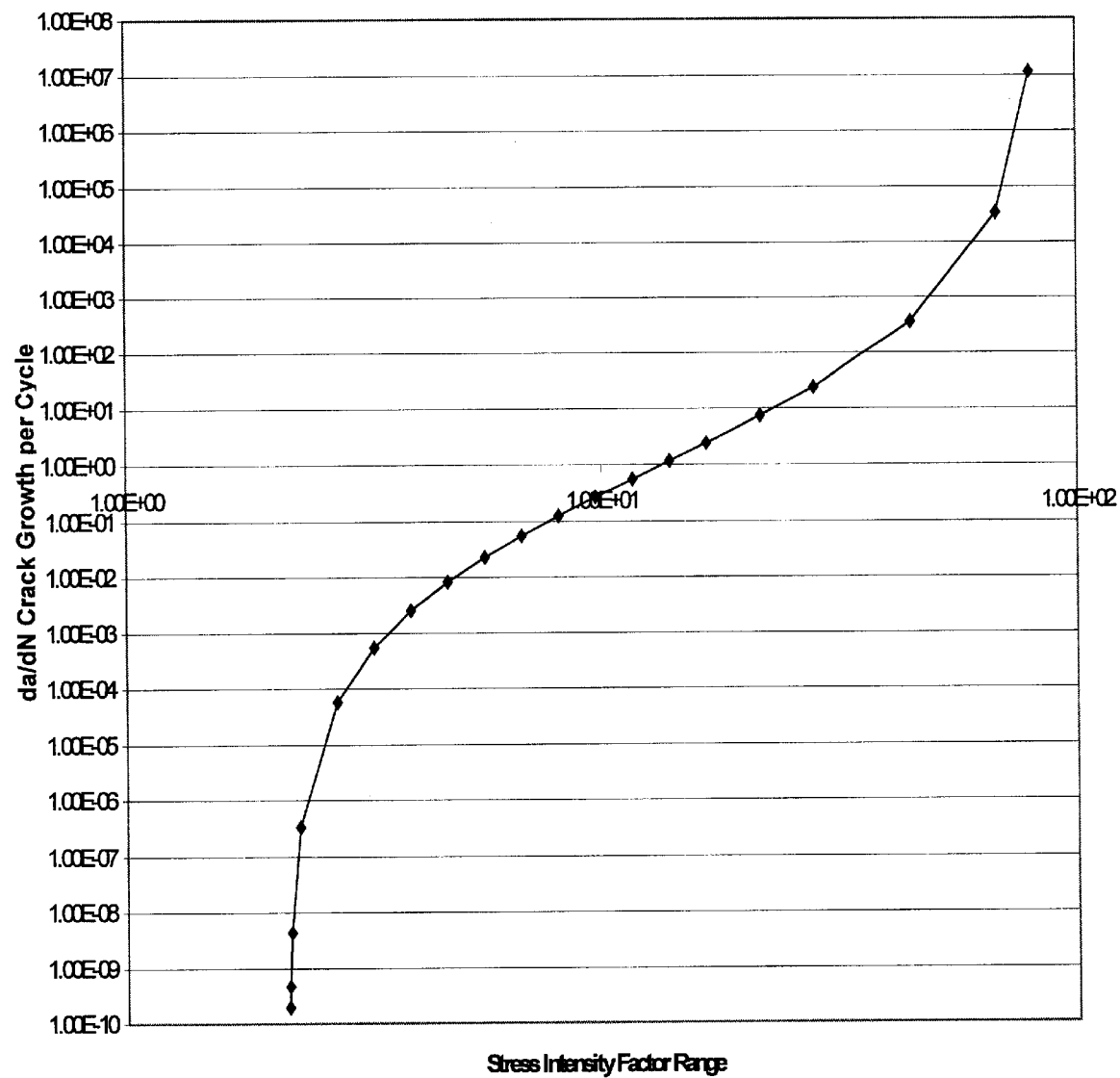
FIG. 2 is a graph showing the trilinear form of a typical fatigue crack growth rate relation for metals.

Crack growth per cycle can be plotted as a function of the stress intensity factor range, as is illustrated in FIG. 2. This relationship exhibits an initially high rate of growth. The rate then "plateaus" to a relative degree, after which there is again observed a significant perturbation in the growth rate. The growth rate curve, in its nominal form, is thus an essentially trilinear curve. For many materials, there is exhibited an initial drop in the rate (not shown in FIG. 2 due to plotting scale) prior to the initial rise.

Monitoring crack length or area, crack growth, or crack growth rate as direct physical phenomena, however, requires time-consuming and expensive evaluations such as those referenced above. Such monitoring also requires meticulous record keeping, and does not eliminate the need to use broad statistical models for predicting end of life or the close approach thereto.

The invention, in essence, is a method involving sensing appropriate physical values for a structural element, such as load, strain, and/or displacement data. Load- and strain- or load- and displacement-related data, or other physical data sensed from the element, provide a direct or indirect measure of the energy applied to and/or absorbed by the structure. This energy, referred to generically herein as HSE, is then calculated as a function of a load cycle interval or a time interval. An indicator function, to be used as described, is derived from this function. The energy that is related to crack growth and crack growth rate are extracted from this curve by means of a nonlinear filter, a preferred one of which is set forth below. The filtered data can then be used as an indicator function to determine the onset of the final stage trend, that is, the onset of final-stage crack growth. The onset of this trend is a reliable indicator of the imminent onset of failure in the element.

The HSE function, after filtering, can itself be used to detect trends. In a preferred mode, the slope function, curvature function, or both, are derived from the HSE function. Either or both of these functions can be used directly as the indicator function to be monitored to detect trends. Alternatively, one or more limit functions can be derived from the HSE function and/or the slope function and/or the curvature function, and these limit functions can be used in conjunction with the indicator functions to detect the desired trends. Apparatus for implementing the method are also disclosed.

The current invention encompasses the use of local hysteresis strain energy (LHSE), and the nonlinear analysis thereof as described, as an accurate means of monitoring crack growth and growth rate in a material subject to fatigue and corrosion fatigue crack growth. For these types of crack growth, the invention also encompasses a means for using LHSE to accurately detect the approach of failure due to crack growth. For creep crack growth, the invention encompasses the use of load- and strain-related data as a logarithmic function of time to monitor crack growth in structural elements subject to a constant load. Load- and strain-related data as a linear function of time enables the monitoring of crack growth in elements subject to stress corrosion.

Methods and apparatus for the real-time or near real-time monitoring of materials are provided thereby. The methods and apparatus are generally applicable to predicting the approach of the final stages of crack dominated failure in structures and structural elements, whether such cracks are the result of fatigue generated by loading cycles or are the result of time dependent changes in strain energy in creep crack growth or stress corrosion assisted crack growth.

In general, crack initiation and growth require energy consumption. This energy for crack growth, along with other forms of energy consumption internal to the structural member, is supplied as external energy by the application of dynamic or static external loadings, and affected by corrosion. When other forms of internal energy consumption are sufficiently low compared to the energy consumed by crack growth, then LHSE (for fatigue and corrosion fatigue) or other load- and strain-related data can be appropriately measured or calculated and used as a representation of crack growth. For convenience, LHSE and the load- and strain-related data used for creep and for stress corrosion are jointly referred to as HSE.

HSE can be appropriately measured or calculated and used as a representation of crack growth. HSE is plotted as a function of (1) the number of loading cycles for an element subject to loads or (2) predetermined time segments for an element subject to constant load or to stress corrosion, to generate a strain or HSE curve. As referred to herein, a loading cycle with respect to regularly or irregularly alternating loads is the interval between (i) a local maximum load value through a local minimum value to the ensuing maximum (max-min-max) or (ii) a local minimum through a local maximum to the ensuing minimum (min-max-min). The predetermined time segment can be measured by any clocking means.

According to the method of the invention, HSE is calculated from data obtained in well-known ways. For structural elements made of metals and metal alloys, devices such as tensiometers, extensometers, strain gauges, and displacement sensors will provide load and strain data. Similar devices can be used to measure changes in load and strain as a function of time. For materials such as composites, embedded sensors may be used.

One sensor well-suited for composites consists of embedded optical fibers. The light transmission quantities for the embedded fibers will change as cracks develop. Crack growth will change the length or curvature of the fibers, or will break the fibers. The light transmission thus serves as a measure of crack growth. The fibers may thus be used to measure strain as described in U.S. Pat. No. 4,191,470, incorporated by reference; to measure pressure as described in U.S. Pat. No. 4,770,492, incorporated by reference; and/or load as described in U.S. Pat. No. 4,421,979, incorporated by reference.

The advantage to using embedded sensors, and particularly sensors such as light fibers, is the novel ability to measure data over a broad area and/or throughout a volume, as opposed to at a point source. Using these sensor technologies, which may be expanded beyond use solely in composites, provides a means of creating novel "smart" structural elements, wherein the element itself contains the sensors and data can be obtained directly therefrom. By sensing areal and/or volumetric data, the determination of crack growth and crack growth rate is both more comprehensive and more reliable.

For fatigue and corrosion fatigue crack growth, the load and strain or displacement data are integrated over the load cycle to determine LHSE. The calculation is a loop integral function. The load cycle is determined by comparing the physical data to a clock output to determine the selected min-max-min or max-min-max cycle described above. For creep crack growth and stress corrosion crack growth, the load- and strain-related data are integrated over a time interval, providing a measure of energy consumption for the time interval. Energy consumption, whether measured as LHSE or as the time-dependent change, serves as the measure of crack growth.

The foregoing calculations are performed by a processor operatively connected to the data measuring devices described. Processors capable of performing the described integrations, and the calculations further described below, are known in the art. The processor may consist of dedicated circuitry designed to perform only the necessary calculations, or can be a general purpose processor or computer programmed to perform the calculations. The clock can be associated with the structural elements and/or the sensors, or can be part of the processor.

For each type of crack growth, the processor calculates HSE values. An HSE curve is then plotted. For fatigue and corrosion fatigue, LHSE is plotted as a function of the number of load cycles. For creep, HSE in the form of the integrated load- and strain-related data is plotted as a function of time, and for stress corrosion, HSE in the form of integrated load- and strain-related data is plotted as a function of time on a logarithmic scale. The resulting curve is referred to as the HSE curve.

It is theoretically possible, and within the scope of this invention, to analyze this HSE curve itself to determine when crack growth has shifted into a new phase (secondary or tertiary), the shift being the indication of imminent failure. Practically, however, there are many independent variables experienced in use. Also, there is the effect of variations in HSE caused by differences, for example, in load amplitude and frequency, in material, and in other factors affecting the HSE values. These create a level of "noise" in the curve that severely and negatively affects the usefulness of this first-order curve.

The inventors hereof have discovered that by applying a novel, zero-phase quadratic filter to the HSE curve, the HSE curve can be smoothed and made useful. The HSE curve after smoothing provides general trends, but improved forewarning can be obtained by examining the slope or curvature of the HSE curve. The data from the HSE curve is manipulated to derive the curvature and/or the slope of the HSE curve. While either value alone is useful in predicting end-phase crack growth, the preferred embodiment of the invention utilizes both the curvature and the slope values.

Because of the low-amplitude variation in the HSE curve, the curvature and slope values also exhibit random variations that must be distinguished to achieve accurate predictions. This distinction is achieved by treating the values of the slope and curvature as statistical variables. This is similar to the construction of an industrial process control chart.

The slope and curvature functions can be used for detecting trends, and especially the end-phase trend in crack growth rate that indicates the imminent EOL for the structural element. A preferred method for monitoring trends in the slope and curvature functions is to establish limit functions that can be compared to the slope and curvature functions to determine the onset of a trend. For each set of slope values and curvature values, an upper control limit (UCL) and lower control limit (LCL) are established. These limits are calculated as the mean value of the slope or curvature plus or minus, respectively, a predetermined multiple of the calculated standard deviation for the value. These two sets of three curves, that is the slope with its UCL and LCL and the curvature with its respective UCL and LCL, can be recorded and monitored in any convenient manner including but not limited to graphically (e.g., by trace), visually (e.g., on a monitor), and/or as electronically stored data (e.g., as RAM or on magnetic tape).

It has been discovered by the inventors hereof that a reliable and accurate predictor of imminent failure is a statistically significant perturbation in the curvature and/or slope values. That is, failure can be considered imminent at a point at which either the slope or the curvature values intersect with either the UCL or LCL curves.

The foregoing is detailed as follows. While this explanation is specific to the case of fatigue crack growth and corrosion fatigue growth, it is equally applicable to creep crack growth and stress corrosion, as will be seen by those of skill in the art. That is, the method is applicable to crack growth as represented by the energy consumed by crack growth as defined above.

The technique of considering crack growth in solids as a process of energy exchange, in which external energy as introduced is stored as internal strain energy, was introduced by Griffith. During the process of crack growth, which is an energy consuming process, the internal strain energy and any additional externally introduced energy from loading is transformed into new crack surface area. When the rate of change of internal strain energy per unit crack length increase equals the rate of consumption of surface energy due to additional crack surface creation, a crack will begin to extend. This critical strain energy release rate, called $G_{Ic}$, then becomes a criterion for the onset of initial crack extension. The subscript I indicates Mode I crack growth, as defined above, and the technique is also valid for the other two Modes II and III of crack growth.

This technique has been extended by Rice to elastic-plastic materials through the introduction of a nonlinear-elastic version of the same criterion, denoted as $J_{Ic}$. The method applies Green's theorem to nonlinearly-elastic loaded structures to express the sum of changes in internal strain energy plus changes in externally supplied energy due to crack growth. When the sum of these changes equals the surface energy of the material, a crack will begin to extend.

Criteria for the onset of crack growth in creep, or sustained loading of cracks, and in stress corrosion cracking ($K_{Icc}$, $J_{Icc}$) have been measured for various materials as material properties similar to $G_{Ic}$ and $J_{Ic}$.

From linear elastic fracture mechanics, the Griffith energy for crack extension is numerically equal to $$G_c = K^2/E = du/da \qquad \text{(Equation 1)}$$

where $G_c$ is the critical strain energy release rate, K is the stress intensity factor, E is Young's modulus, U is the potential energy (strain energy) available for crack extension, and da is the incremental crack extension.

During fatigue, dU is the change in strain energy per cycle. Assuming that this change in strain energy contributes to crack growth then, for fatigue crack growth, this represents the local hysteresis strain energy (LHSE as above) per cycle. Where N is the cycle number, fatigue crack growth rate per cycle is da/dN. If this is multiplied by the constant critical strain energy release rate for the material dU/da, then $$(da/dN)(dU/da) = dU/dN. \qquad \text{(Equation 2)}$$

This means that the quantity of LHSE consumed per cycle is linearly related to the quantity of crack growth rate per cycle and, when plotted, produces a curve that shifts from the fatigue crack growth rate curve.

During fatigue, crack growth typically occurs in three distinct phases. These are nucleation (crack initiation), stable crack growth (subcritical crack growth), and unstable final crack growth. It is the onset of the final stage that serves as an indicator of imminent failure, and the detection thereof therefore allows full use of the element without risking failure.

The foregoing is then applied as follows. The work consumed by the structural element under load is the force-through-distance energy, integrated over the work cycle. As indicated above, the "work cycle" can be a time interval. In the following, the work cycle is a load cycle.

The force in this case is the applied load, P. Elongation under load, measured for example as displacement in a critical area of the element, is $\delta$. The input strain energy for each cycle is $$E_{In} = \int P d\delta. \qquad \text{(Equation 3)}$$

over the loading portion of the cycle, where the integral is from $P_{MIN}$ to $P_{MAX}$. The LHSE, expressed as HSE, subtracts the strain energy over the unloading part of each cycle from Equation 3. HSE is then computed as the loop integral:

$$E = \oint P d\delta. \qquad \text{(Equation 4)}$$

Figure 3:
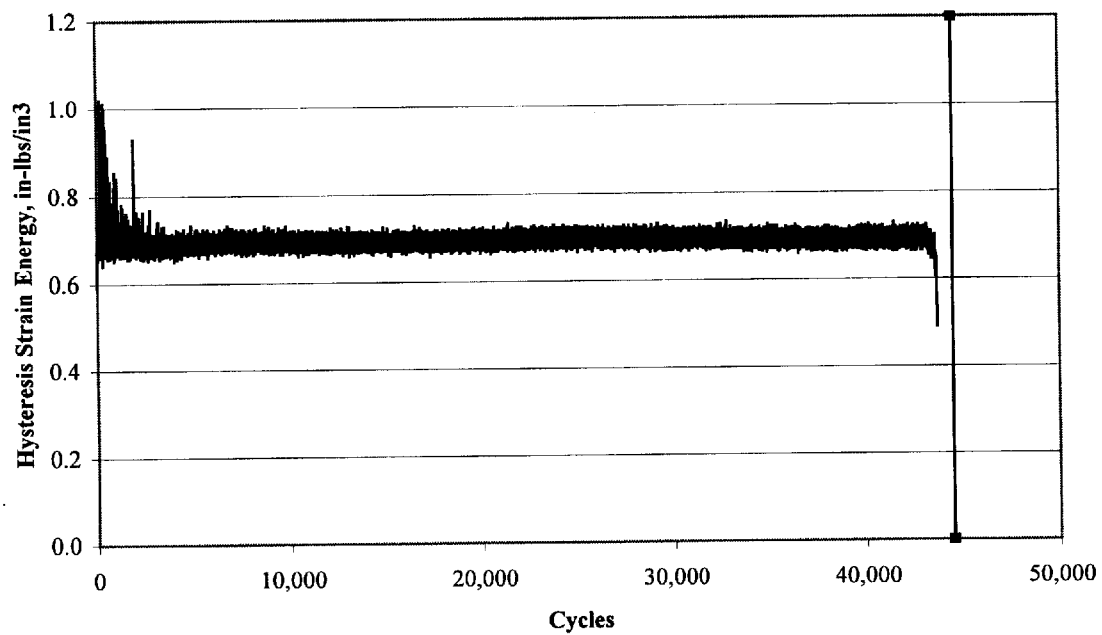
FIG. 3 is a graph illustrative of hysteresis strain energy plotted as a function of the number of load cycles taken for a sample of aluminum alloy.
Figure 5A:
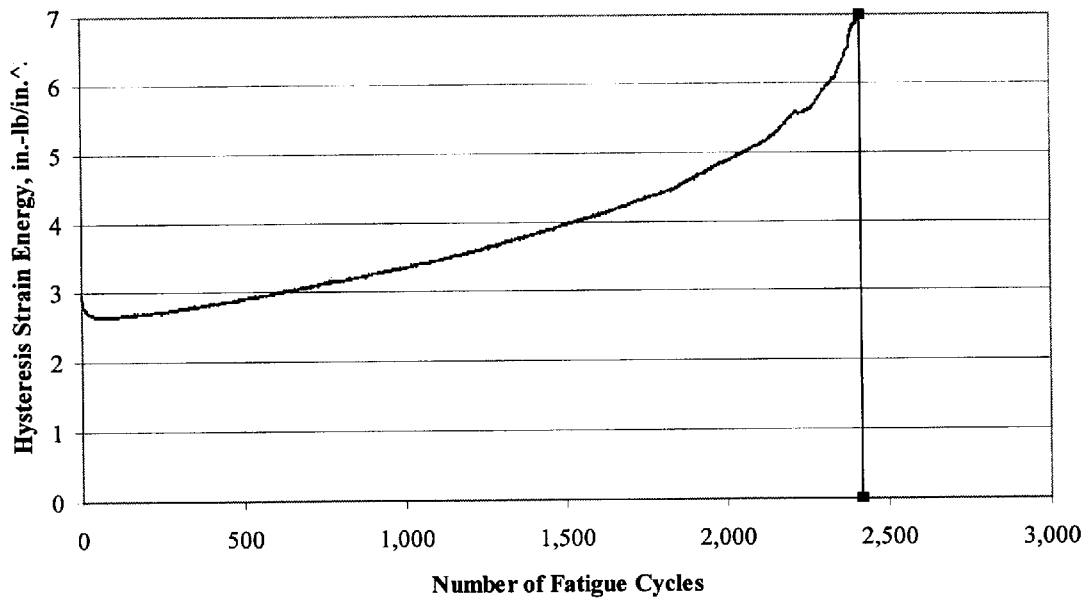
FIG. 5 shows the graphs of experimental data for hysteresis strain energy versus number of fatigue (load) cycles for experimental samples: (a) P36-O-45; (b) P36-O-46; (c) P36-O-47; and (d) P36-O-48.
Figure 5B:
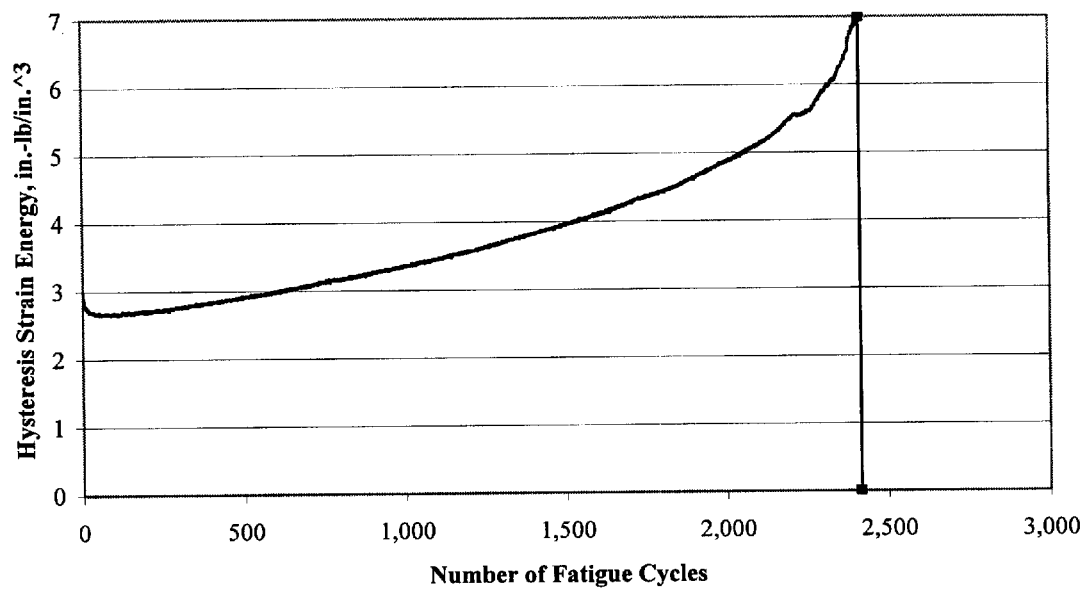
Figure 5C:
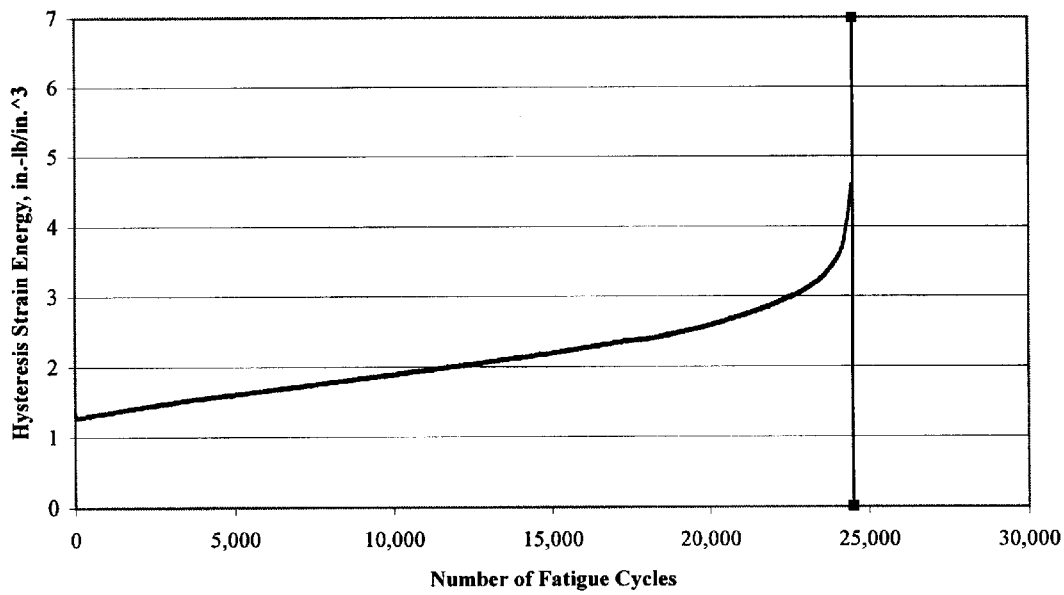
Figure 5D:
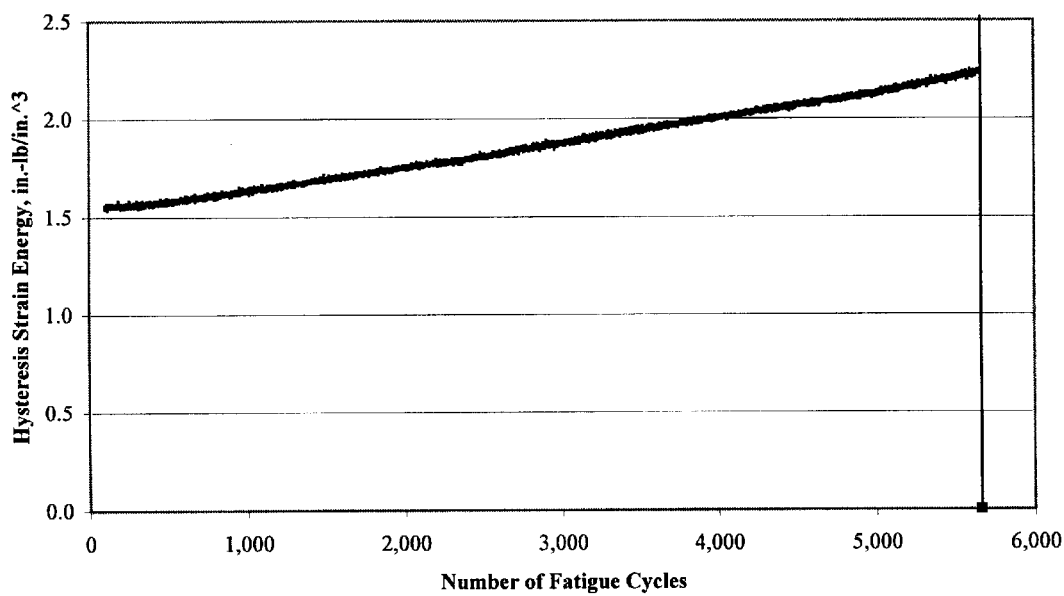
Figure 6A:
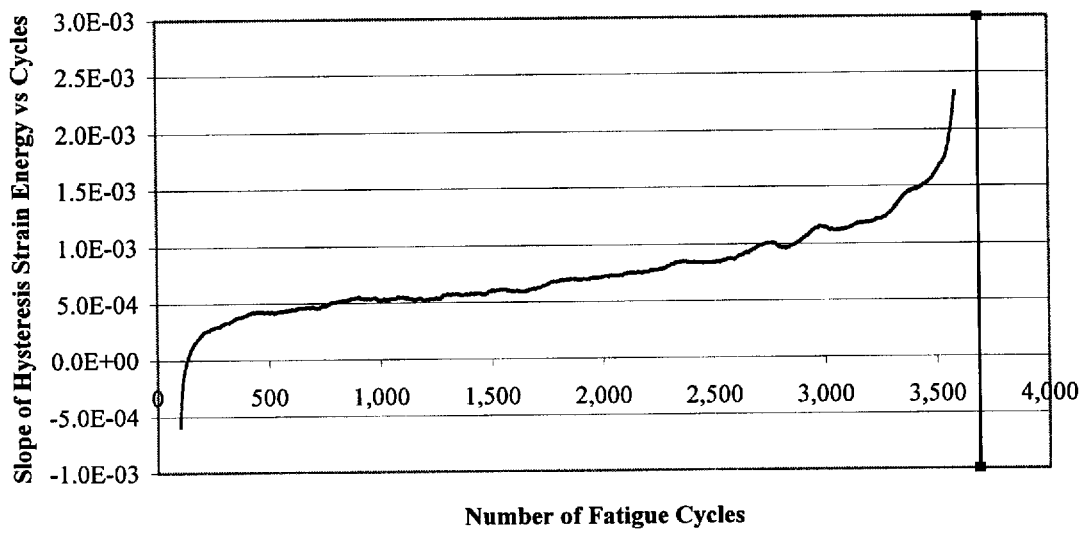
FIG. 6 shows graphs of the slope of hysteresis strain energy curves for the respective graphs in FIG. 3.
Figure 6B:
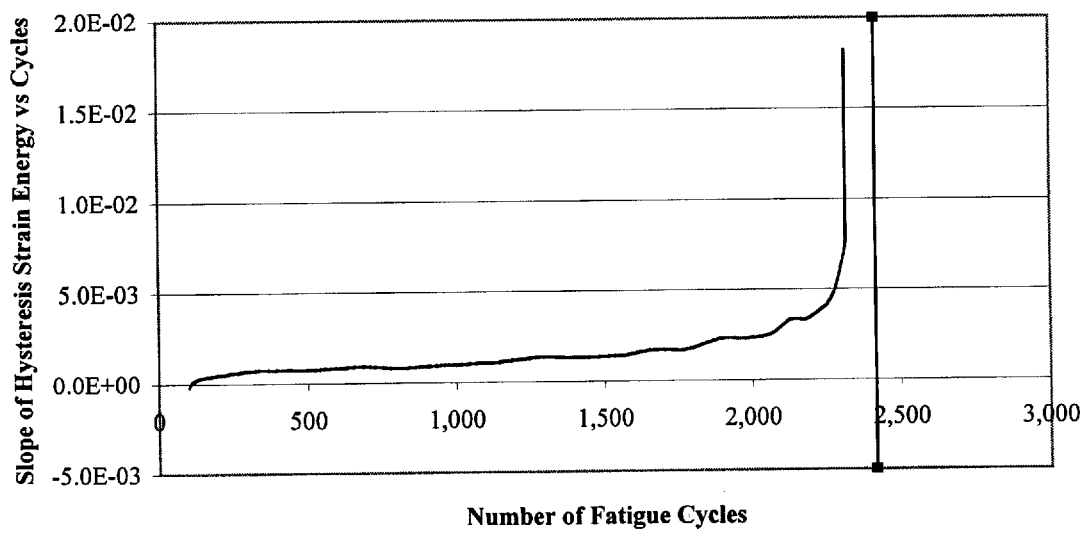
Figure 6C:
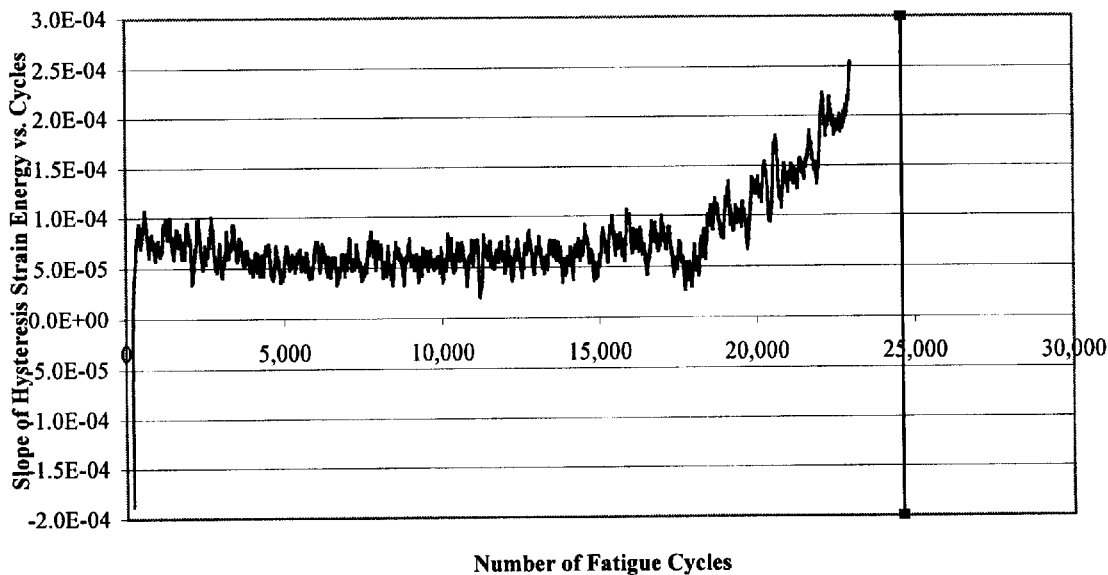
Figure 6D:
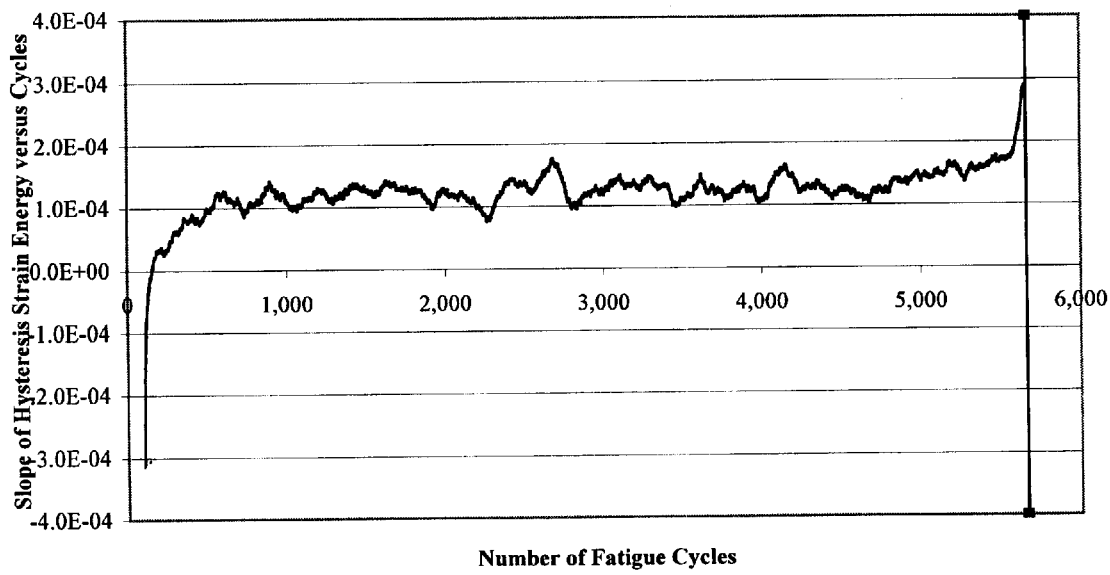
Figure 7A:
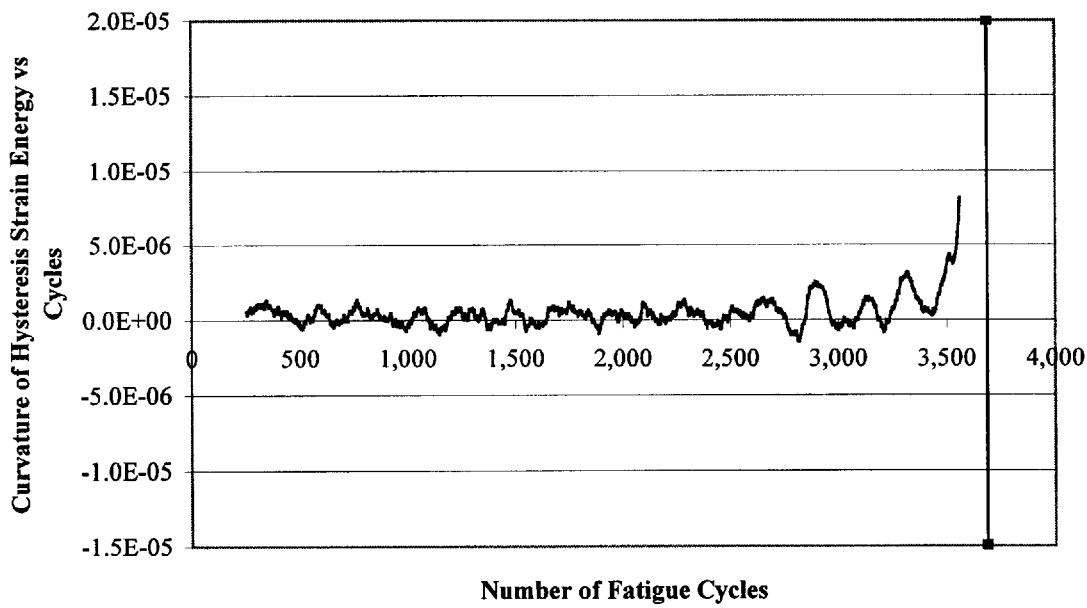
FIG. 7 shows graphs of the curvature of hysteresis strain energy for the respective graphs in FIG. 3.
Figure 7B:
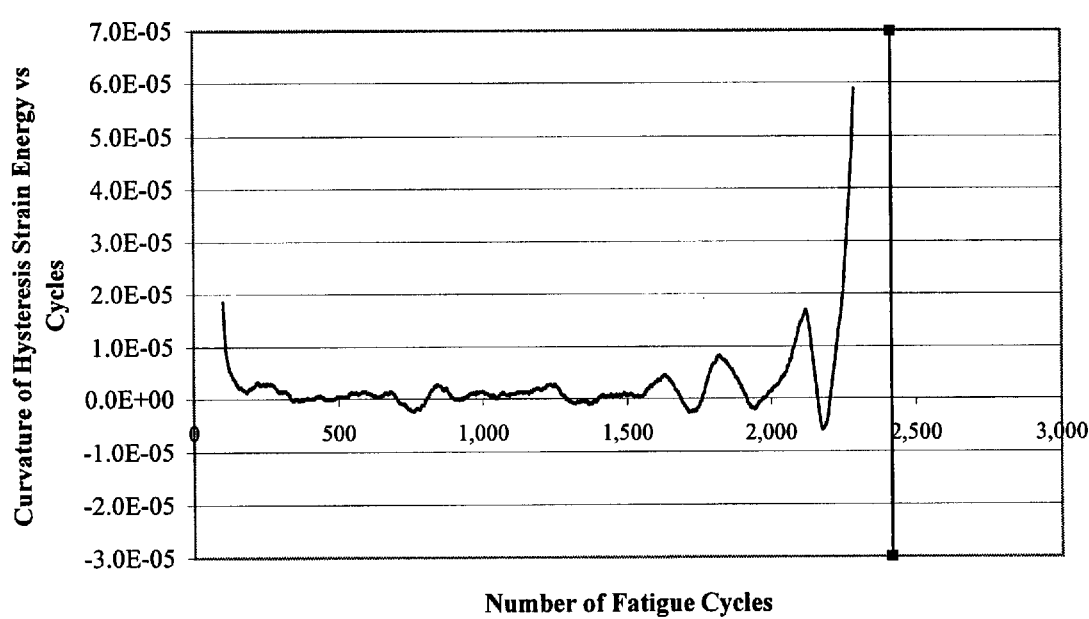
Figure 7C:
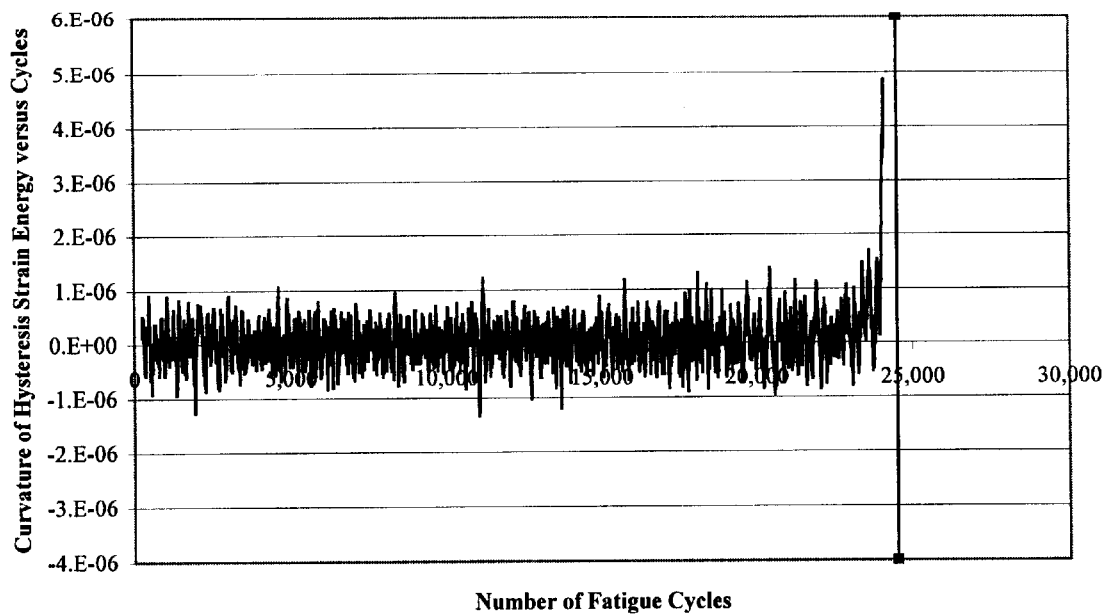
Figure 7D:
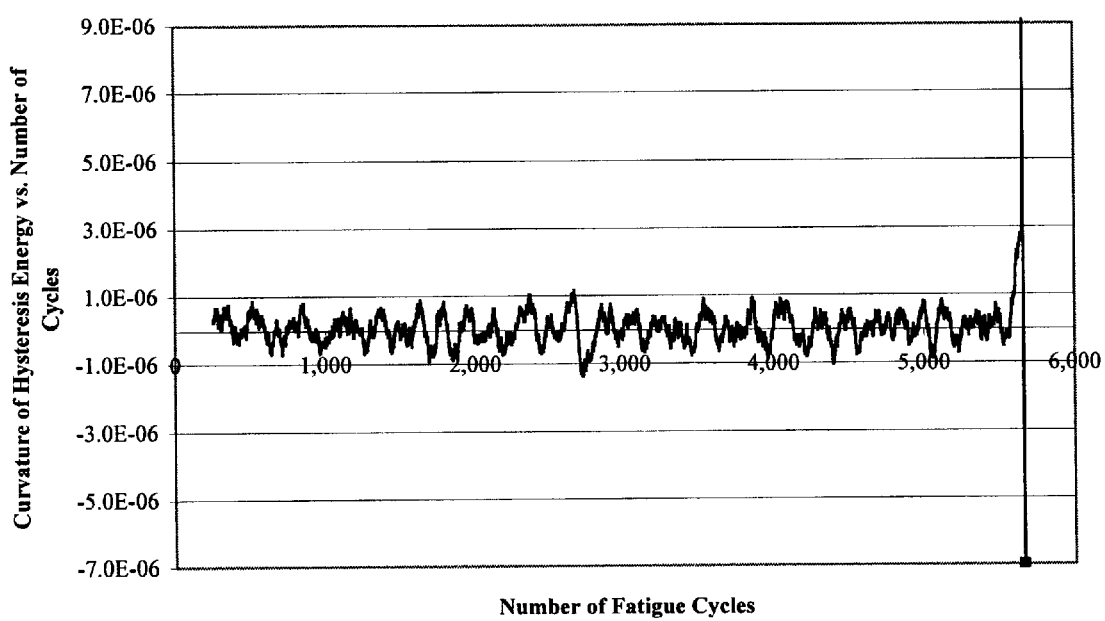
Figure 8A:
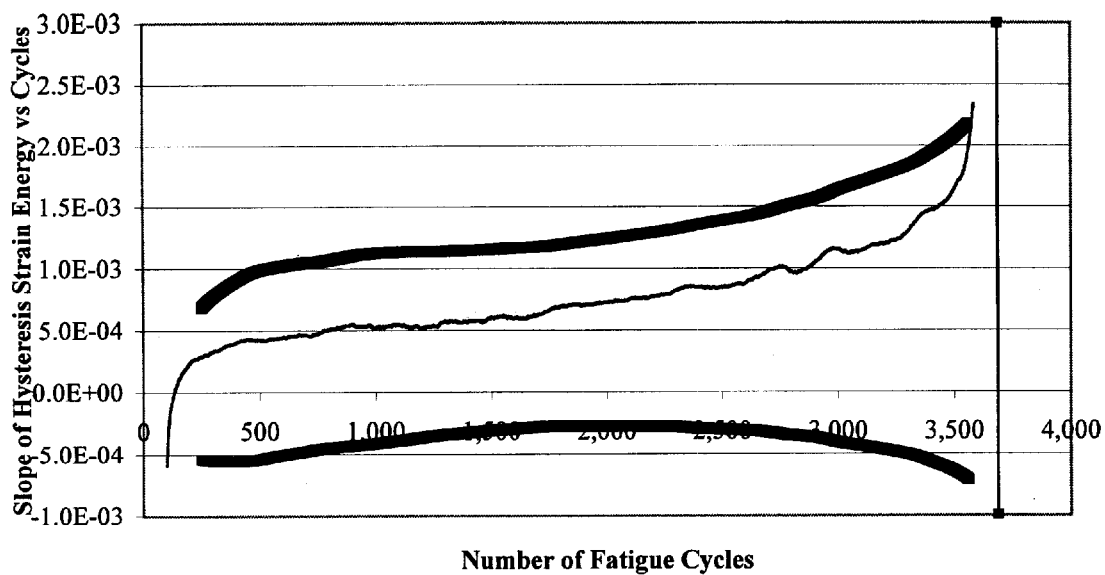
FIG. 8 shows graphs of the slope of hysteresis strain energy curves for the respective graphs in FIG. 3, with upper and lower control limits.
Figure 8B:
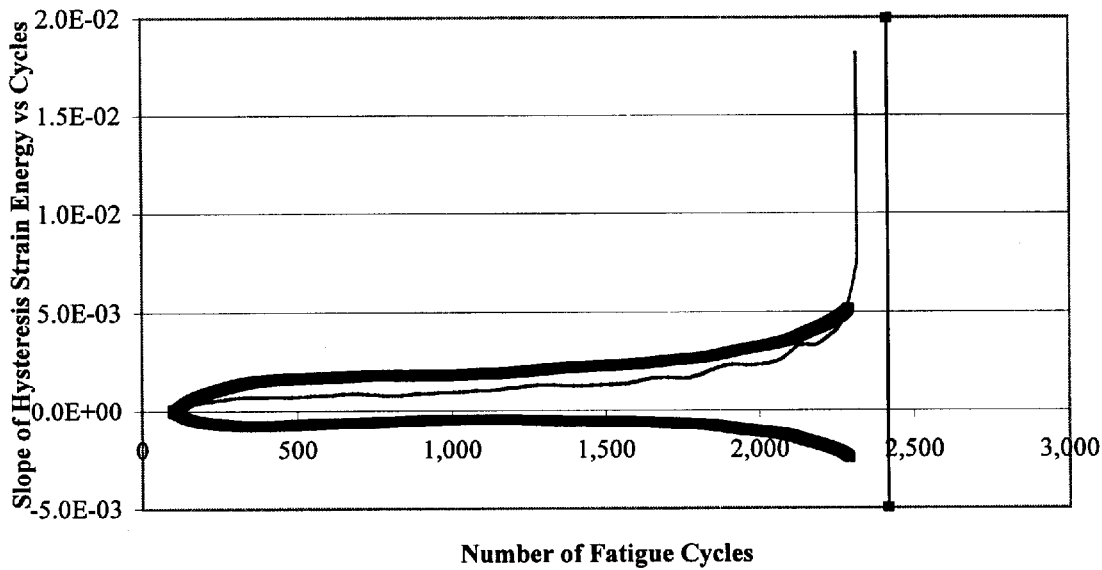
Figure 8C:
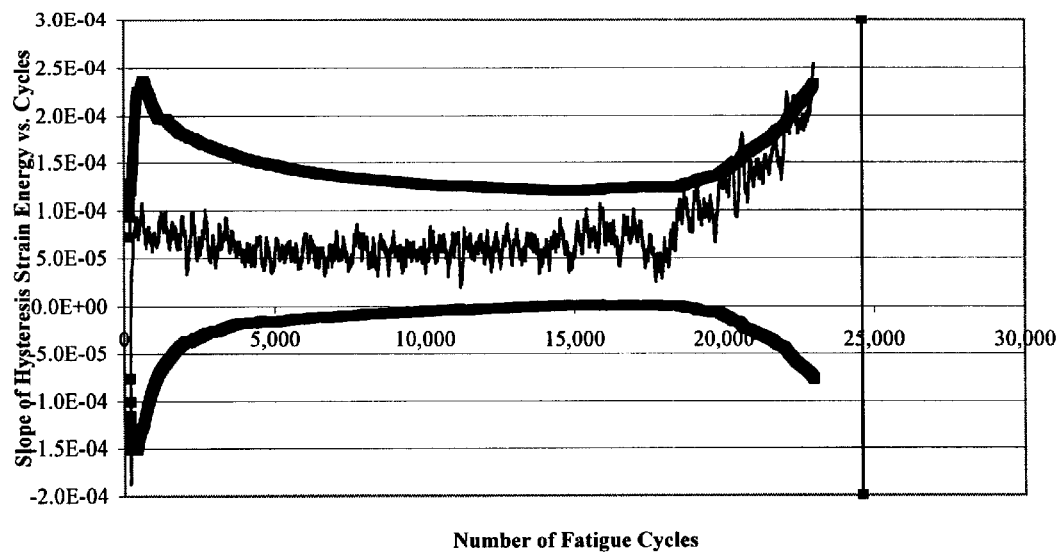
Figure 8D:
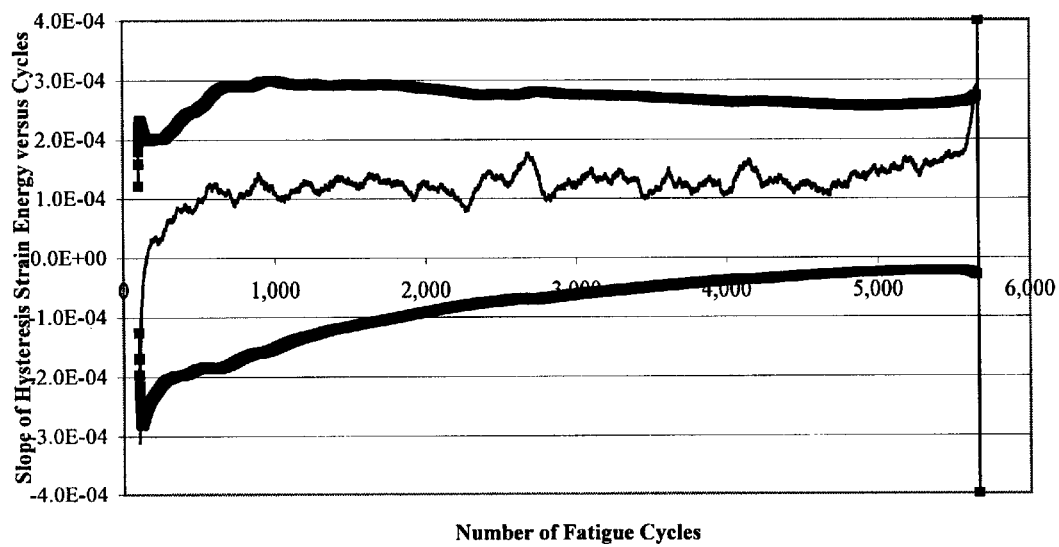
Figure 9A:
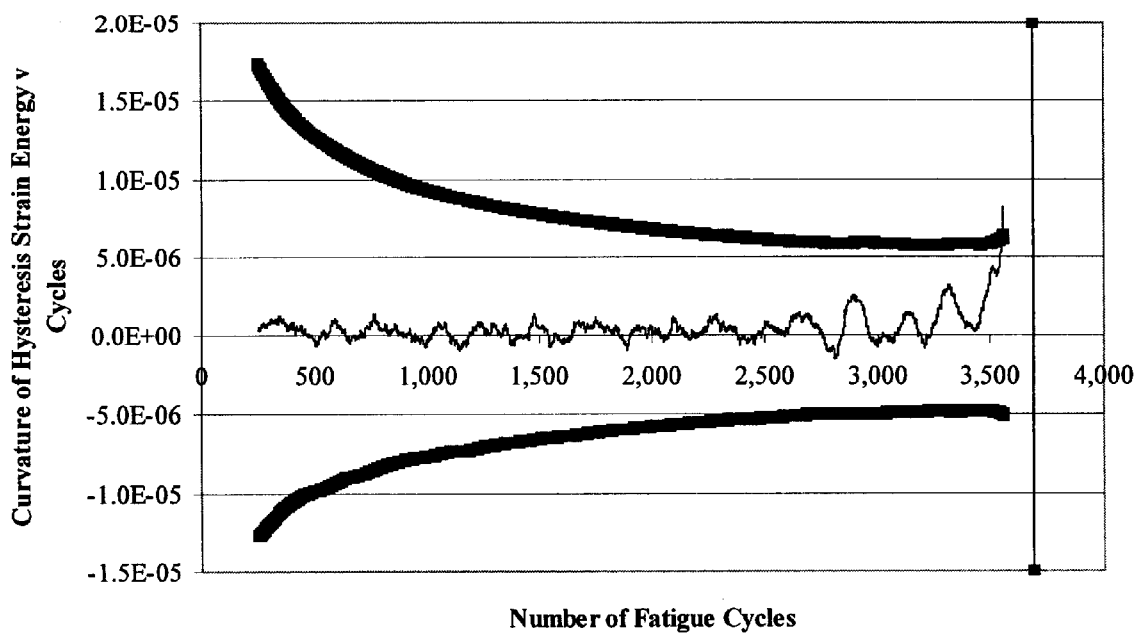
FIG. 9 shows graphs of the curvature of hysteresis strain energy curves for the respective graphs in FIG. 3, with upper and lower control limits.
Figure 9B:
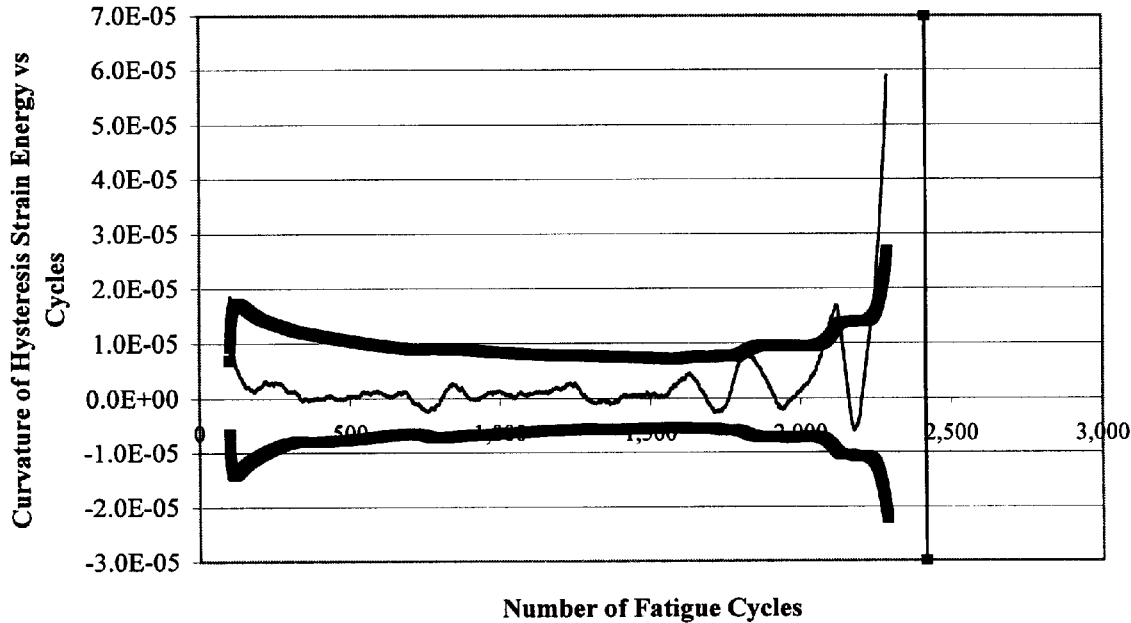
Figure 9C:
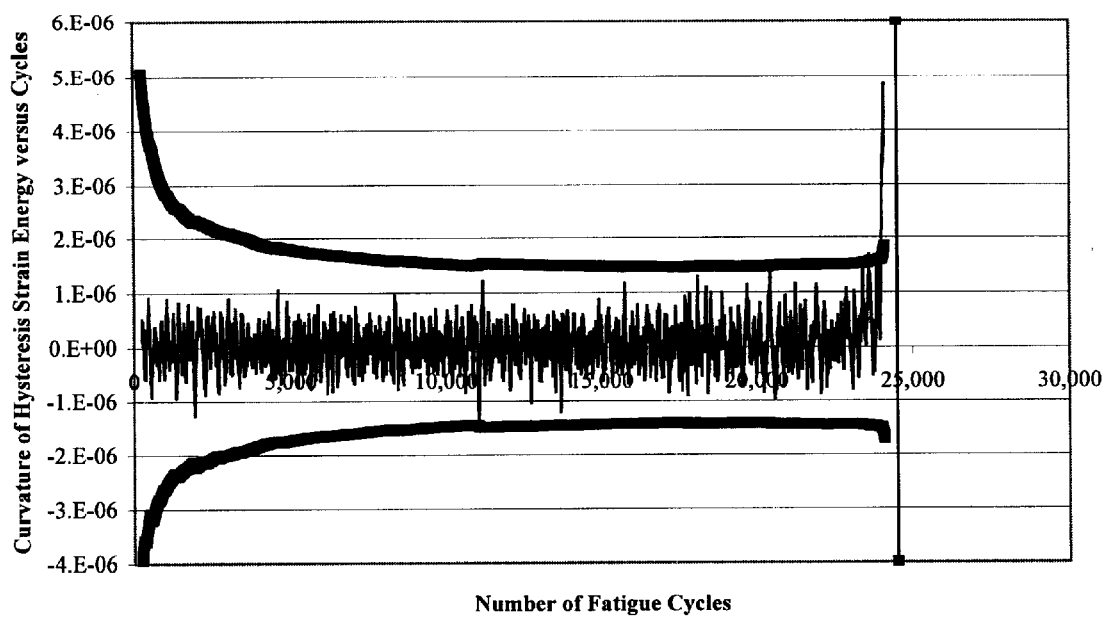
Figure 9D:
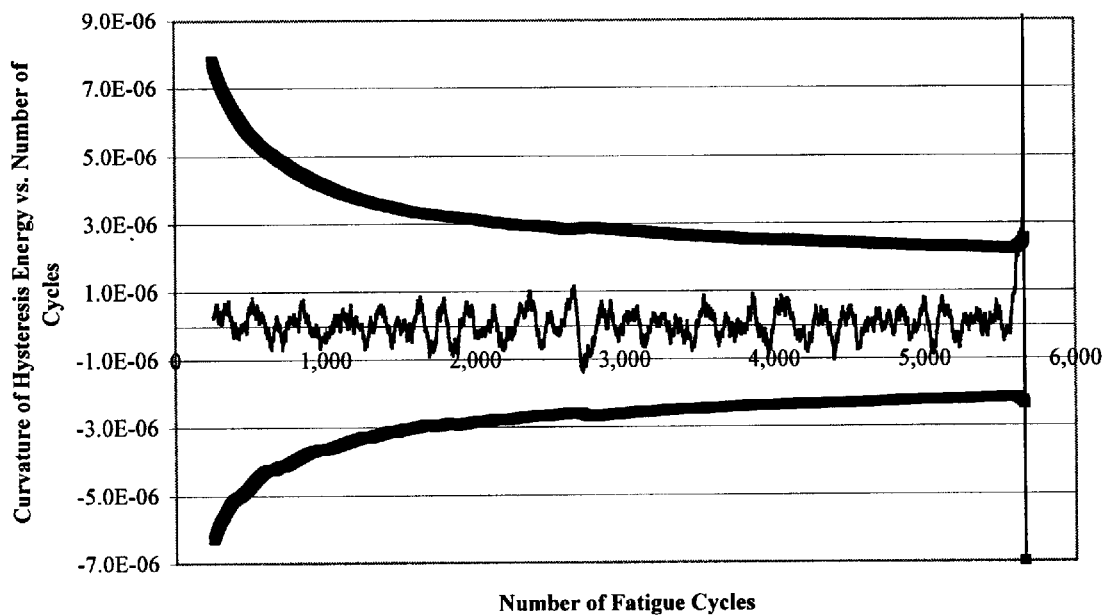

The HSE, E, is a function of the number N of applied loading cycles and is variable as shown in FIG. 3, which depicts LHSE for an experimental sample. LHSE, as well as other load- and strain-related data, depends on load amplitude and the material. The noise tends to mask trends in HSE that would indicate, for example, the onset of final stage unstable crack growth. When the noise level is high, E alone, or local trends therein, cannot be used to detect the imminent onset of failure.

To overcome the masking of trends by noise, smooth trends are extracted with a novel, zero-phase, quadratic filter as is set forth in U.S. Pat. No. 5,626,145 to Clapp et al., assigned to the assignee of the current invention, incorporated herein by reference. This filter uses a moving window of 2w+1 points of E(N) data, with the same number of data samples w on either side of the central point. The trend y at the central point of this window is estimated from a quadratic regression of the 2w+1 points. Adequate smoothing is achieved with a window width of 2w=about 5% of the total number of loading cycles. The trend then has the form $$y(z)=az^2+bz+c. \quad \text{(Equation 5)}$$

In Equation 5, z=N−n, where n is the fixed value of the number of loading cycles associated with the central point in the filter window. The corresponding value of y(z) at the central point of the window is $$y(z=0)=c. \quad \text{(Equation 6)}$$

By applying this zero-phase, nonlinear filter to the HSE curve, a smoothed HSE curve is obtained. Low-amplitude noise resulting from other forms of energy consumption is reduced, and the smoothed HSE curve more clearly reflects trends relating to crack-growth rate.

The foregoing filtering and fitting, with the necessary derivations, are accomplished by a processor receiving as input the values for the HSE curve. As with the other processors used in the method and apparatus of the invention, the processor performing the foregoing functions may be dedicated circuitry or may be a programmed general purpose processor. Also as stated above, the processor for the extraction of trends from the HSE curve may be a separate unit operatively connected to other processors, or all of the processors may be integrated into or as a single unit.

The typical crack growth rate curve as shown in FIG. 2 for a metal shows an initial trend. The growth rate then enters a region of fairly steady state, stable subcritical crack growth. The curve then enters a third distinct stage, indicating unstable final stage crack growth. Entry into this third stage is taken as the detection of the imminent end of life for the structural element. Thus, the crack growth rate curve itself can be used as an indicator function for impending failure. The HSE curve represents energy consumption due to crack growth, which superimposes on other modes of energy consumption, the final stages of which become noticeable when HSE due to crack growth becomes large enough to exceed the background damping level of energy consumption. This exceedance is observed as an excursion above or below the constant trend in HSE. The nonlinear filtering, such as that set forth above, is intended to extract from the HSE curve the crack-growth rate function free of the noise created by other forms of energy consumption and the inherent noise in sensor data.

Even after smoothing, however, the HSE curve may be too noisy to be a reliable indicator. While it is within the scope of the invention to use the HSE curve itself as an indicator function, it has been found that the slope, curvature, or both of the HSE curve values provide a highly reliable indicator function for indicating end-stage crack growth. The slope and curvature values can be derived from the smoothed HSE curve after filtration as set forth above. The slope at the central point of the moving window is $$y'(z=0)=b. \quad \text{(Equation 7)}$$

The second derivative at the central point of the window is $$y''(z=0)=2a. \quad \text{(Equation 8)}$$

The curvature of the curve y(z) is defined as $$\kappa=y''/[1+(y')^2]^{3/2}=2a/[1+b^2]^{3/2} \quad \text{(Equation 9)}$$

Even with the smoothing and filtering step described, however, the slope and curvature values derived for the HSE curve still exhibit low-amplitude variation. This variation can still tend to mask the trends in crack growth, as measured by the trends in the HSE curve. In certain applications, depending on the structure in question, the filtering step may be repeated. Too many repetitions, however, will of course smooth the very trends being sought.

In a preferred mode of the method, therefore, a subsequent processing step, therefore, is undertaken to distinguish random variations in the HSE curve, and the values for the curvature and slope thereof, from the systematic trend toward unstable final stage crack growth, the latter being the indication used to detect failure onset. This step encompasses establishing one or more limit values or limit functions. A further processing step is undertaken to derive the desired limit functions.

The limit functions are calculated by treating the values of the slope and curvature functions as statistical variables. This step is similar to that for which an industrial process control chart is constructed. The step begins with deriving x denoting the sample mean, computed from the beginning of the data to the current cycle. This value is $$x=\Sigma x_i/N \; i=1, N. \quad \text{(Equation 10)}$$

The corresponding standard deviation estimate s is then obtained from $$s^2=\Sigma(x_i-\underline{x})^2/(N-1) \; i=1, N. \quad \text{(Equation 11)}$$

Using these calculated values, one or more limit functions can be calculated for comparison with the selected indicator function. In a preferred mode of the invention, both an upper control limit function (UCL) and a lower control limit function (LCL) are calculated. Preferred values for these functions are $$UCL=x+4s \quad \text{(Equation 12)}$$

$$LCL=x-4s. \quad \text{(Equation 13)}$$

Using these values, the UCL and LCL, or either, can be plotted as limit functions for comparison to the selected indicator function. According to the method of the invention, the indication of failure onset for the structural member is then the point at which the indicator function, preferably the slope or curvature functions or both, exceeds the UCL positively or the LCL negatively. The detection of imminent failure can be set as this point of exceeding, the point of intersection of the indicator and limit functions, or a defined point of approach of the indicator and limit function curves. Any of these points, generally referred to herein as the convergence of these functions, can be selected as the indication of failure onset.

The selection of the multiple for the standard deviation value s will depend on the material, the environment, the desired safety factor, and other considerations. The multiplier of 4 used above will establish limits wherein the probability of Gaussian random data exceeding one or the other of the limits corresponds to a false positive probability of 1 part in 31,574 measurements. The multiple can be adjusted to give the desired probability of false positive or negative indications based on the expected number of cycles or intervals to failure. The multiplier for the UCL and LCL may be the same or different.

Other variations are also possible. For example, the window 2w+1 used in the filtering and fitting step may be narrowed or broadened. A narrower window will allow the detection and monitoring of local events. These events may be of interest in certain research applications or where safety concerns are high enough. A narrower window will lessen the smoothing function, and may mask the onset of trends. A broader window, on the other hand, may be desired where local phenomena are of little concern. This greater smoothing, however, may also affect the detection of trends by smoothing and thus effectively eliminating the early indications of trend changes. Experimental work indicates that the 5% of useful life window generally avoids both of these possible problems.

The method of the invention thus encompasses the calculation of this limit function(s) and the monitoring of the limit and indicator functions. When these functions converge, an indication is provided in the form of an output signal. The output signal may be of any desired form. The output may, for example, trigger an alerting mechanism such as an indicator light, an audible warning, or the like. Alternatively, the output may be simply graphic or numeric in form, providing data from which a decision on continued use of the element may be based.

The HSE curve itself can be used as the indicator function for any of the three defined classes of crack growth, that is, fatigue and corrosion fatigue crack growth, creep crack growth, and stress corrosion crack growth. Because of the low-amplitude noise, as mentioned, the detectable trends in this curve do not always provide a reliable indicator of the final-stage trend. Deriving the slope and/or curvature functions, as shown, provide better indicator functions. The choice of which indicator functions, or which combinations thereof, to use as the primary indicator function will depend on factors such as the material, the environment, and the type of structural element.

Each derivative of the initial HSE curve increases the effect of the noise in the HSE curve. Therefore, in some applications, it may be useful when calculating the slope and curvature functions to use the quadratic filter described above to smooth these derived curves. Even when these functions are smoothed, some noise remains. Thus, while monitoring these functions alone to detect the onset of final stage crack growth may suffice in some applications, it is preferred that the limit functions be established to provide a more accurate and reliable indication of this final stage.

The apparatus by which the method can be accomplished can vary widely. Many different types of sensors can be used to measure load, strain, and displacement in critical areas of the structure. These sensors may be associated with, adhered to, or embedded in the structure. The output of the sensors may be stored for periodic evaluation, or may be processed and monitored in real time. The clock necessary to determine load cycles and time intervals is also well-known. Also as described, the processors used to integrate the raw physical data, associate the calculated HSE and assign each value to the appropriate cycle or interval, to calculate HSE as a function of the number of load cycles or time intervals and derive the indicator and limit functions and, finally, to compare the indicator and limit functions to provide an indication output may be separate interconnected units or a single integrated processor. Last, the indication responsive to the output may be any audio or visual device, or a graphical or numerical display.

The foregoing description used fatigue and corrosion fatigue crack growth as an example, where the crack growth is monitored by measuring and calculating LHSE. The description applies equally to monitoring crack growth where creep or stress corrosion effects predominate. For each of these, the sensors provide load and/or strain data, which is then plotted as a function of time. The load and strain data is integrated over the selected time interval to measure the change in energy over the time interval. The change in energy is a measure of the crack growth. For each of creep and corrosion fatigue, the energy absorbed by crack growth is calculated as $$\Sigma \int P(t) d\delta(t), \qquad \text{(Equation 14)}$$

where the summation is from i=0 to n, and the integral is from $t=t_i$ to $t=t_{i+1}$. For each selected time interval, the load- and strain-related data are integrated over $t_i$ to $t_{i+1}$, and the result is the HSE value which is appropriately plotted as a function of time.

Having calculated the value of HSE, as used herein, for creep crack growth rate, it is preferred to express it as a logarithmic function of time. The curve thus plotted shows the same trilinear curve as the typical crack growth rate curve for metals. This clearly indicates the change in trends. In the case of creep crack growth, there are not the competing mechanisms of damping found in fatigue crack growth to mask the lower portions of the creep crack growth rate curve. Thus, the creep crack growth rate curve exhibits an appearance similar to the full fatigue crack growth rate curve for metals.

For stress corrosion, it is preferred to express the HSE values as a linear function of time. For stress corrosion, this will also assume the trilinear form of the typical curve. Applying the nonlinear filter will clarify even further the resulting function, making detection of the end-stage crack growth a reliable indicator of imminent failure.

The relevant processors may be programmed to plot in any desired fashion, so long as the trends are clear and ascertainable as described above. A given structural element will likely be subject to both creep and stress corrosion effects, with one or the other predominating during differing periods in the life of the member. In utilizing the method and apparatus of the invention in such situations, the HSE (actually, the changes to stored strain energy) can be plotted as a function of both logarithmic and linear time, with appropriate monitoring of the trends, such as by limit controls. The output signal as an indication of imminent failure would then be set to be given when the trend is detected on either the logarithmic or linear scales. When using control limit functions, the indicator is the convergence of either slope or curvature of either the logarithmic or linear plot with the appropriate limit function.

Several tests were conducted to illustrate the use of the foregoing methodology. In each of the following, the various steps used in deriving HSE values, indicator functions and limit functions are as described above.

EXAMPLE I

Four coupons of randomly oriented fiber-reinforced plastic were tested. The coupons were nominally ⅛ inch thick and were machined to a reduced cross-sectional shape with a 1.6 inch gage section for a 1.0 inch extensometer.

Three data variables were recorded: displacement of the loading grips, tensile load, and tensile strain in the reduced section as measured by the extensometer. Loading was performed at room temperature on a servohydraulic test machine having a 10,000 pound capacity. The fatigue loading frequency was 10 Hz. Data were recorded by a National Instruments PCI 16XE-50 General Purpose I/O System of 16-bit resolution. The data recording frequency was 2,000/ channel/second, producing about 200 measurements of each variable over each fatigue cycle. Load cell voltage variations were on the order of 0.1% (10 mV) of full scale (10 V), or 10.0 pounds. Measurement resolution was 1.0 pound in load measurement (about 10 psi) and 5 $\mu\epsilon$in strain measurement.

The fatigue test results for the four coupons, designated as P36-O-45, P36-O-46, P36-O-47, and P36-O-48, are shown in Table 1 in FIG. 4. The hysteresis strain energy data for the coupons was plotted as a function of the number of load cycles as shown in FIG. 5, wherein in each graph the point of failure is shown by the vertical bar. The data show that the initial hysteresis strain energy consumption per fatigue, or load, cycle was approximately 1.5 to 3.0 in-lb./in³. The energy consumption shows an initial sharp decrease, followed by a monotonic rise, and finally followed by a sudden rise near failure.

While these data do show an end-stage trend that can be used as an indication of imminent failure, a better indicator was sought. The curves were therefore subjected to the nonlinear, quadratic, zero-phase filter discussed above, and the slopes and curvatures for each initial curve in FIG. 5 were derived. Slope is shown in FIG. 6, and curvature in FIG. 7. Slope, for example, indicates how quickly the energy consumption is rising.

As is illustrated, the slope and curvature functions, used as indicator functions for the onset of the end-stage crack growth rate trend, provide more readily ascertainable indications of end-stage, unstable crack growth. As is set forth above, a more uniform method of detecting the desired trend involves the derivation of limit functions. The limit functions, calculated as shown, are chosen to minimize the occurrences of false positives and false negatives. FIG. 8 shows the smoothed slope of hysteresis strain energy versus the number of cycles, with upper and lower limit functions calculated point by point as the data progress. FIG. 9 shows similar graphs for the curvature of the hysteresis strain energy. It can be observed from these figures that the convergence of the slope and curvature functions converge with the limit functions in advance of the failure points. This convergence thus serves as a reliable indication of the onset of the end-stage trend presaging failure. The predictive capabilities thereof are shown in Table 2 of FIG. 10.

EXAMPLE II

Data were obtained for tensile load and tensile strain on ten aircraft aluminum coupons with expected fatigue lifetimes in the 10,000 to 100,000 cycle range. The hysteresis strain energy being consumed by the coupons was calculated, followed by nonlinear smoothing, the derivation of slope and curvature, and the calculation of upper and lower control limits as discussed.

The coupon material was unclad 2024-T3 aluminum alloy sheet, a material commonly used in aircraft skins. The coupons were modeled to the outer skin of the U.S. Air Force KC-135, having a nominal thickness of 0.090 inches. They were machined to an ASTM E466 standard fatigue specimen with reduced cross-sectional width, with a 1.3 inch long by 0.50 inch wide gage section for the 1-inch extensometer. The apparatus and procedures were as described in Example I, but data recording frequency was 4,000/ channels/second, producing about 400 measurements of each variable over each fatigue cycle.

Figure 11:
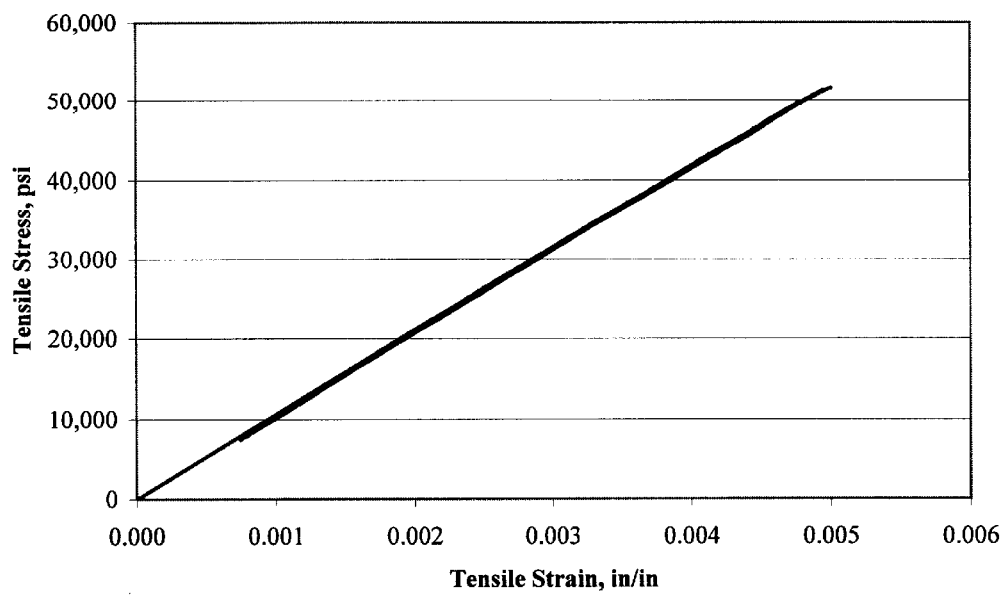
FIG. 11 illustrates an initial stress-strain curve for an aircraft aluminum test coupon subjected to tensile load and strain.
Figure 12:
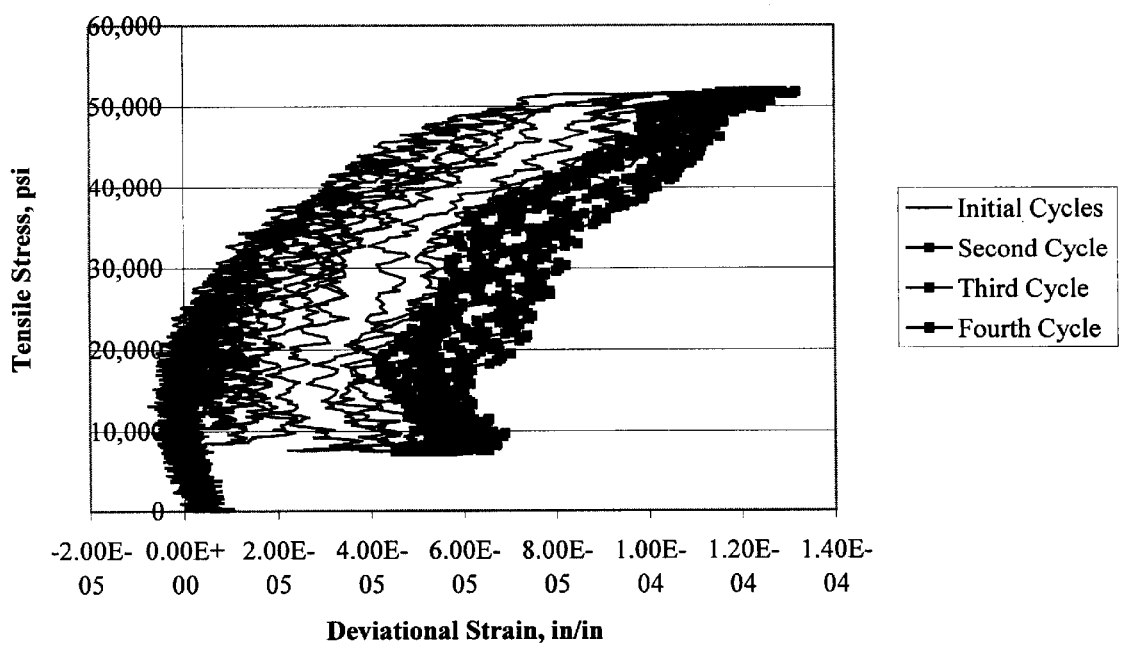
FIG. 12 is a plot of fatigue stress versus deviational strain for the sample used for FIG. 11.
Figure 14:
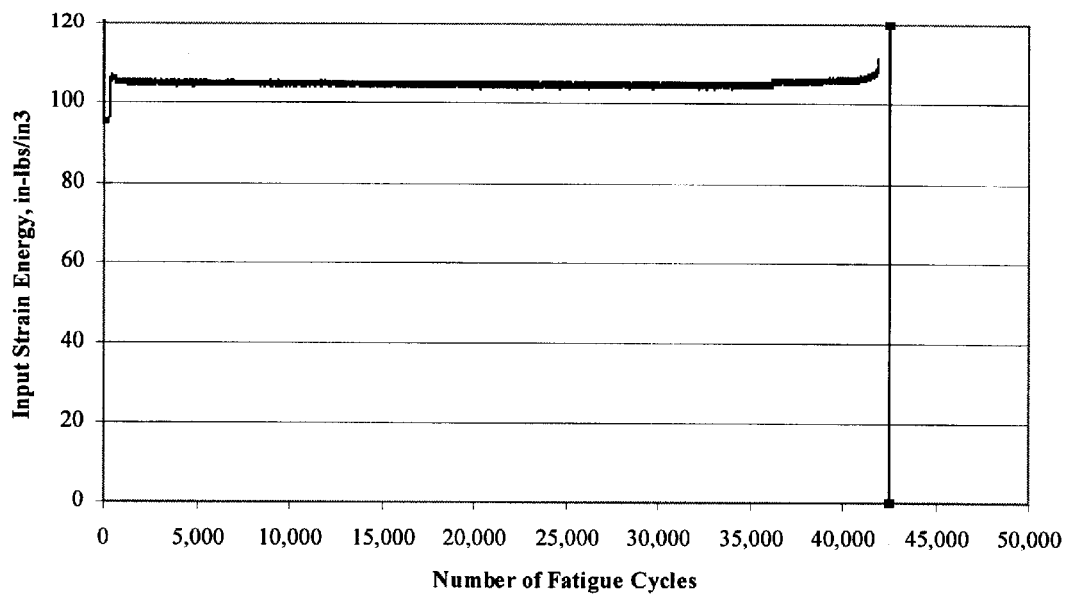
FIGS. 14–22 are graphs of the input strain energy for samples TM-2 to TM-10, respectively, discussed in Example II, below.
Figure 15:
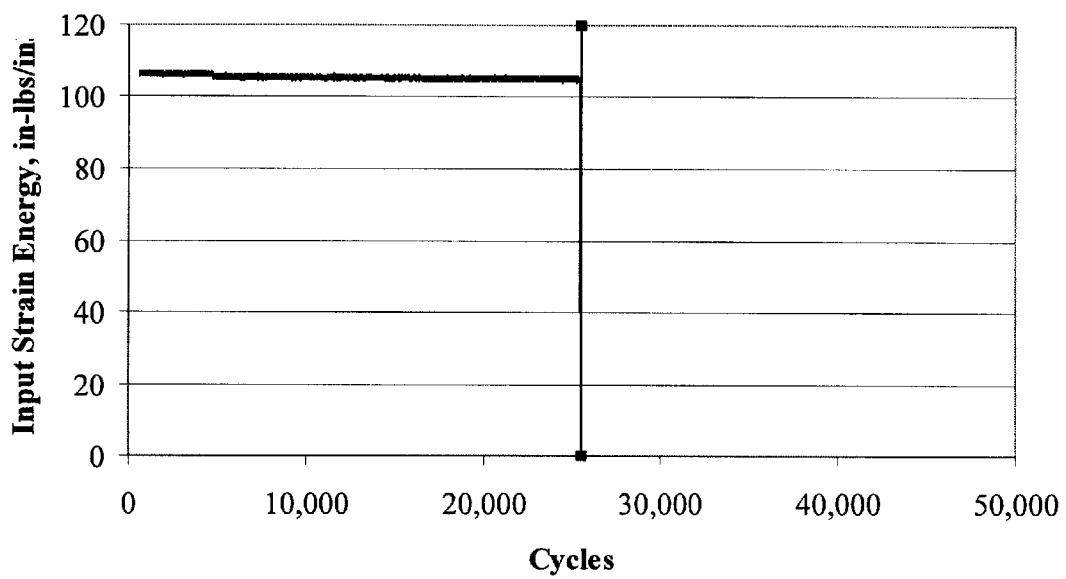
Figure 16:
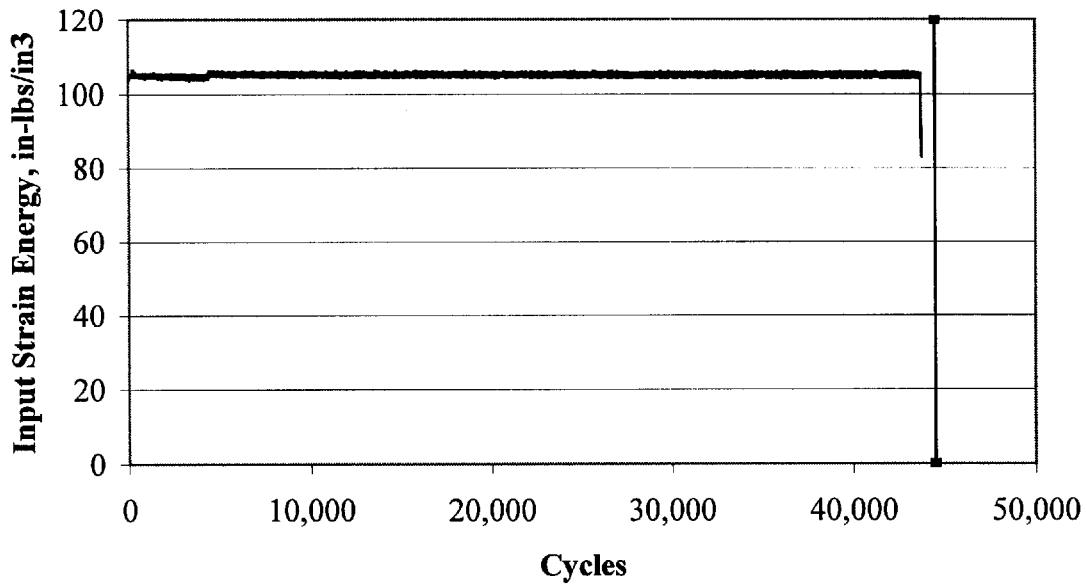
Figure 17:
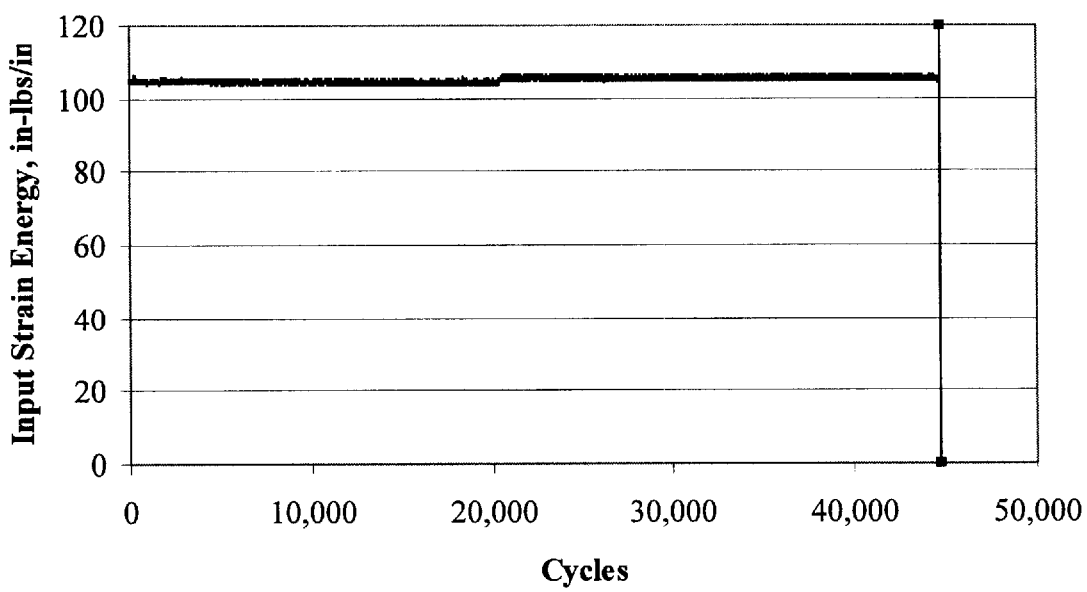
Figure 18:
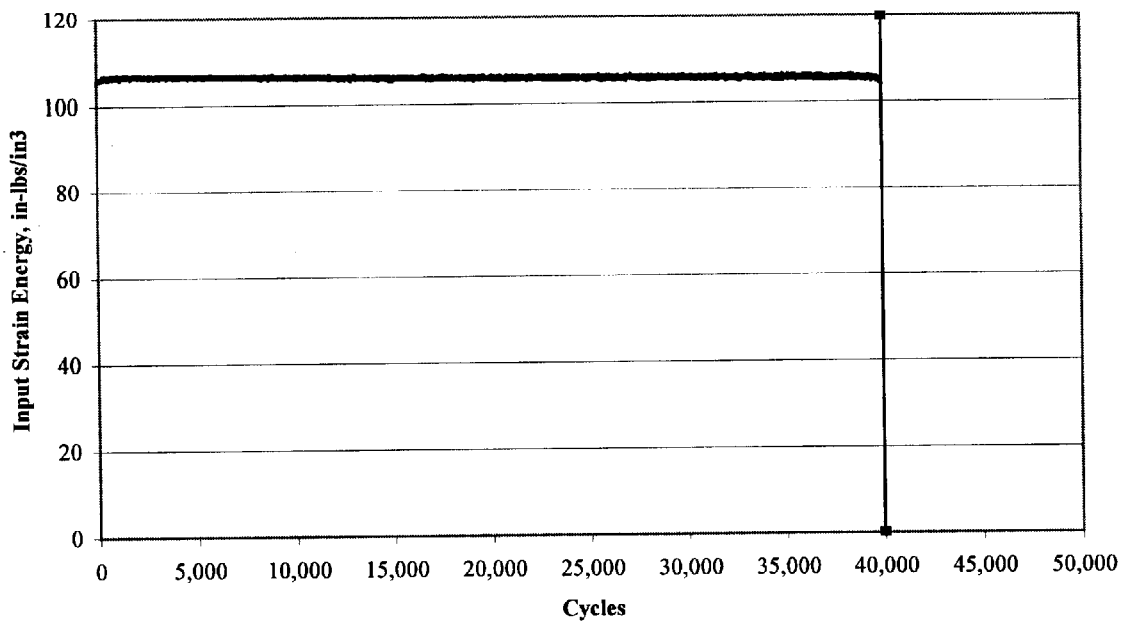
Figure 19:
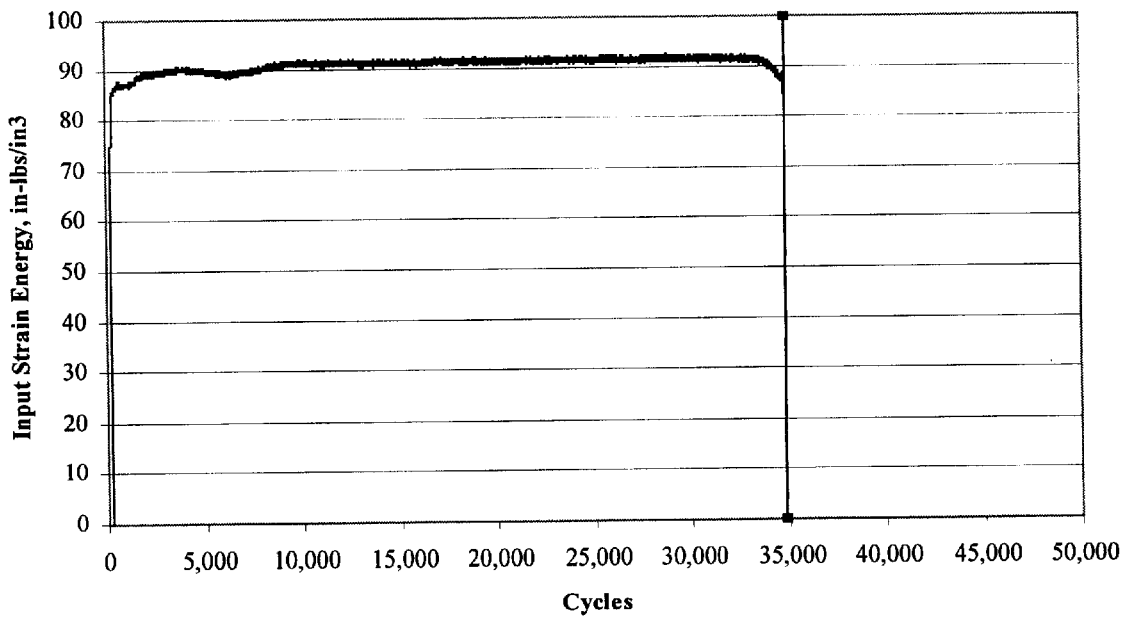
Figure 20:
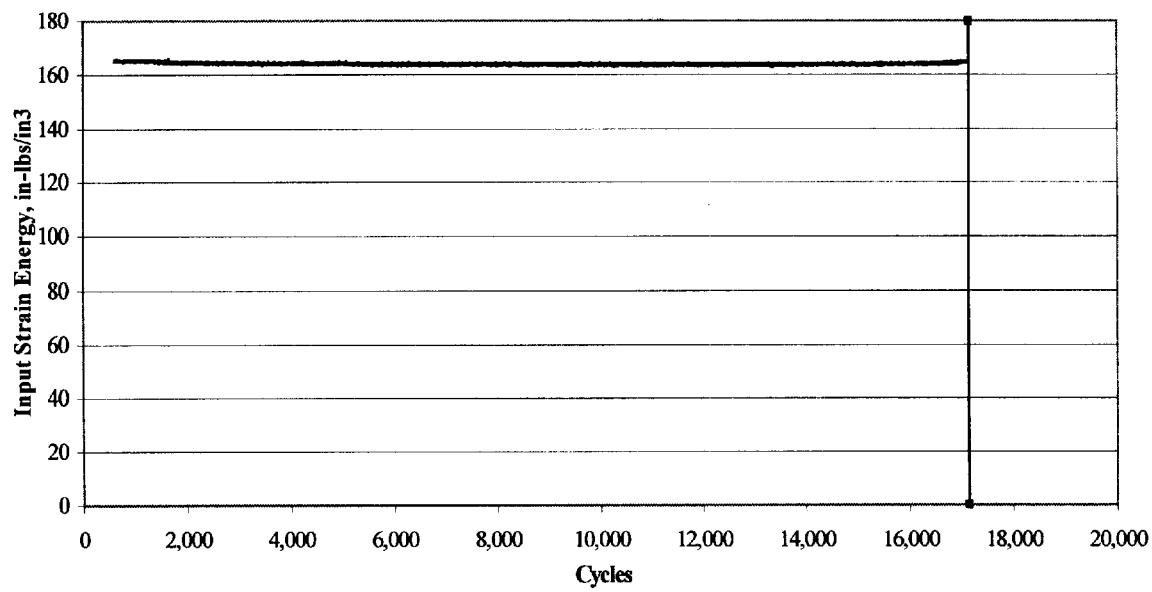
Figure 21:
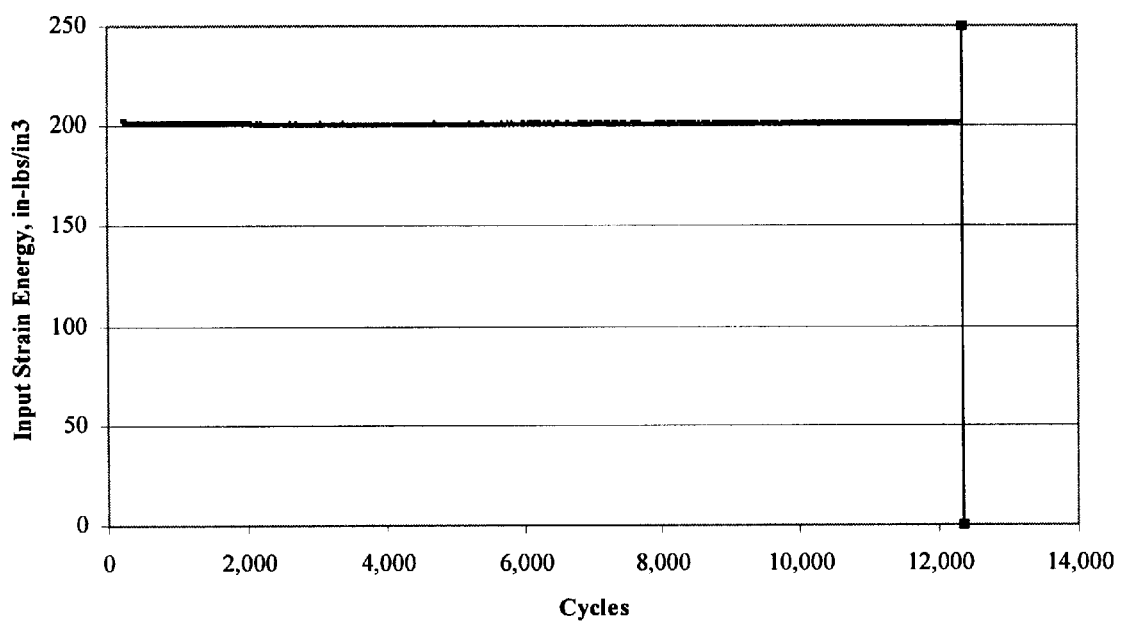
Figure 22:
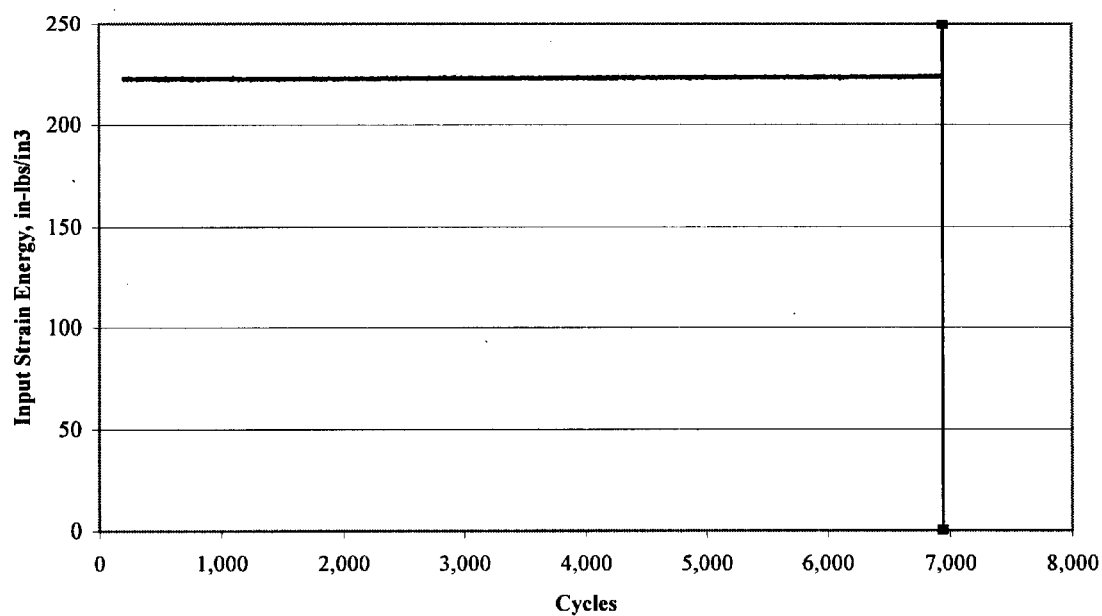
Figure 23:
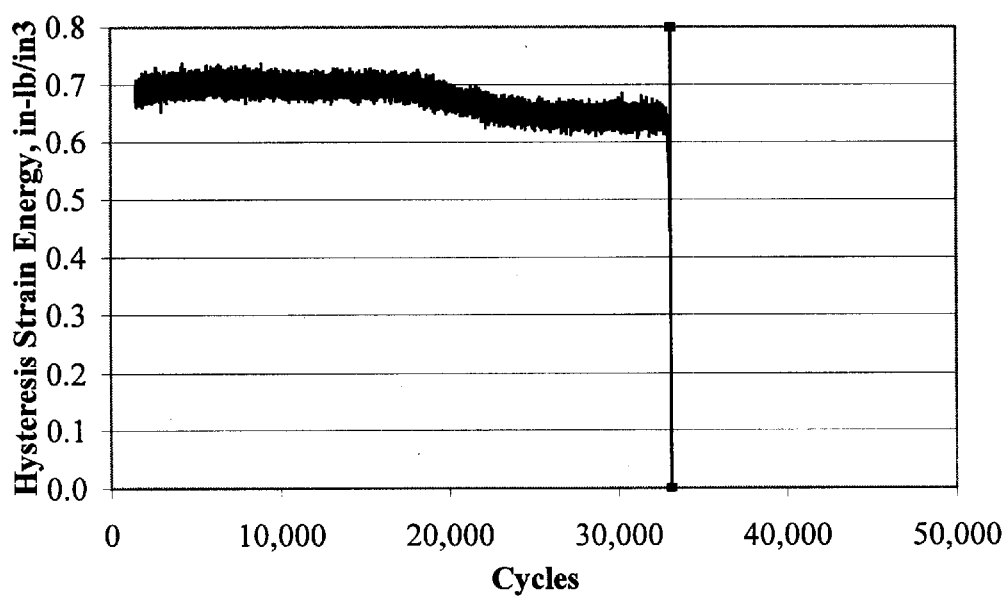
FIGS. 23–32 are graphs of the hysteresis strain energy per cycle versus the number of cycles for samples TM-1 to TM-10, respectively, discussed in Example II, below.
Figure 24:
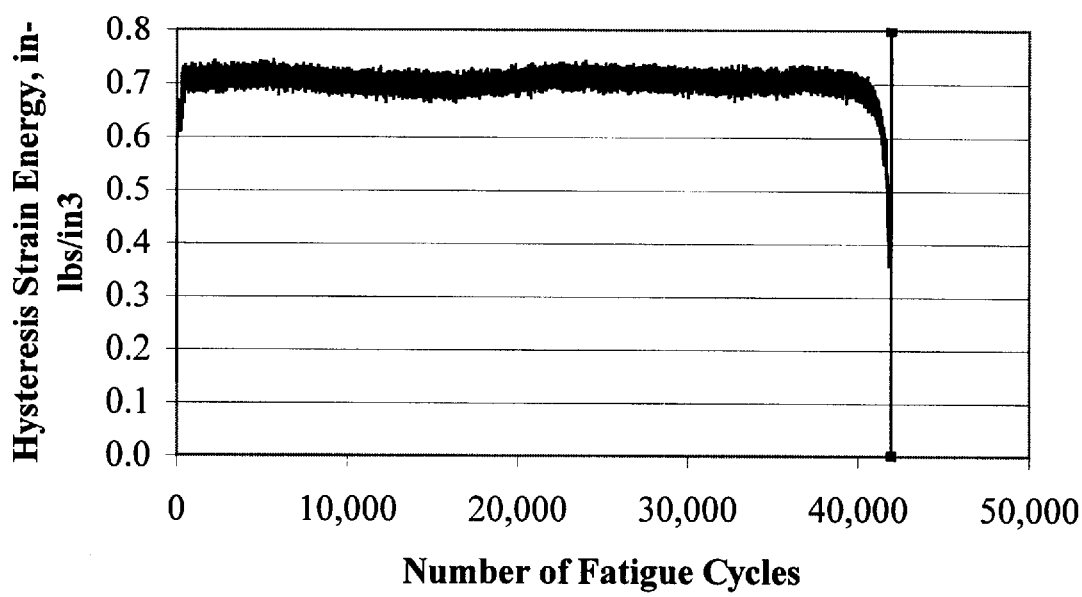
Figure 25:
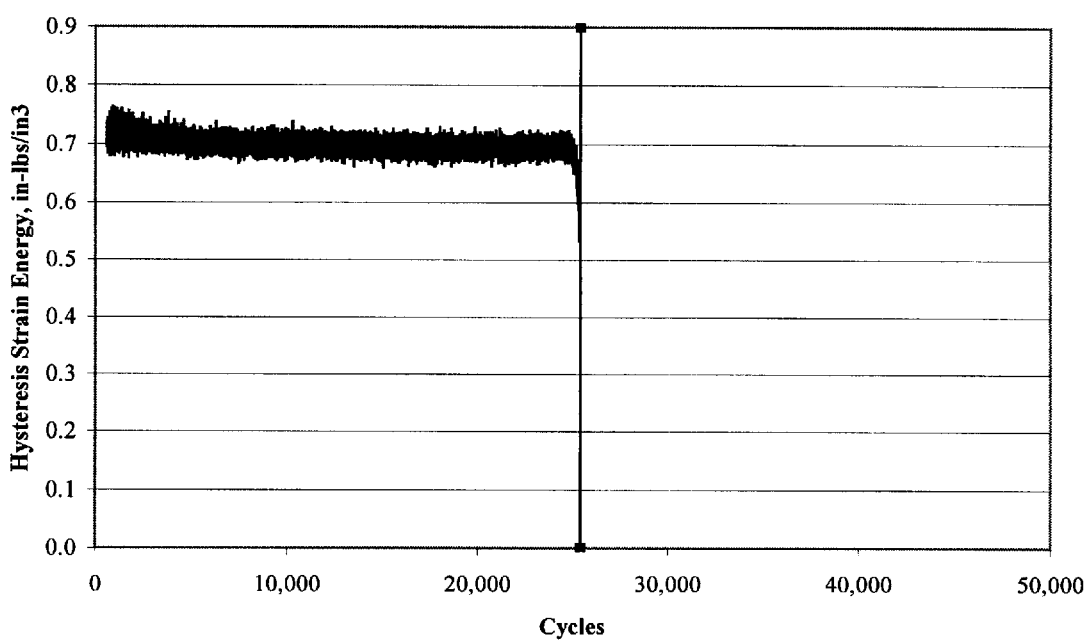
Figure 26:
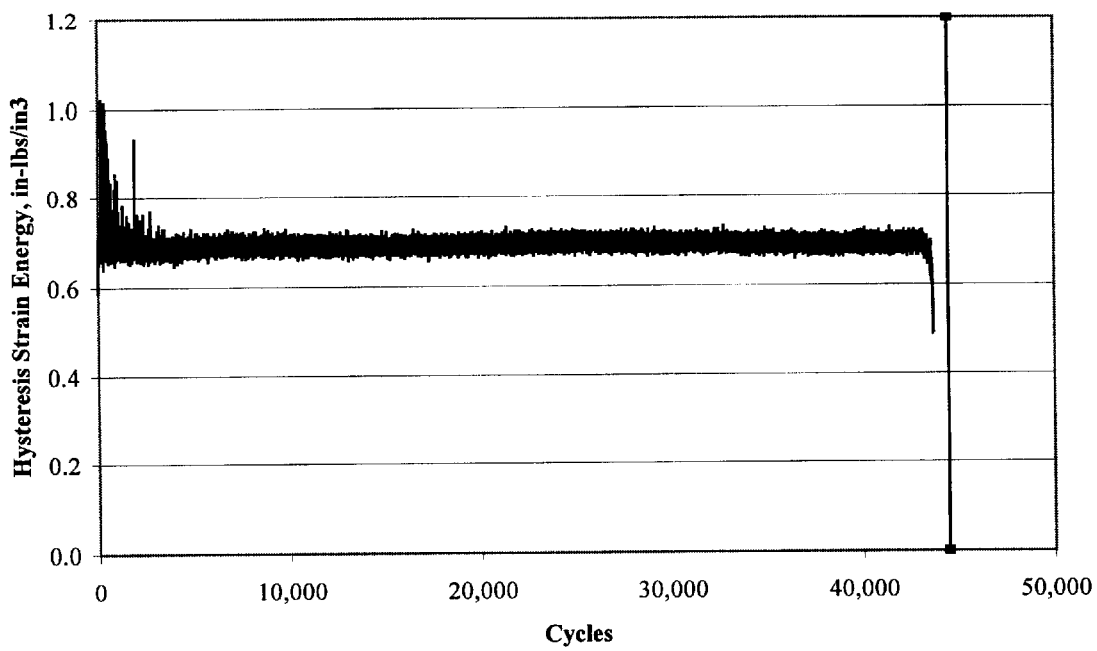
Figure 27:
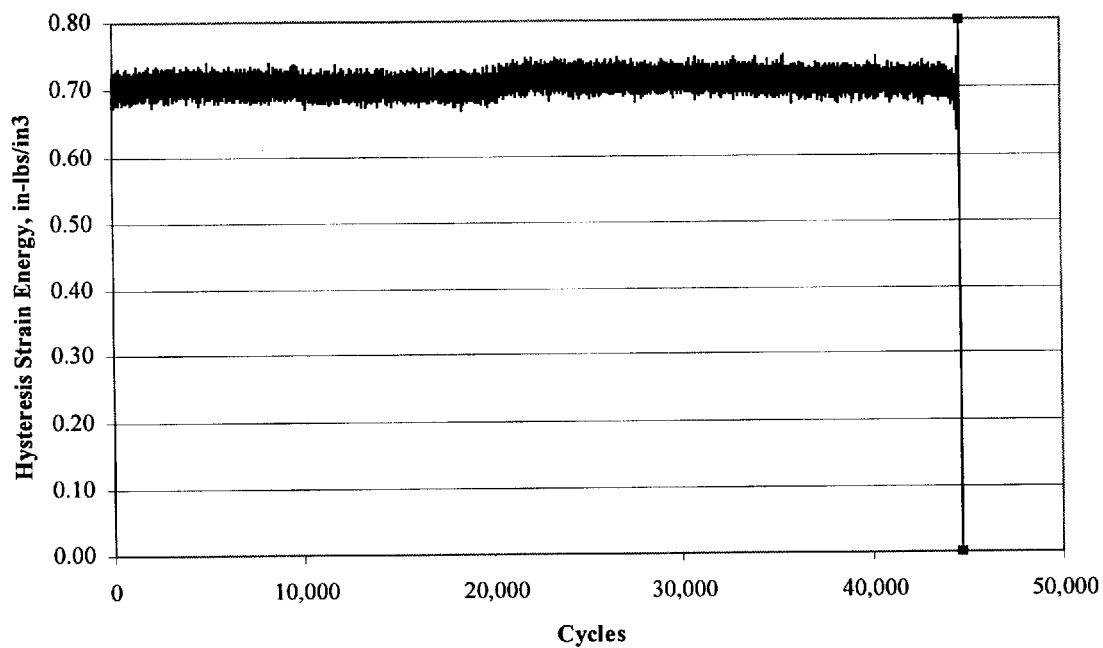
Figure 28:
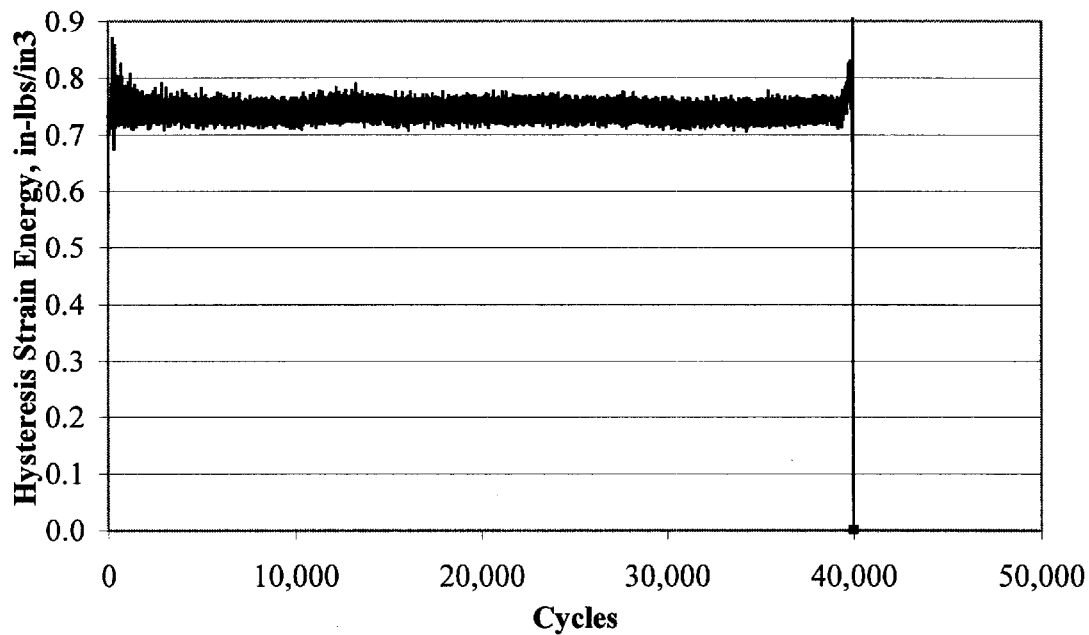
Figure 29:
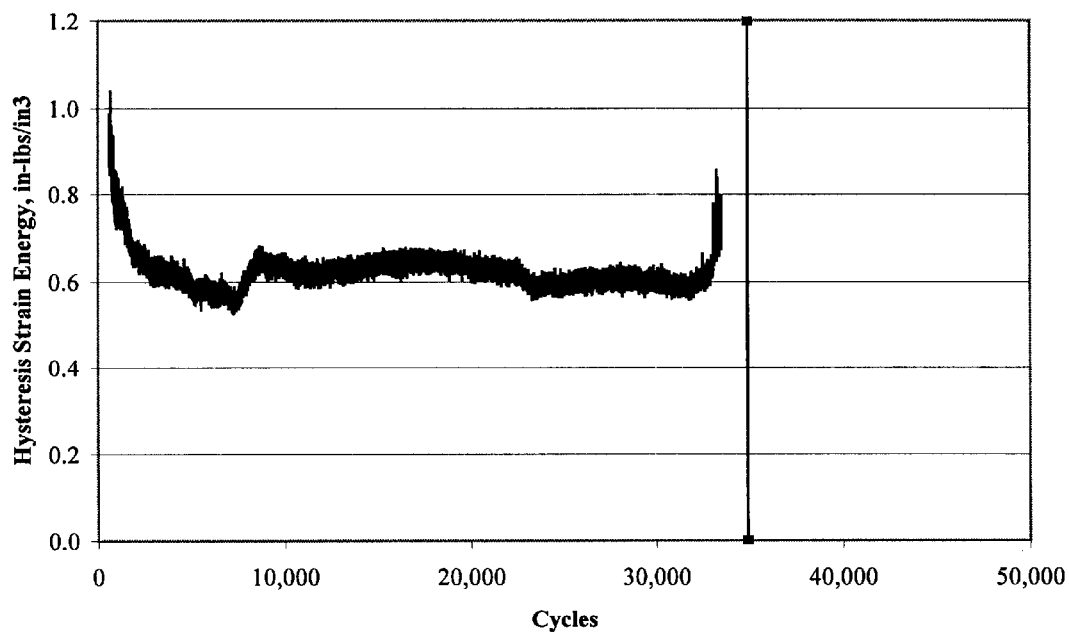
Figure 30:
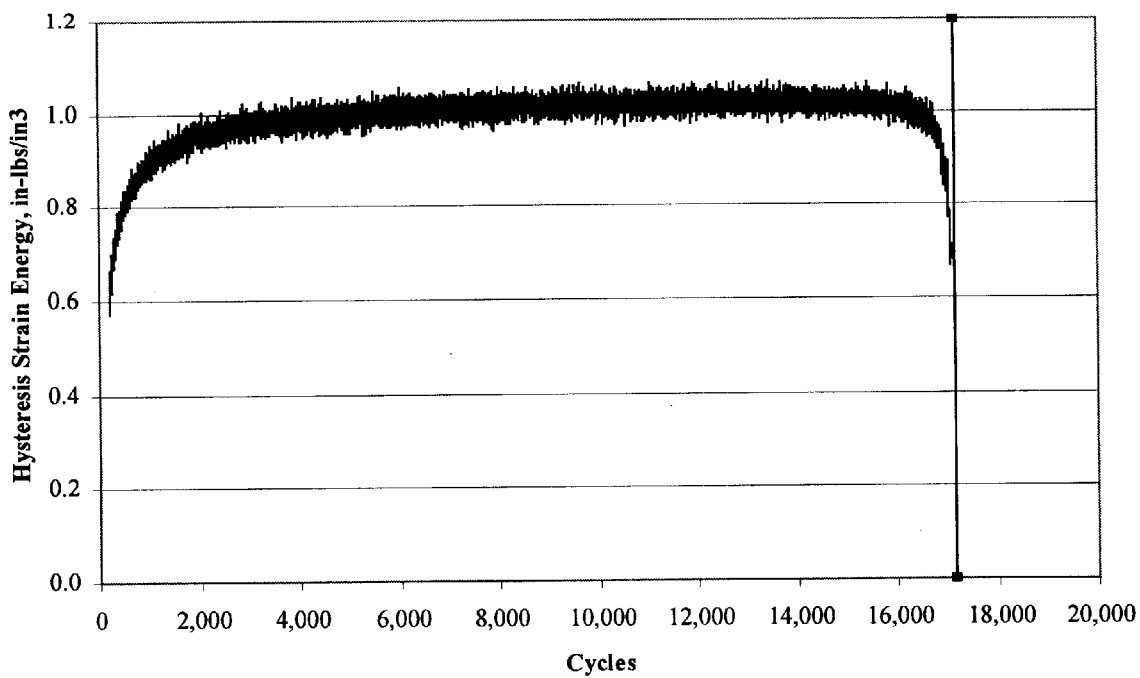
Figure 31:
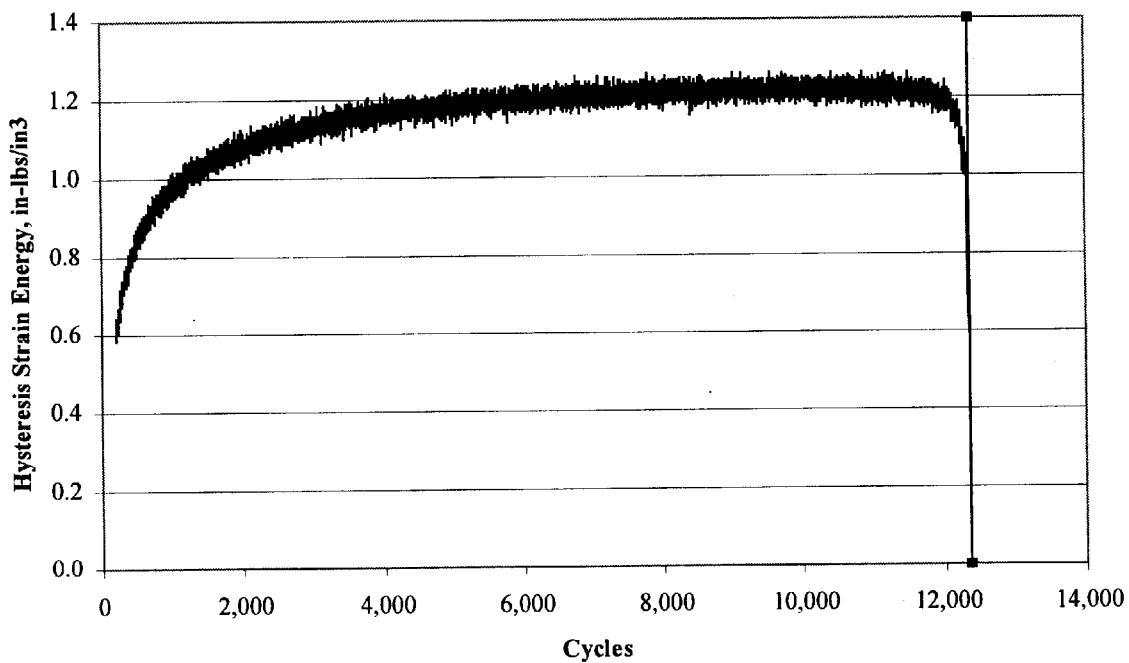
Figure 32:
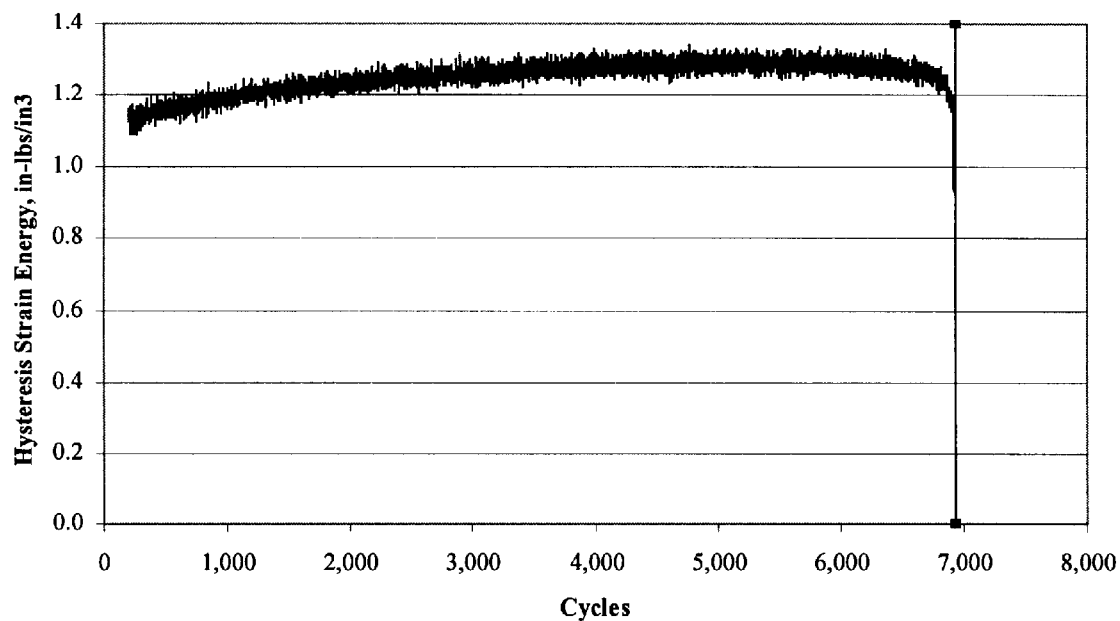
Figure 33:
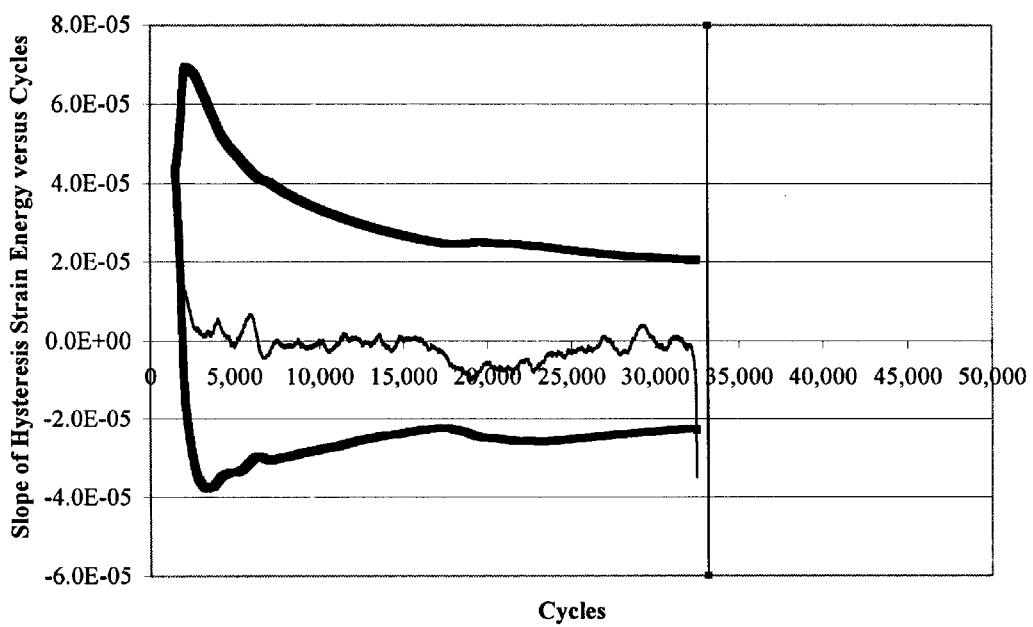
FIGS. 33–42 are graphs showing the slopes of the HSE curves of FIGS. 23–32 with upper and lower control limit functions, as discussed in Example II, below.
Figure 34:
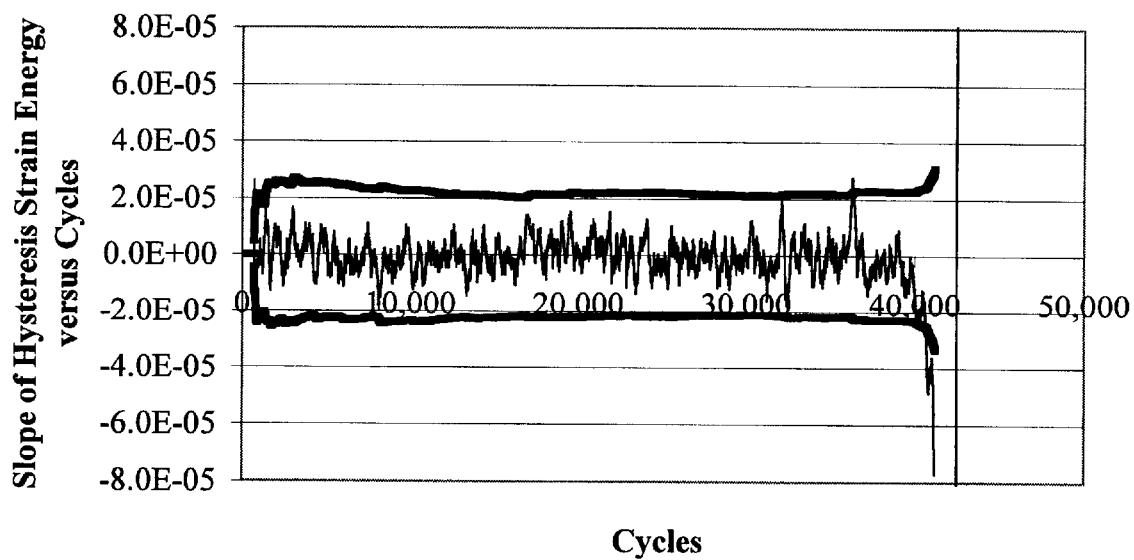
Figure 35:
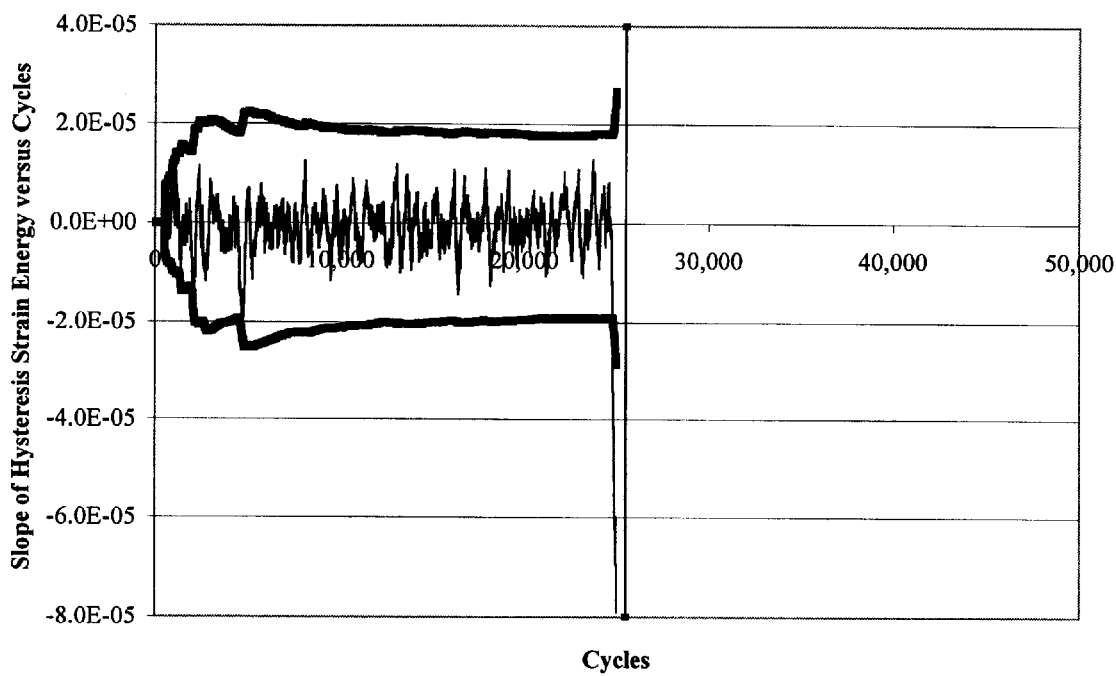
Figure 36:
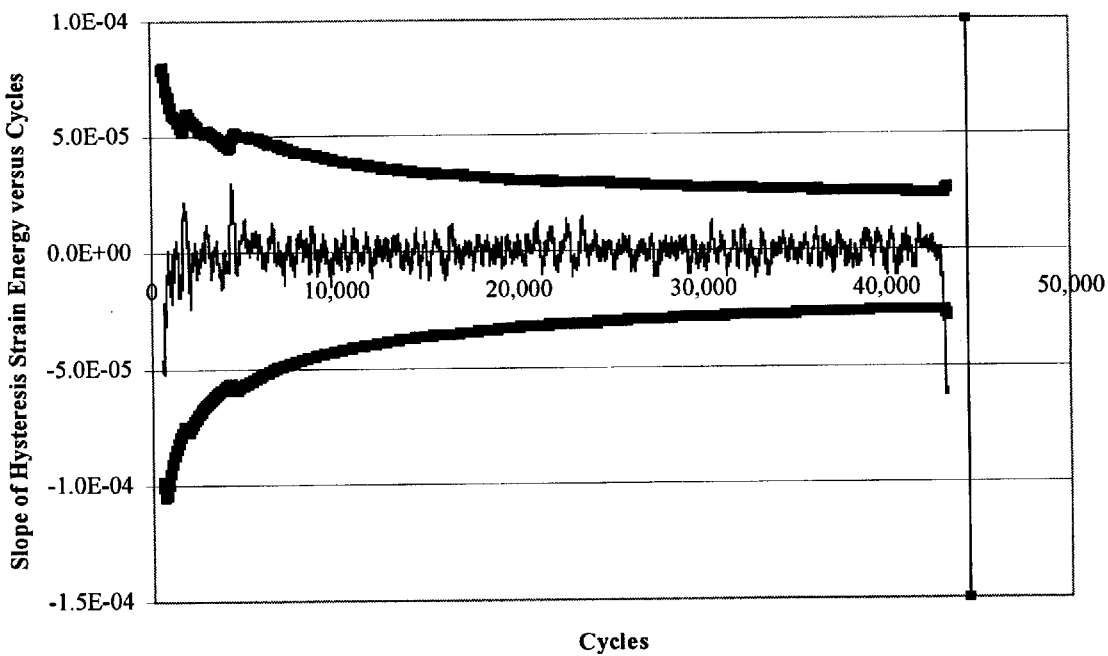

An initial stress-strain curve for a test sample of 2024-T3 aluminum is shown in FIG. 11. FIG. 12 illustrates the deviation from true linearity of the stress-strain response of this same sample on a cycle-by-cycle basis, illustrating the hysteresis strain energy phenomenon. Table 3, in FIG. 13 shows the fatigue data test results for the ten coupons in this example.

Figure 37:
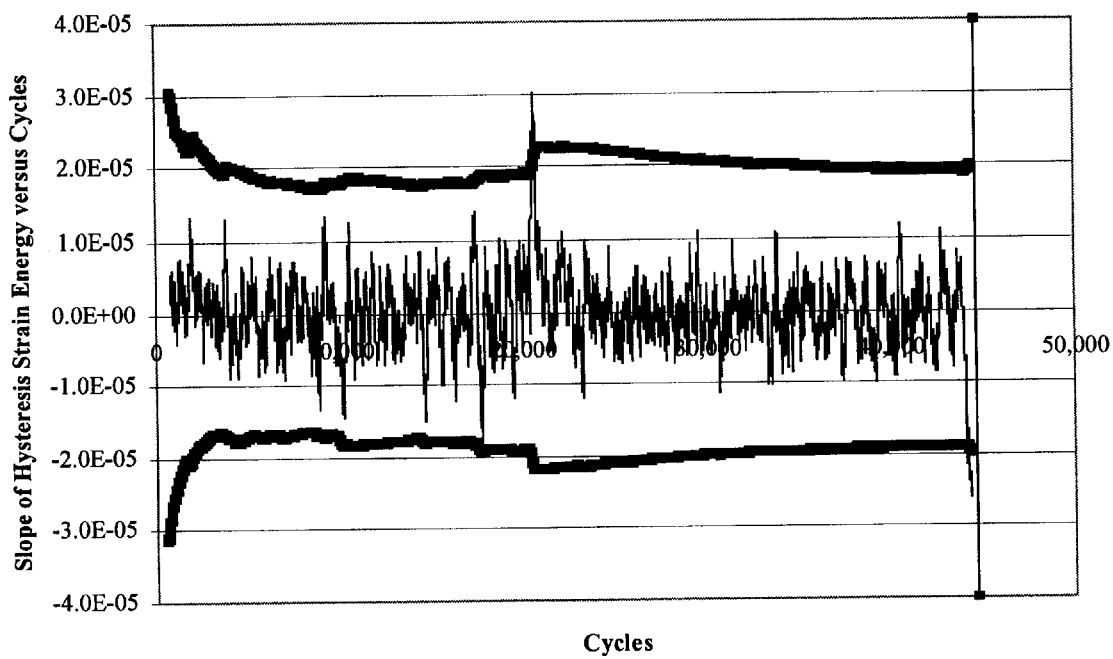
Figure 38:
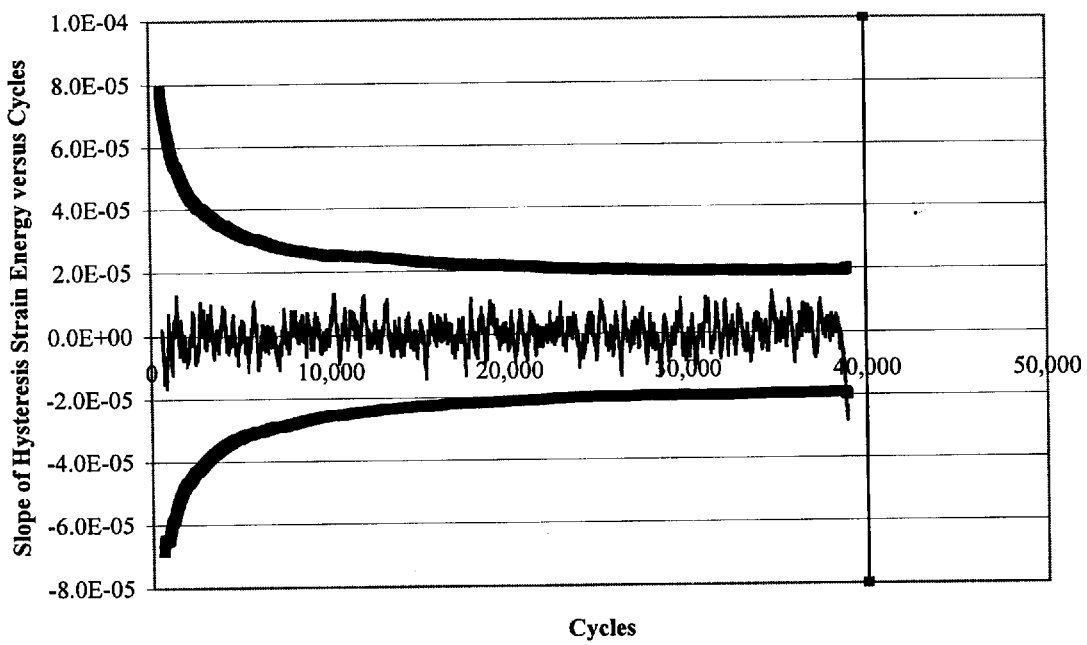
Figure 39:
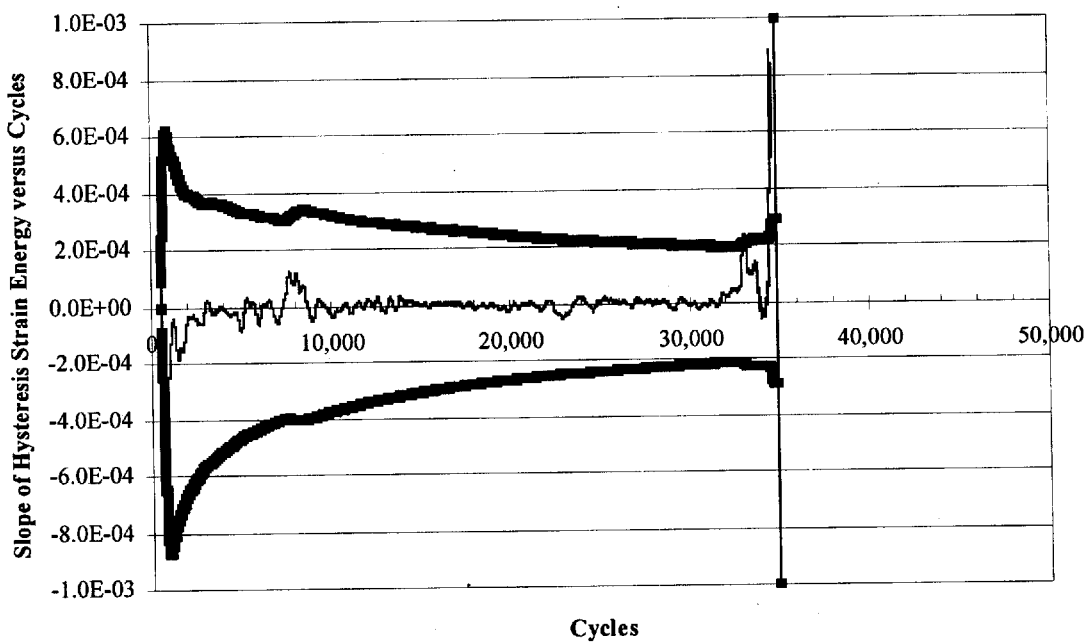
Figure 40:
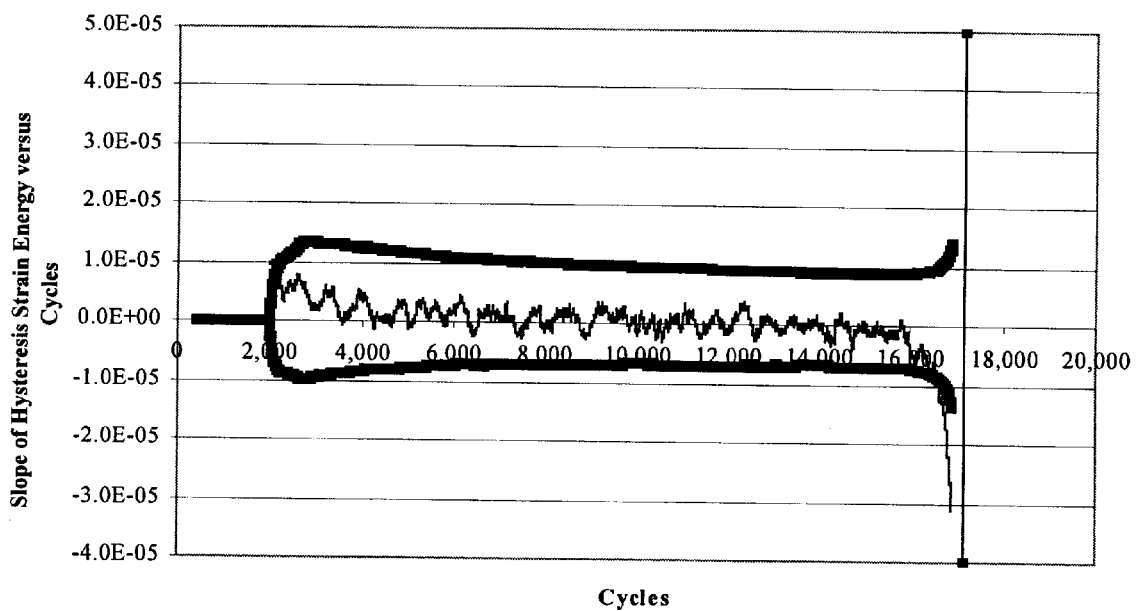
Figure 41:
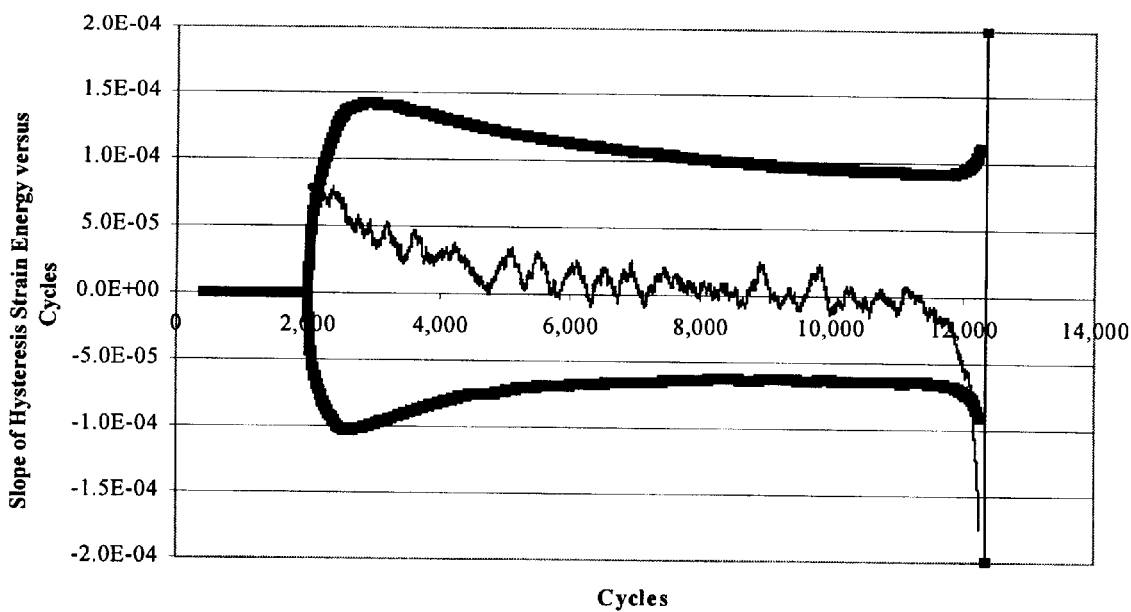
Figure 42:
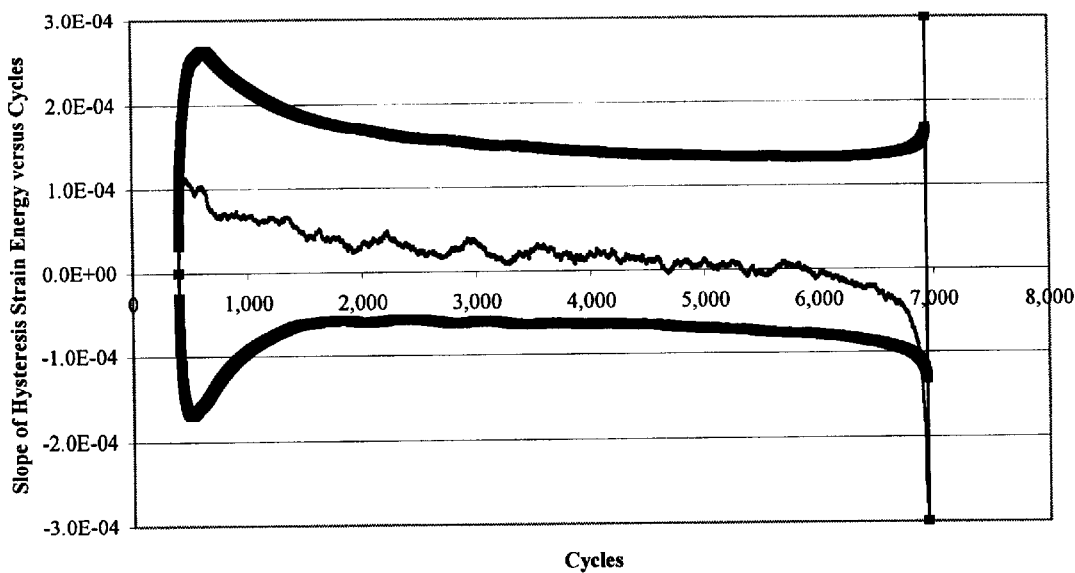
Figure 43:
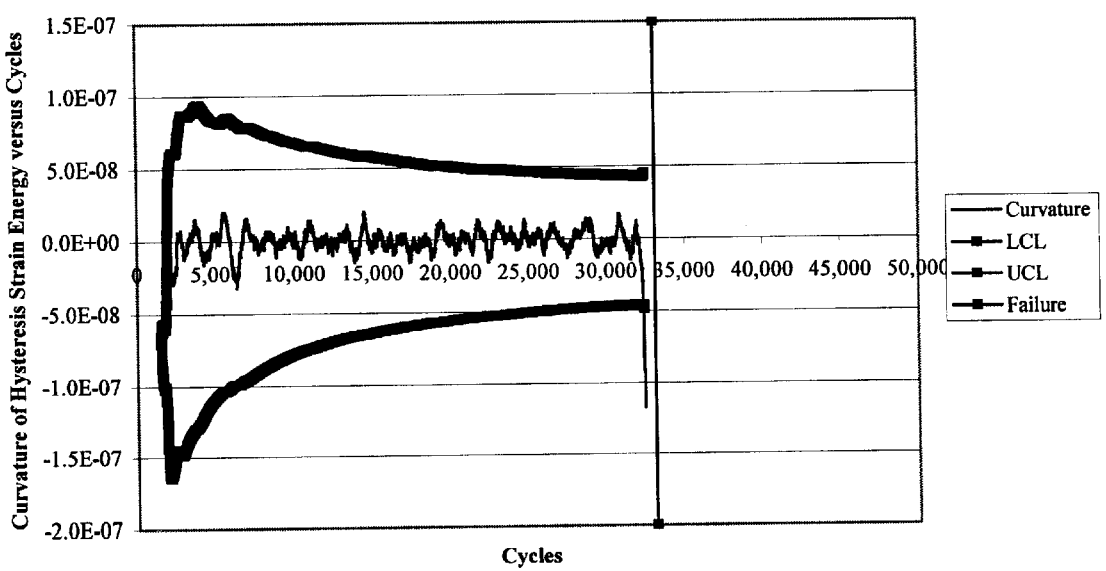
FIGS. 43–52 are graphs showing the curvatures of the HSE curves of FIGS. 23–32 with upper and lower control limit functions, as discussed in Example II, below.
Figure 44:
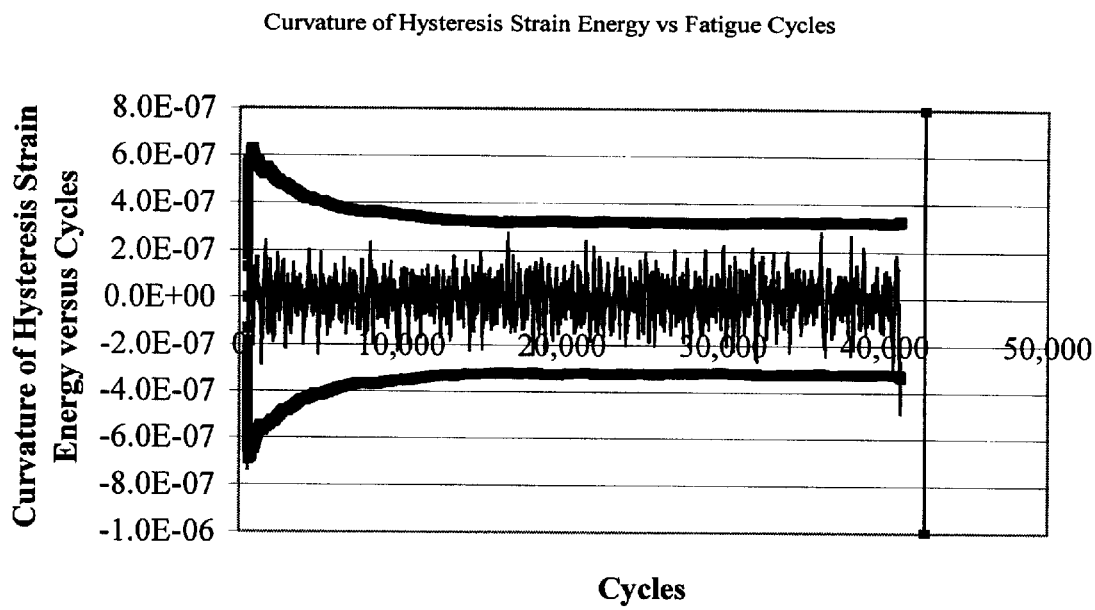
Figure 45:
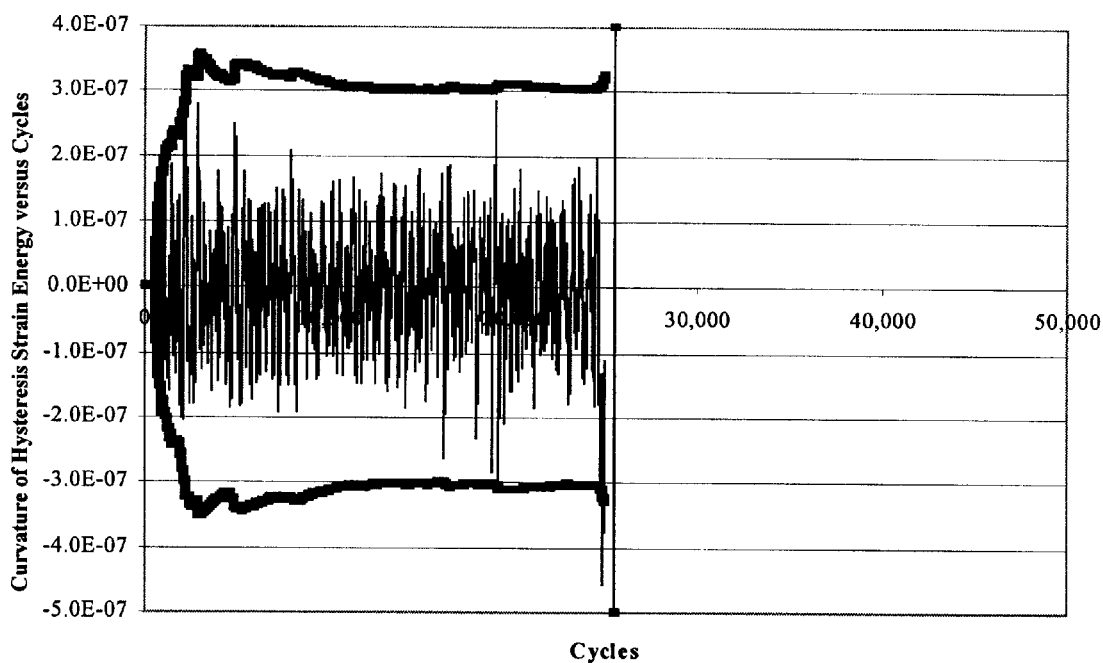
Figure 46:
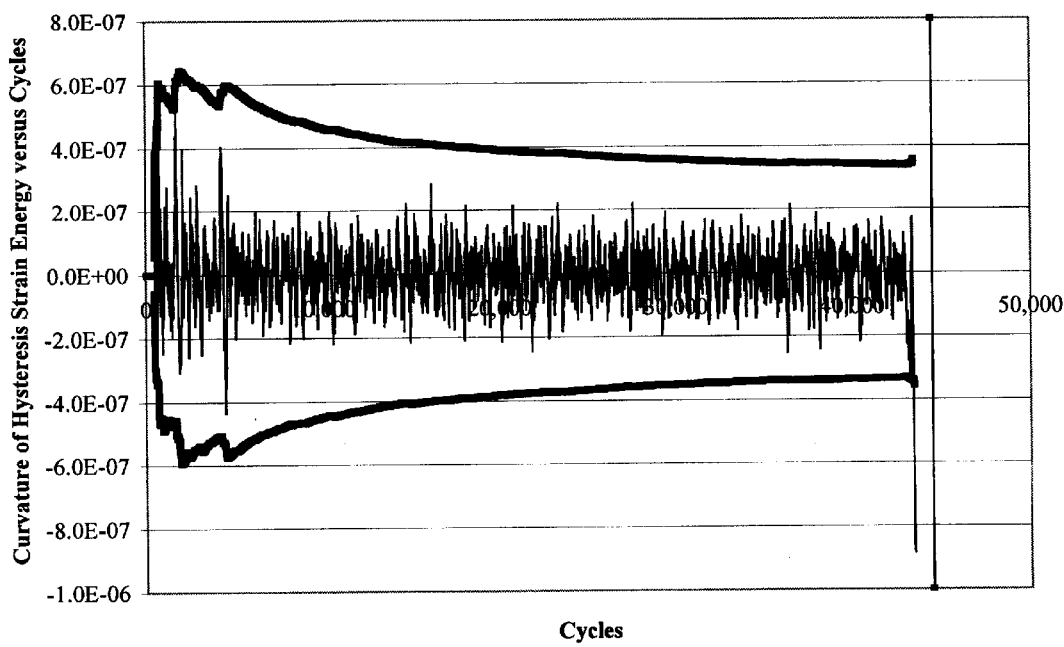
Figure 47:
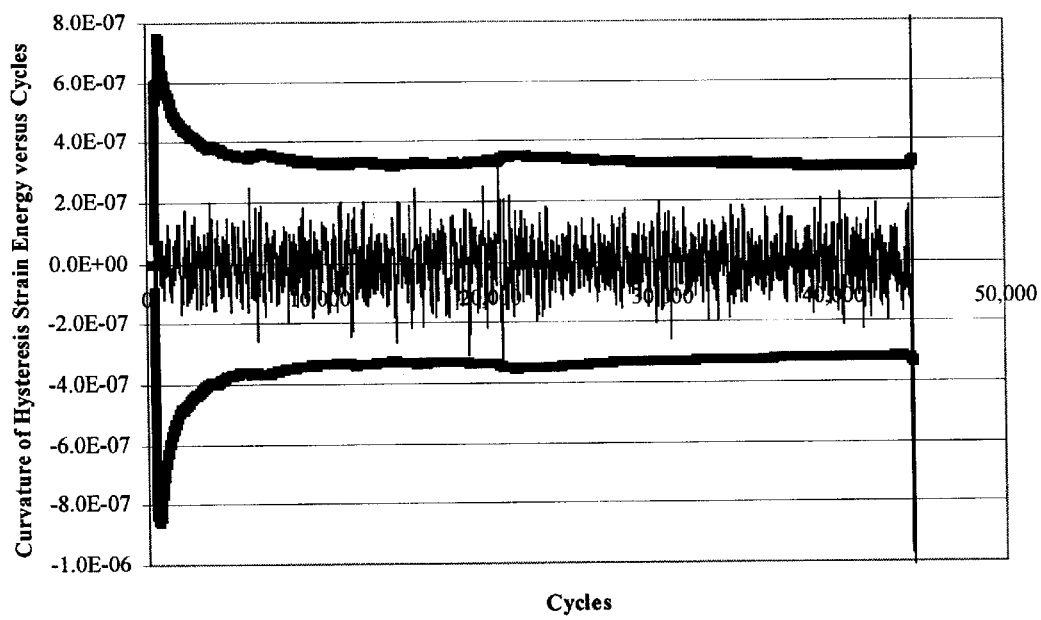
Figure 48:
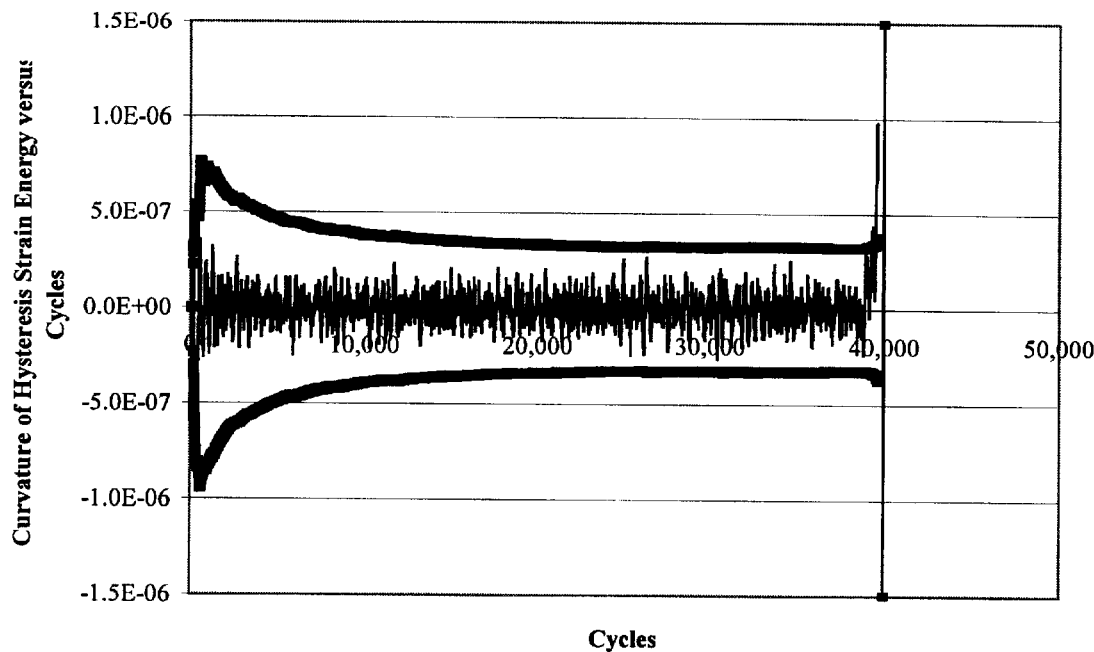
Figure 49:
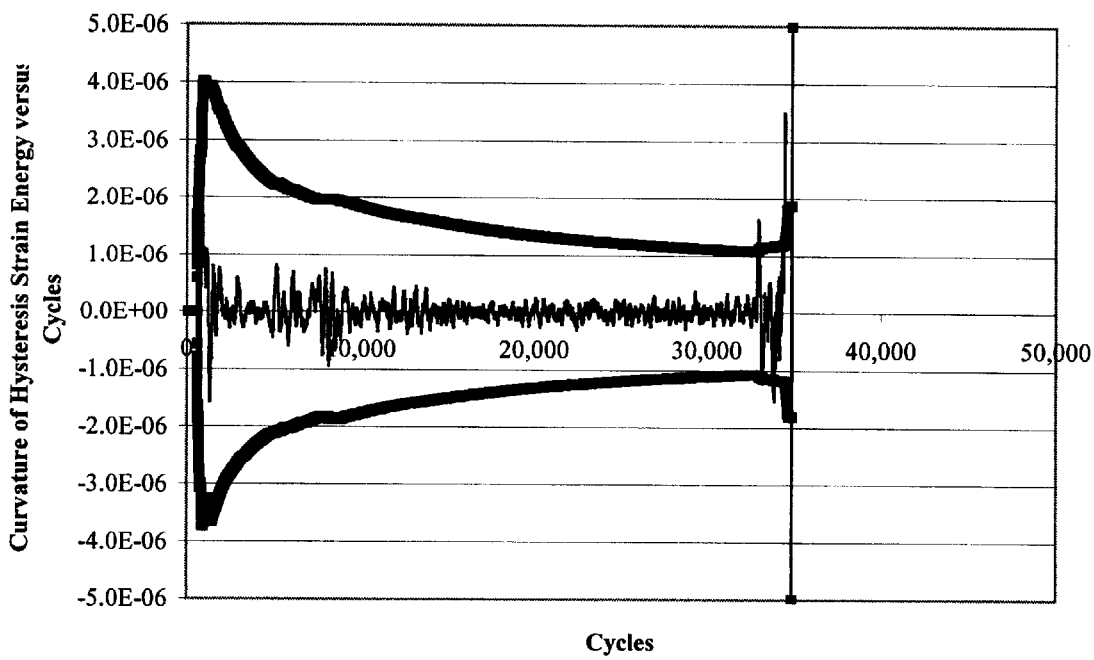
Figure 50:
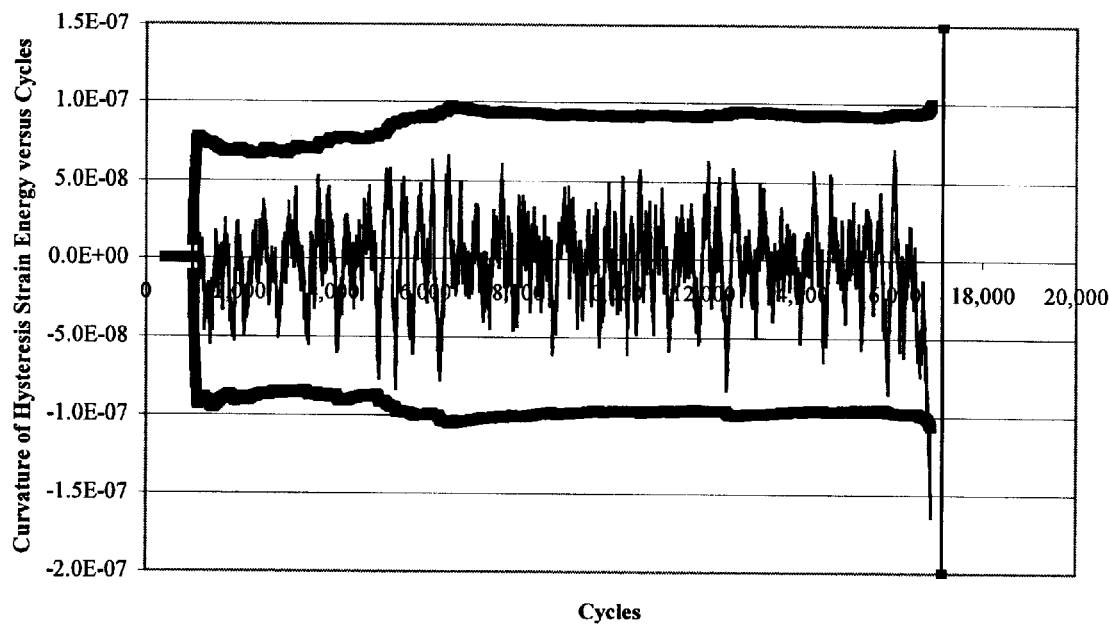
Figure 51:
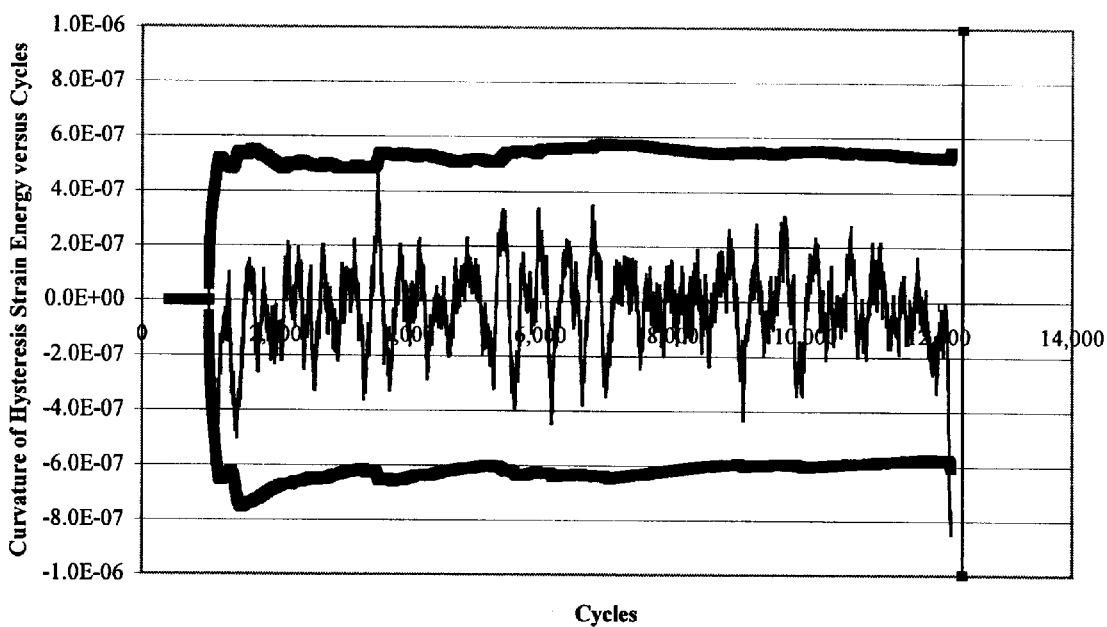
Figure 52:
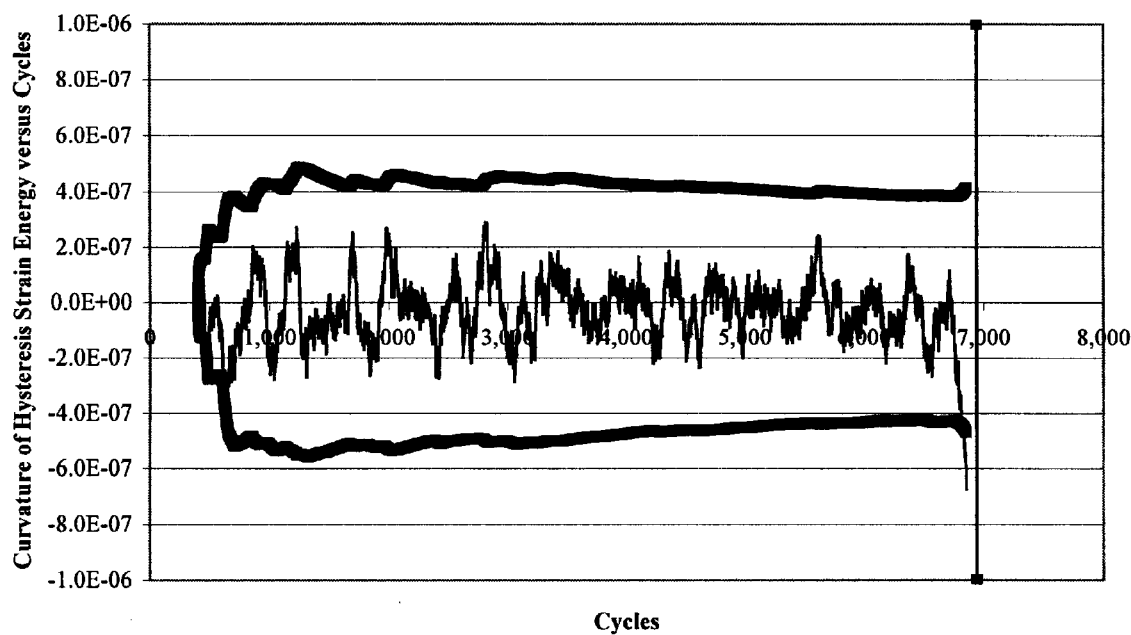

The various functions plotted from the data for the ten coupon samples are shown in FIGS. 14–52. FIGS. 14–22 show the plots for the input strain energy versus the number of cycles for samples TM-2 through TM-10 (this data was not plotted for TM-1). FIGS. 23–32 show the hysteresis strain energy plots for samples TM-1 through TM-10. FIGS. 33–42 and FIGS. 43 through 52 show, respectively, the slope functions with upper and lower control limit functions and the curvature functions with upper and lower limit functions for samples TM-1 through TM-10 respectively. As can be seen from these plots, the convergence of the slope or curvature function with a limit function serves as a reliable indicator of the imminent failure of the sample. FIG. 37, for example, shows the convergence of the slope function with the lower limit function prior to failure (the vertical line). FIG. 48 shows an example of the convergence of the curvature function with the plotted upper control limit function prior to the failure (shown as the vertical line).

Figure 54:
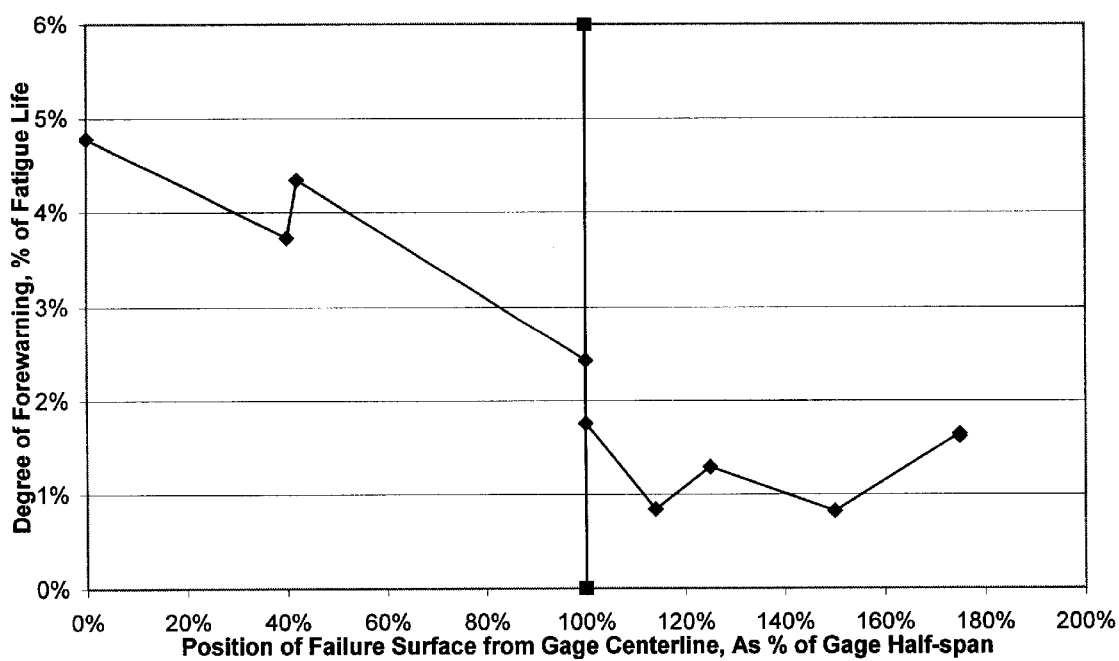
FIG. 54 is a plot of the relative degree of forewarning of failure relative to the position of the failure surface in aluminum test coupons discussed in Example II, below.

Table 4 in FIG. 53 is a numerical tabulation of the indicator function ("Indication based on:" line); the number of cycles at which either control limit function was crossed (the convergence); the number of cycles to convergence; the cycles to failure; and the numerical number of cycles between the indication and the failure. Fatigue life remaining after indication is provided in percent of total fatigue life, the percentage varying from less than about 5.0% to under 1.0%. FIG. 54 is a plot of these percentages as a function of the location of the failure surface relative to the gage midspan.

EXAMPLE III

This series of tests were designed to record tensile load and tensile strain on three classes of specimens: (1) tension-tension-loaded aluminum coupons designed to simulate multiple site damage (MSD) situations by containing a single drilled hole in the center of the gage section; (2) flexure-flexure-loaded I-beam samples in a four-point bend test; and (3) tensile-loaded single lap shear loaded coupons. The method of deriving HSE, slope, curvature, and control limit functions was as described above.

Figure 55:
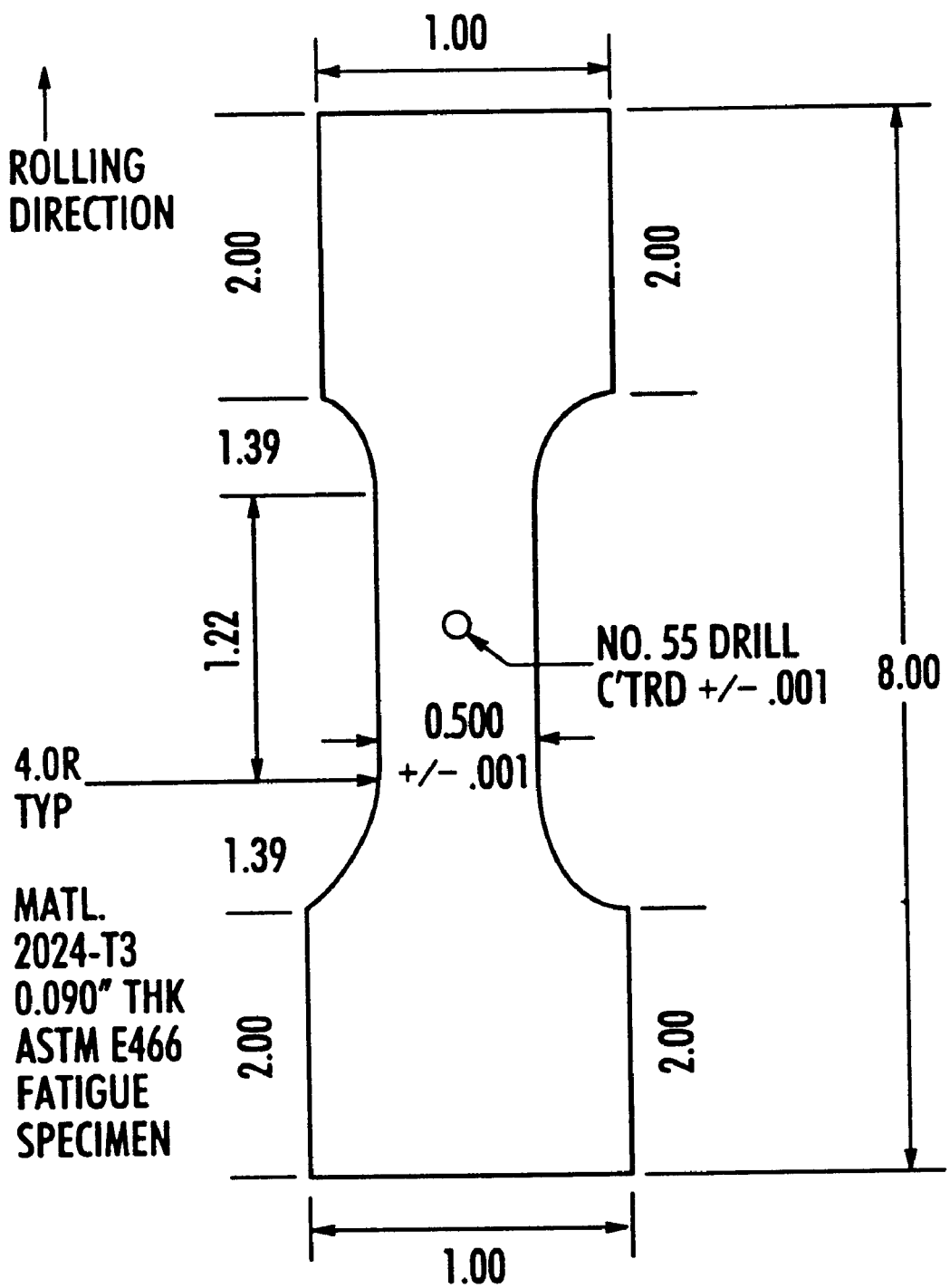
FIG. 55 is a sketch of the MSD simulation 2024-T3 coupon used in Example III, discussed below.
Figure 57:
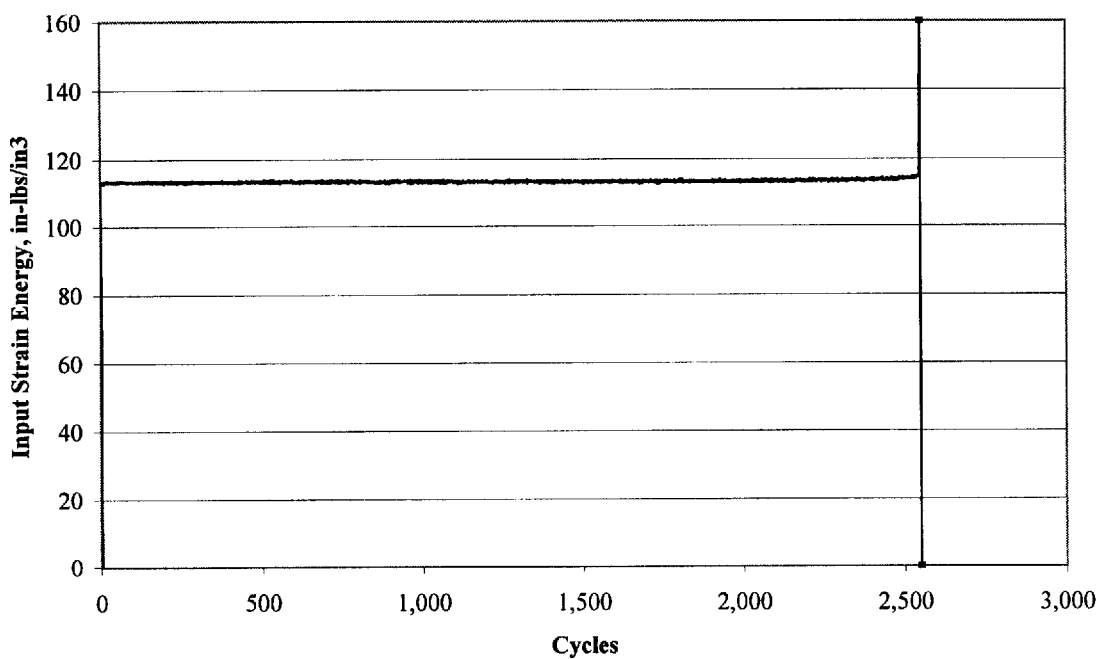
FIGS. 57–64 are plots of the input strain energy versus number of cycles for samples TM2-MDS-1 through TM2-MDS-8, as discussed in Example III, below.
Figure 58:
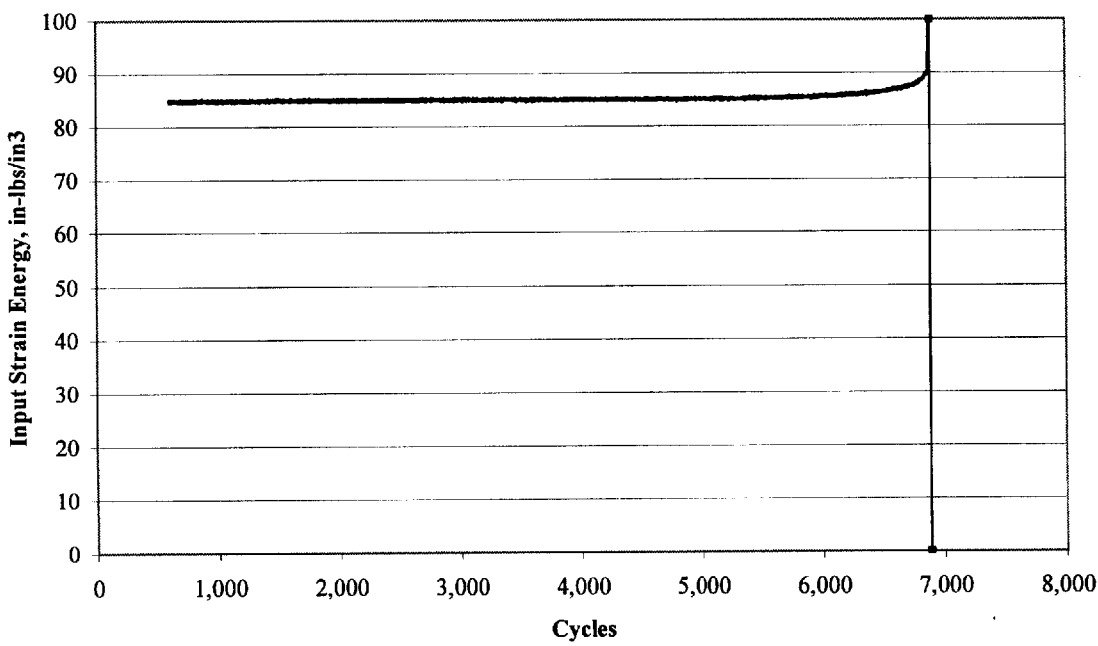
Figure 59:
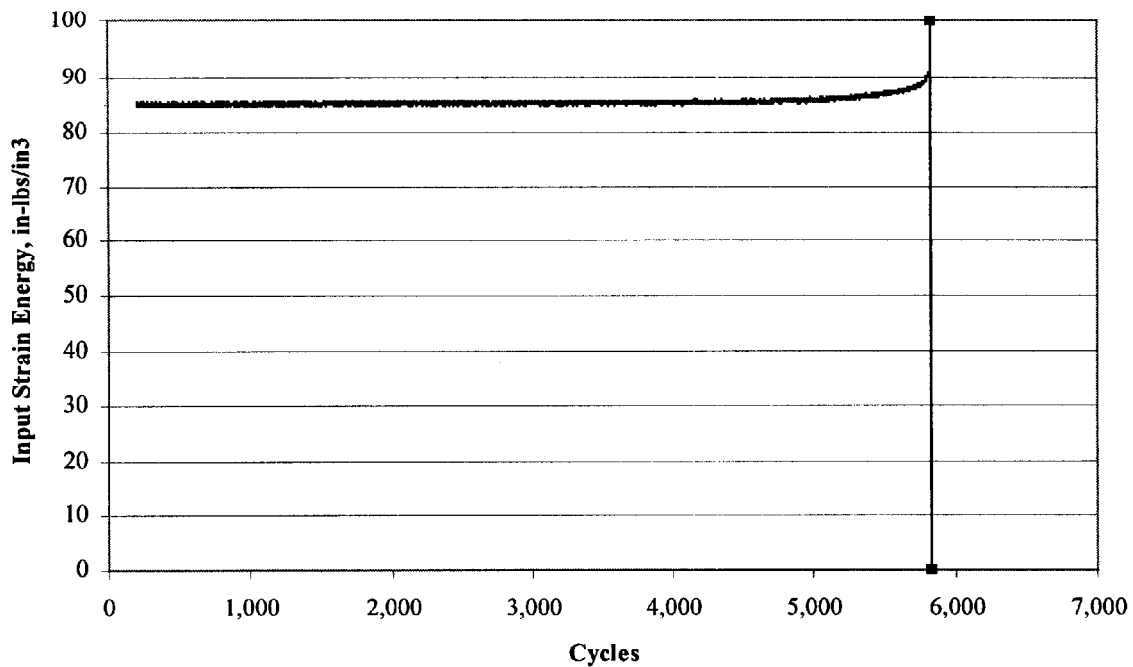
Figure 60:
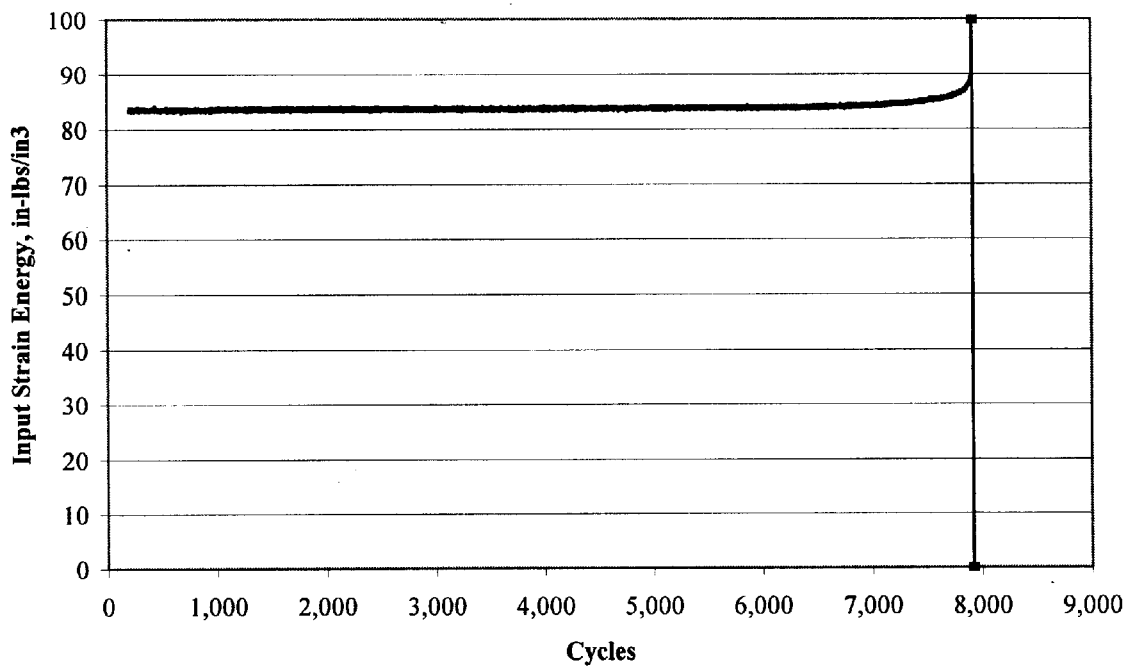
Figure 61:
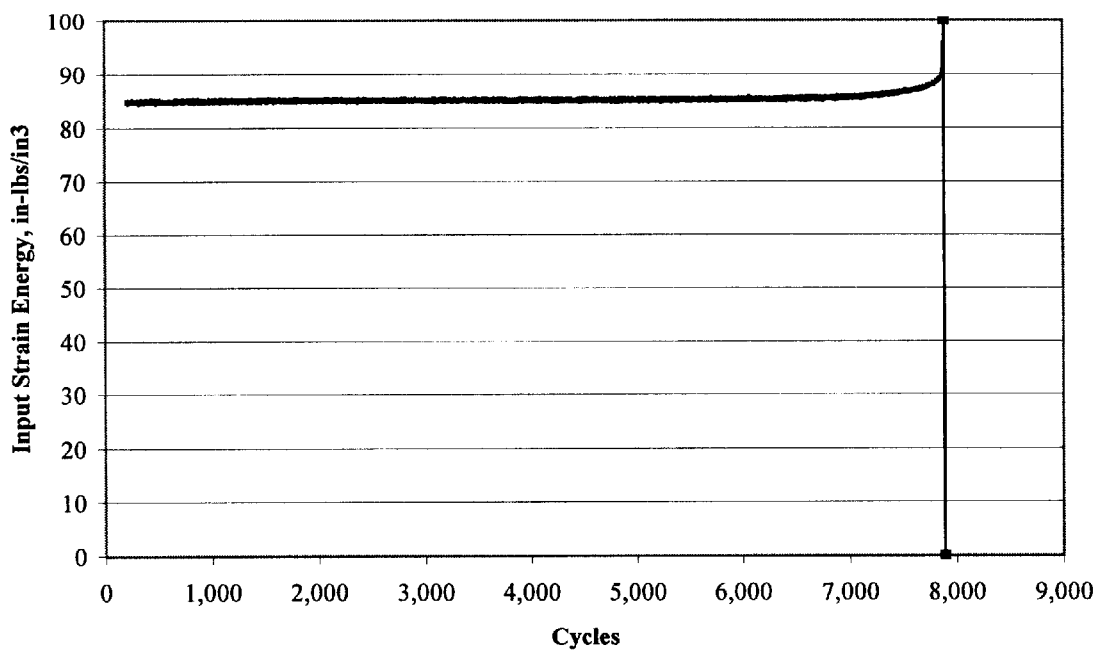
Figure 62:
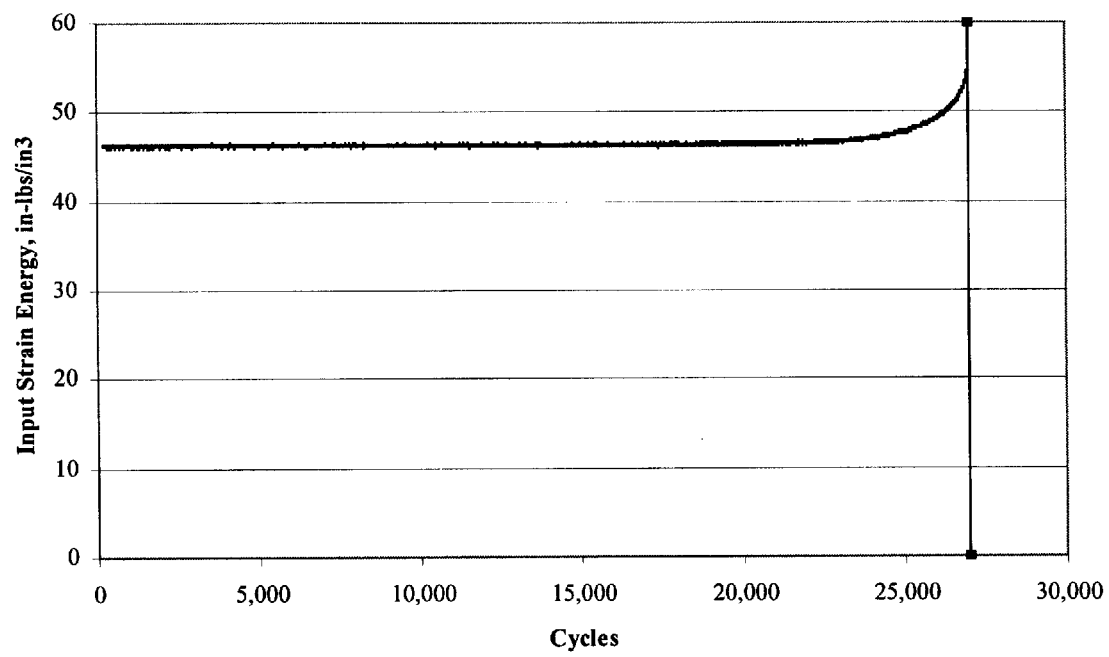
Figure 63:
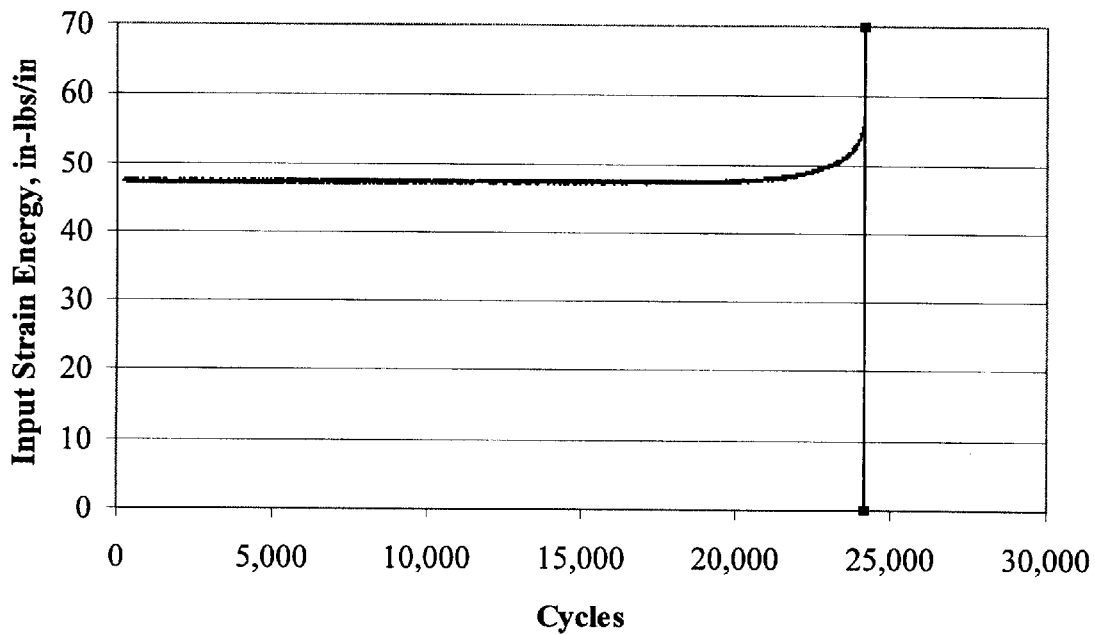
Figure 64:
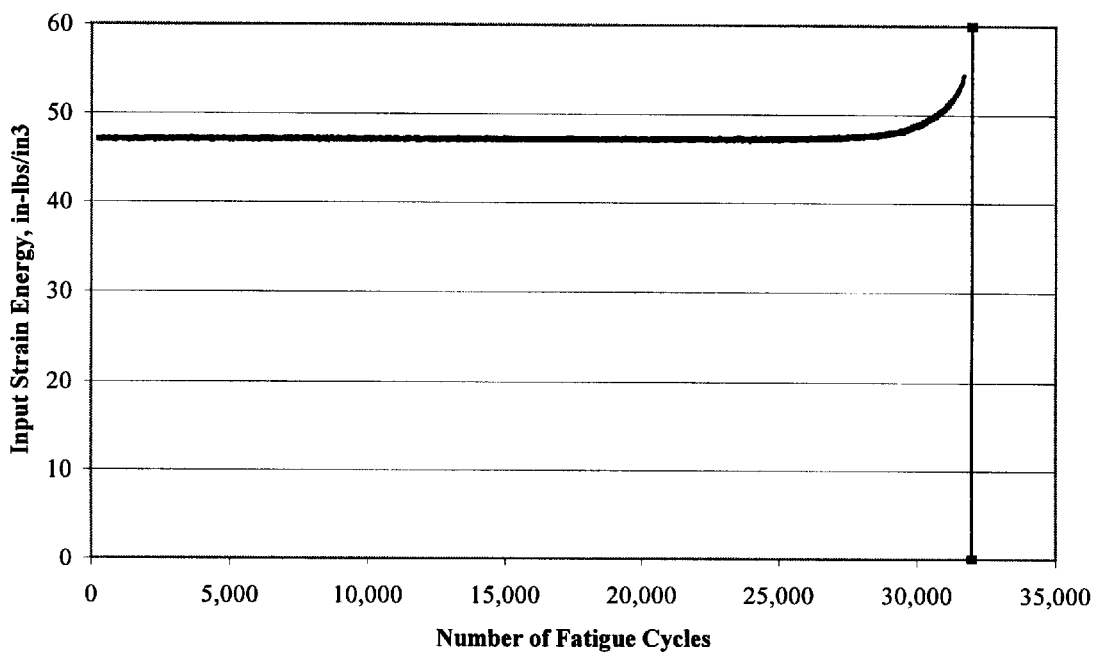
Figure 65:
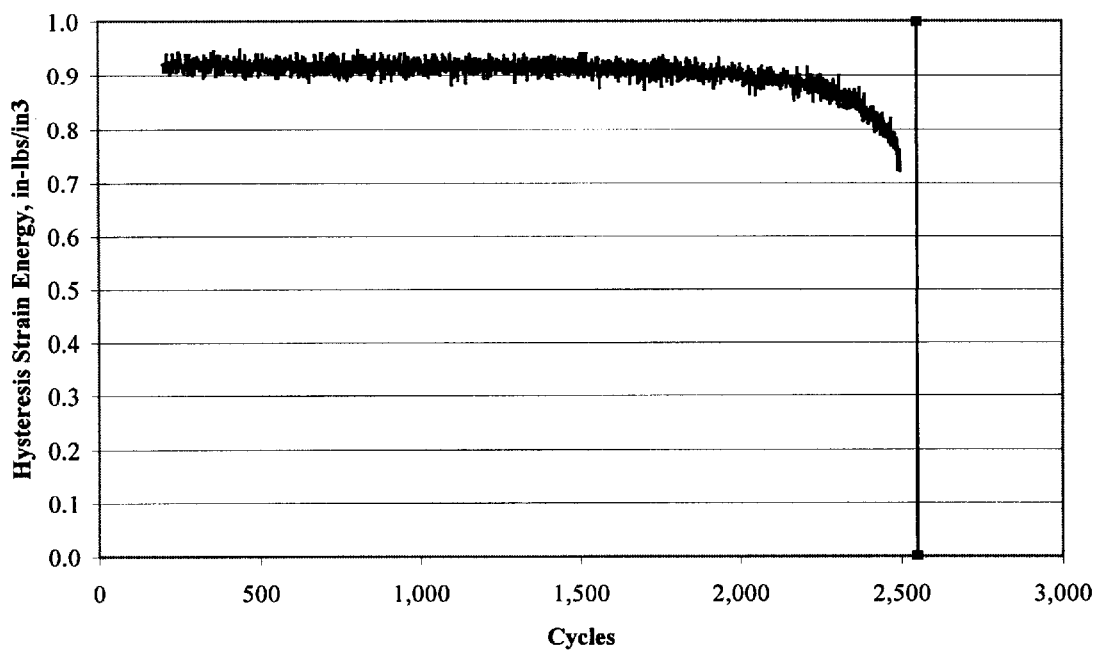
FIGS. 65–72 are plots of the hysteresis strain energy versus number of cycles for samples TM2-MDS-1 through TM2-MDS-8, as discussed in Example III, below.
Figure 66:
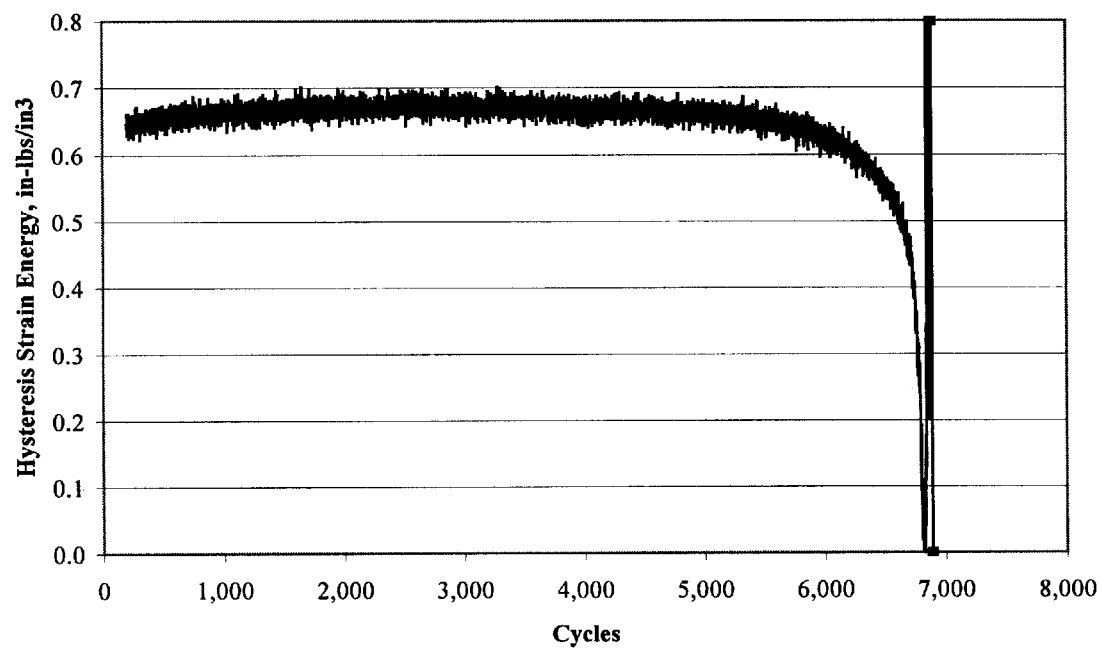
Figure 67:
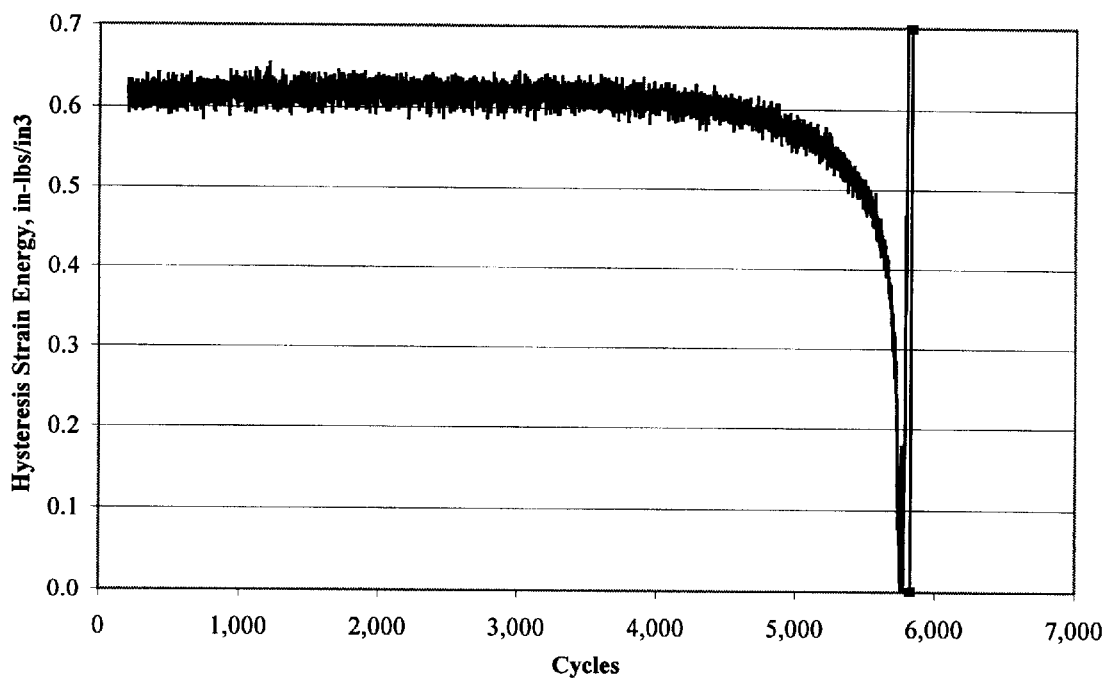
Figure 68:
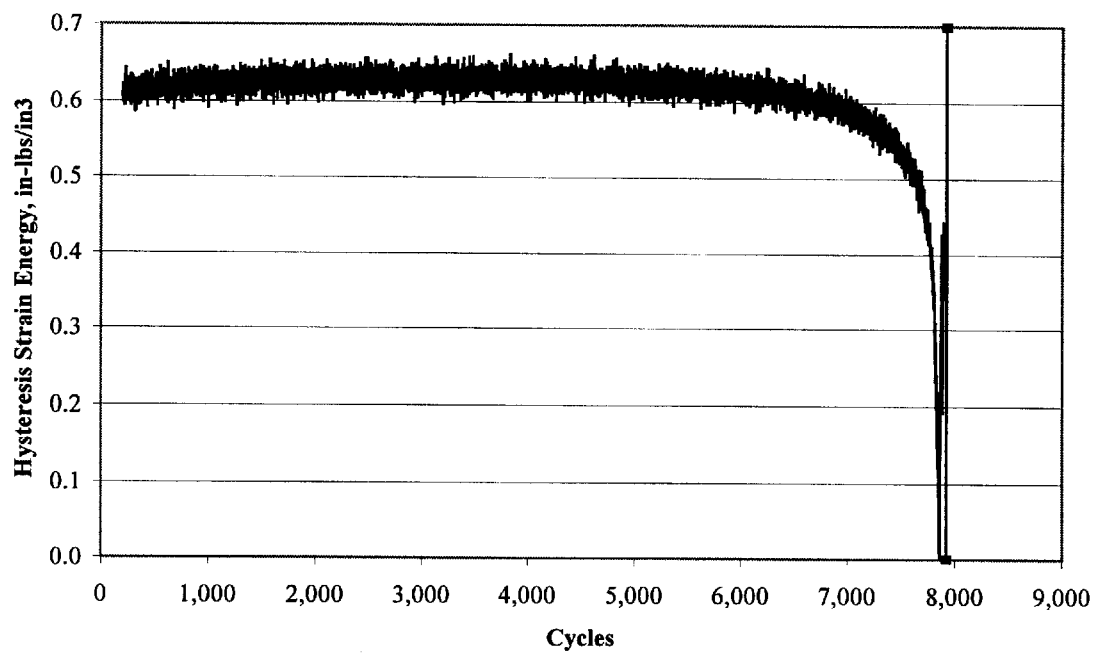
Figure 69:
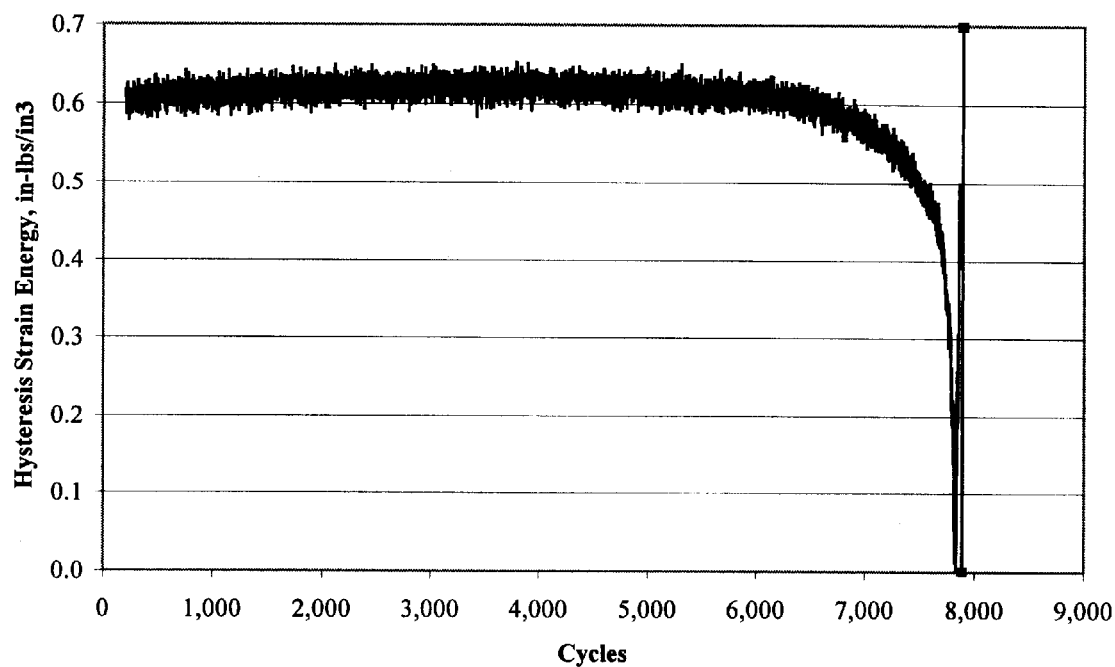
Figure 70:
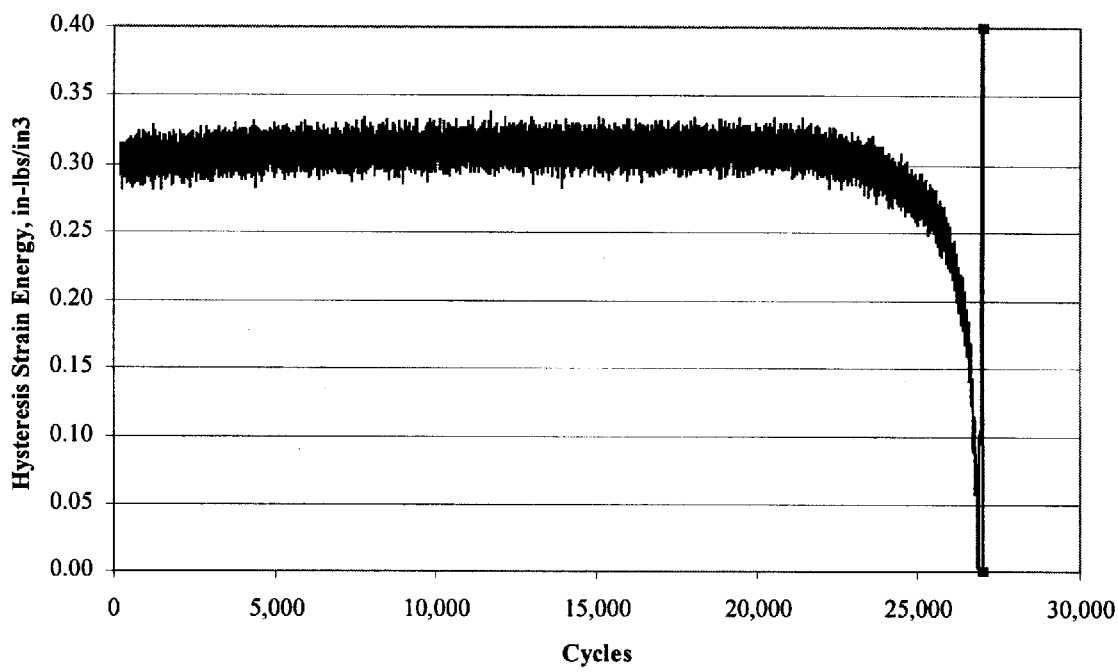
Figure 71:
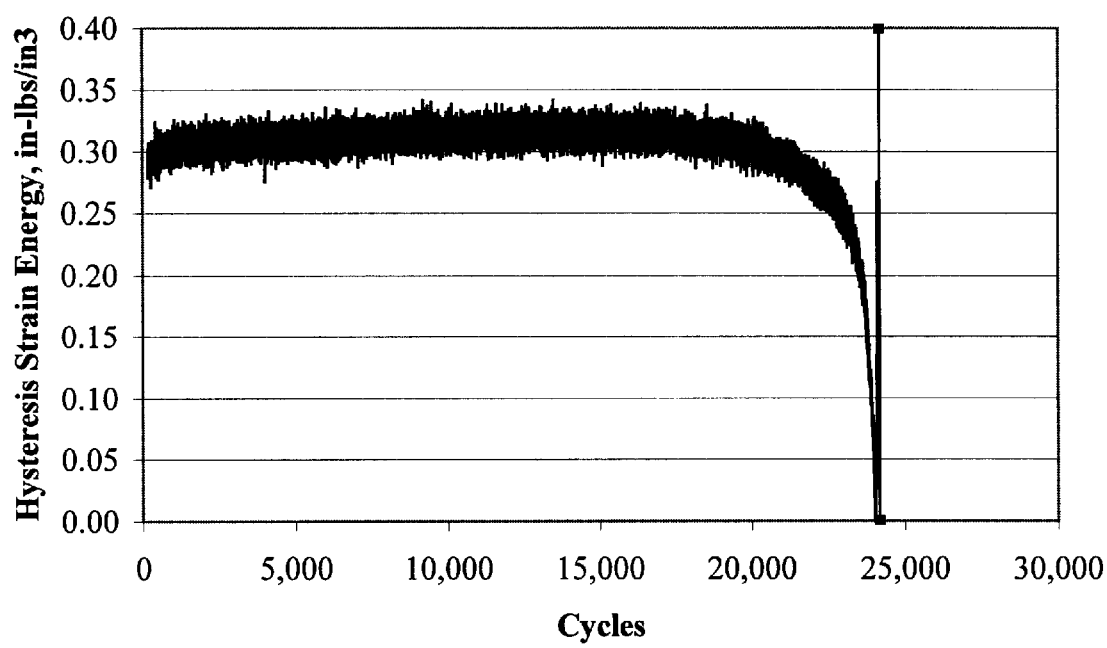
Figure 72:
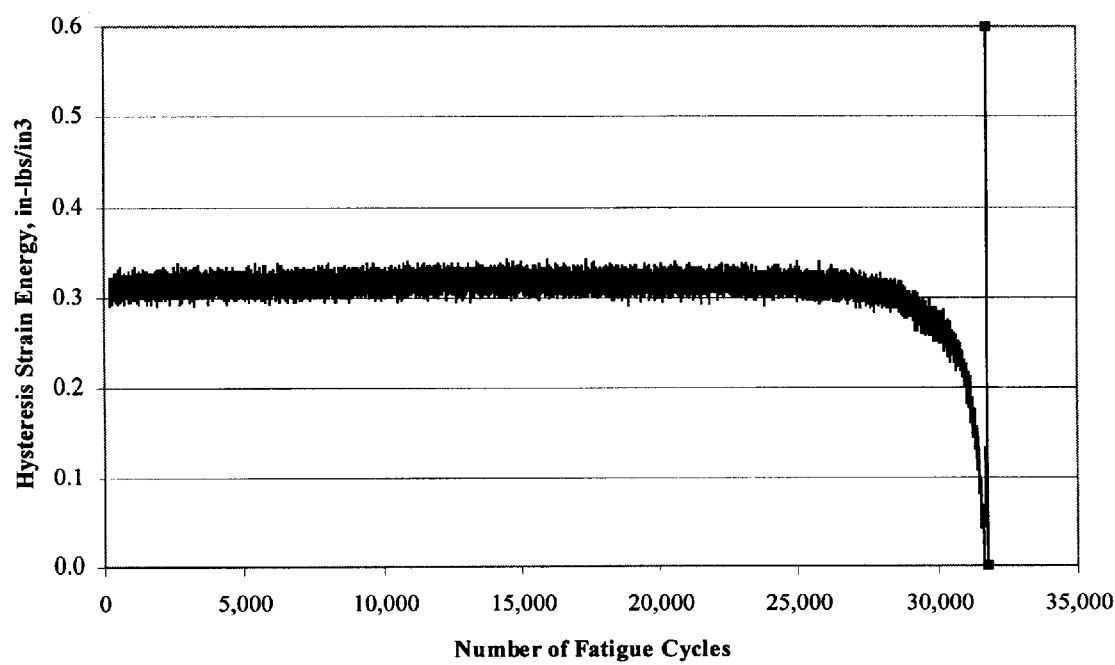
Figure 73:
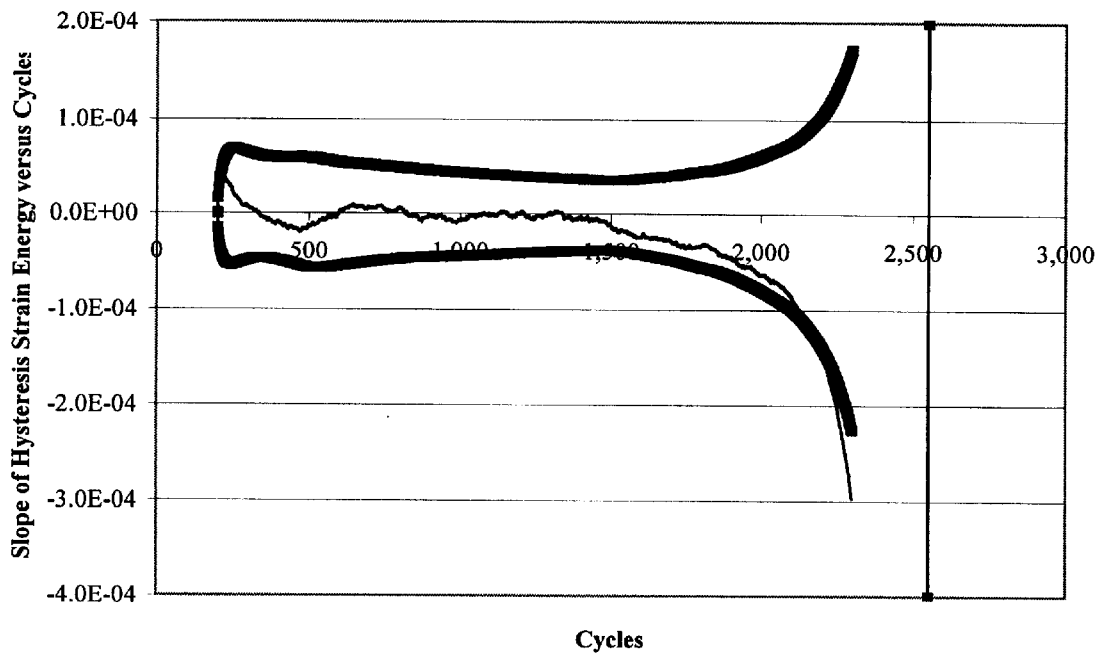
FIGS. 73–80 show the slope functions of the HSE functions in FIGS. 65–72 with upper and lower control limit functions, as discussed in Example III below.
Figure 74:
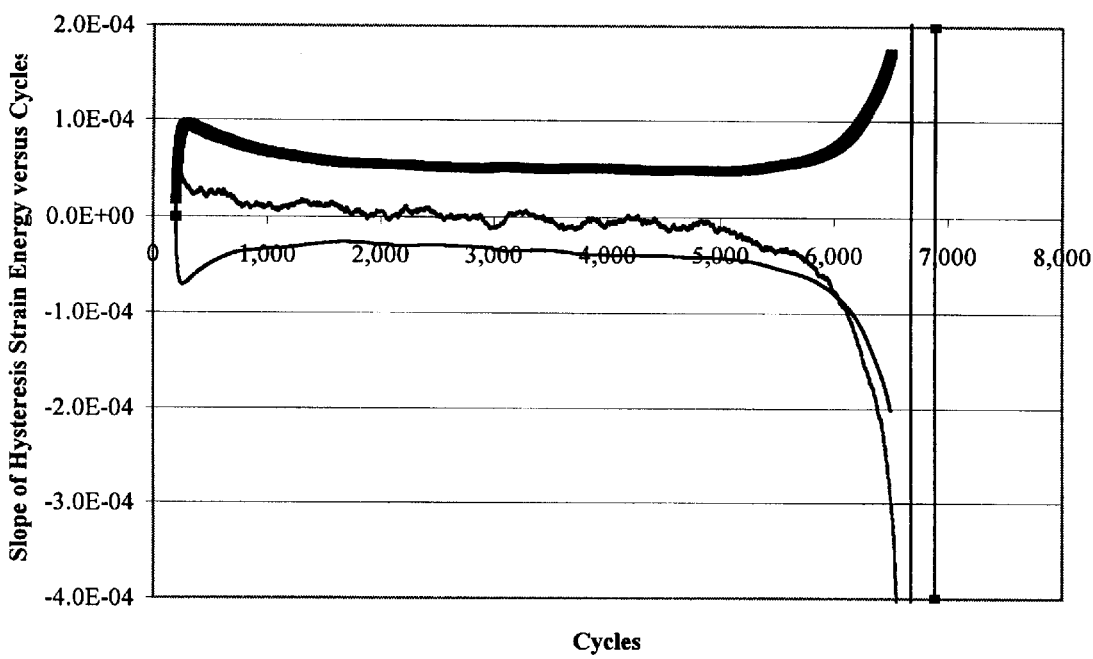
Figure 75:
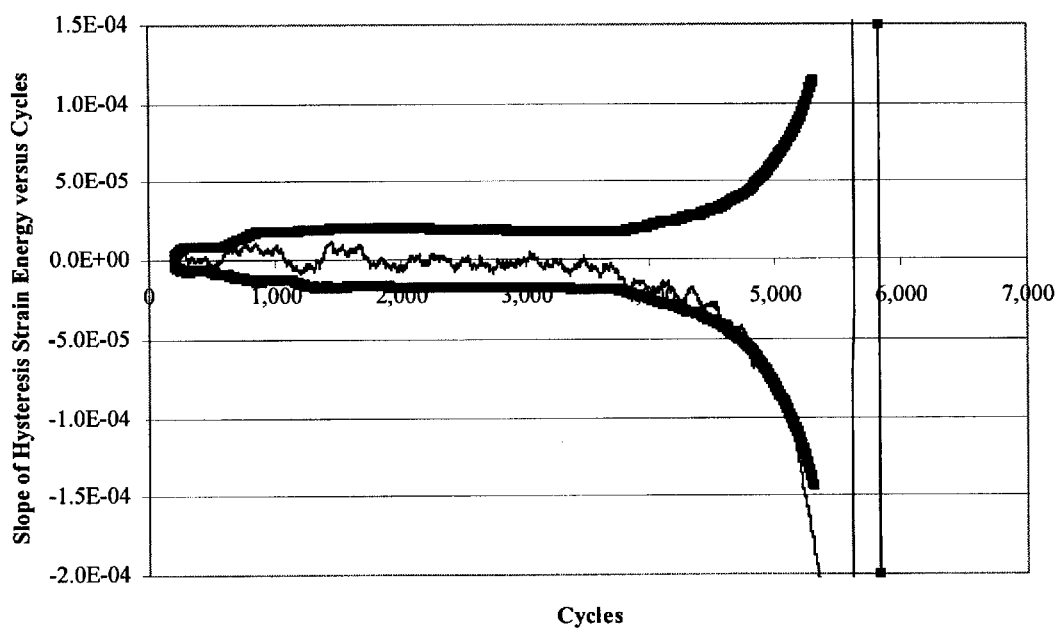
Figure 76:
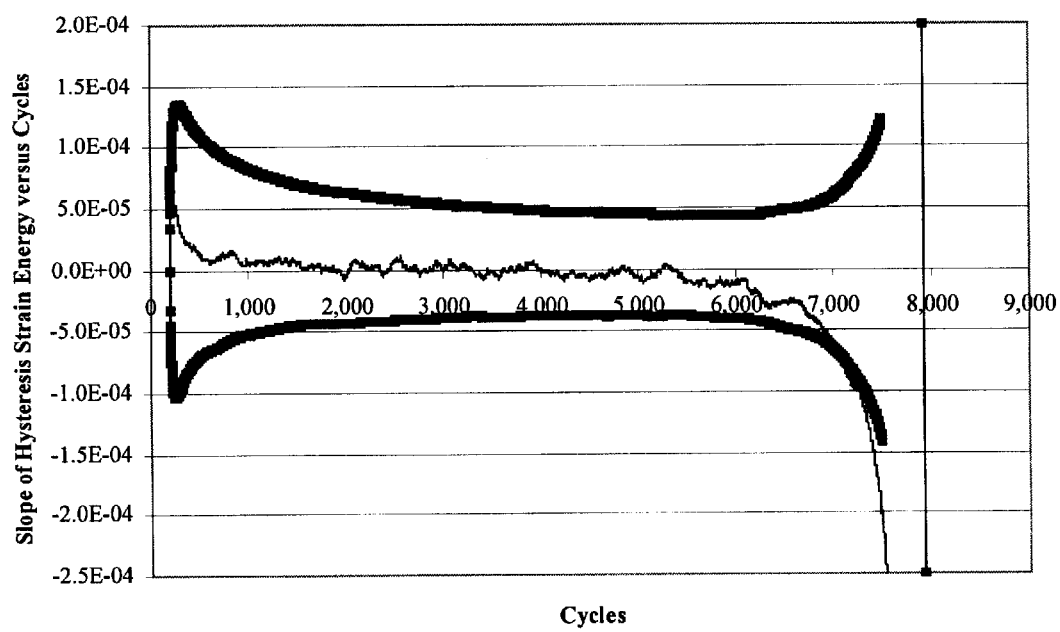
Figure 77:
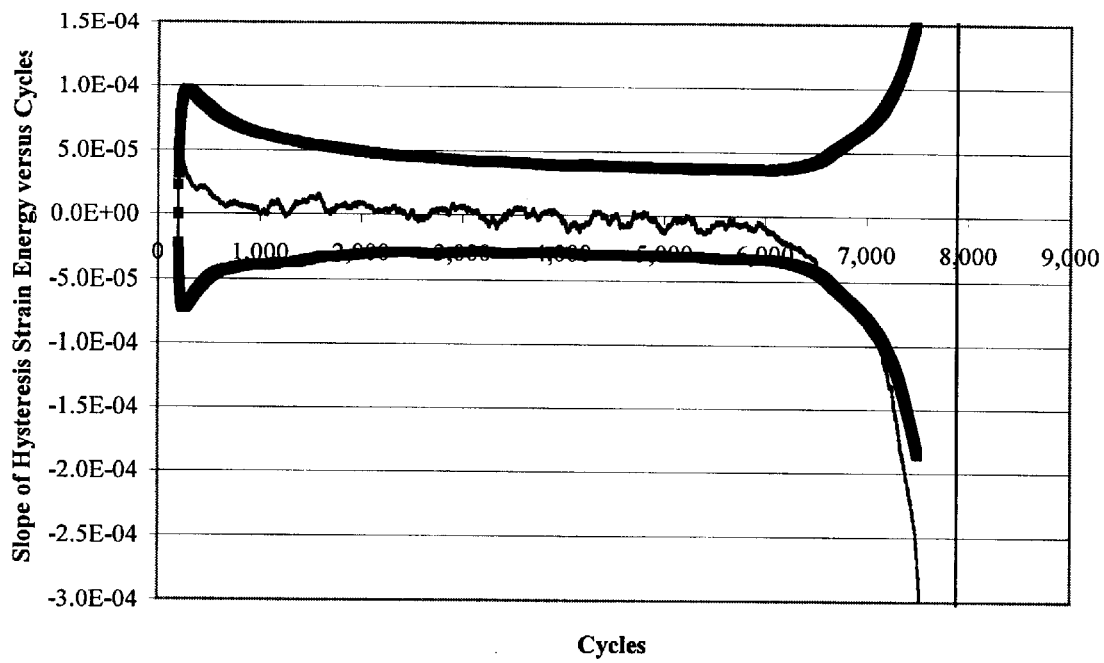
Figure 78:
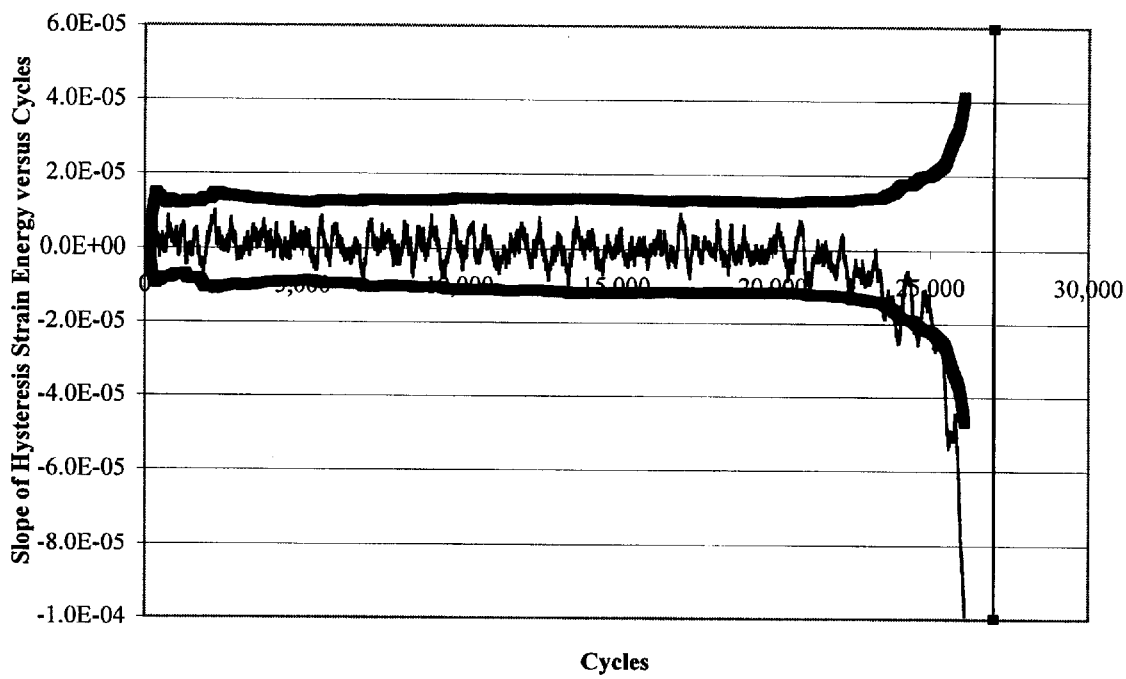
Figure 79:
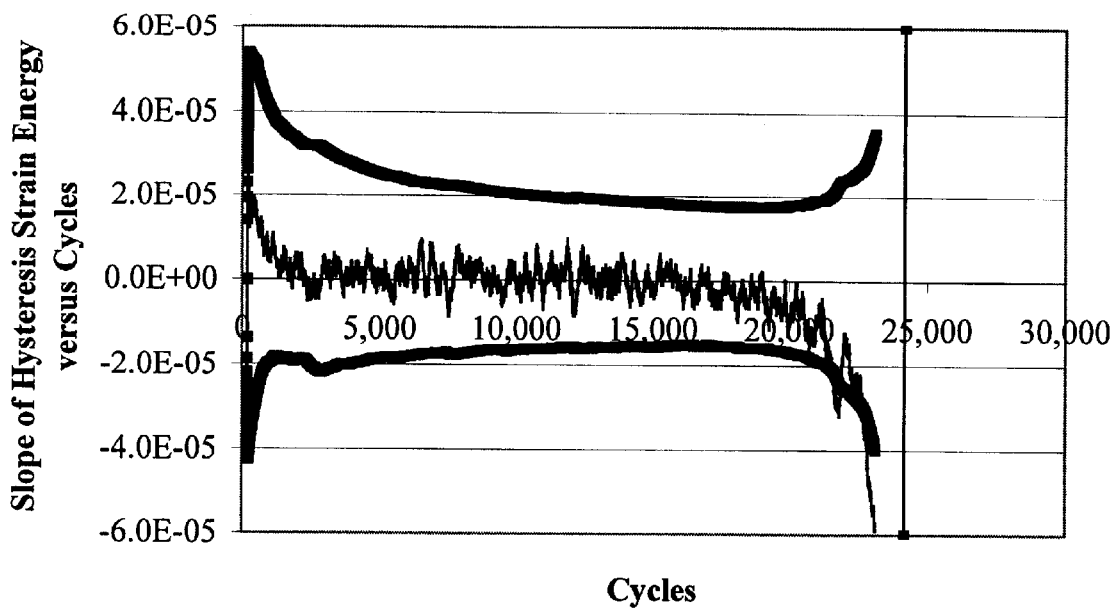
Figure 80:
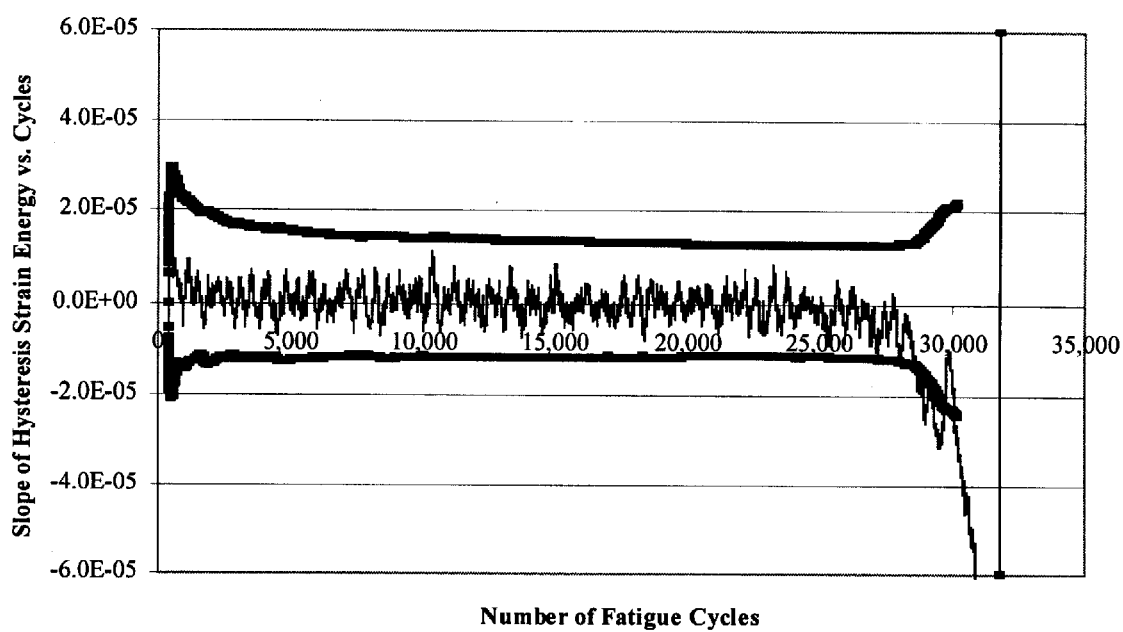
Figure 81:
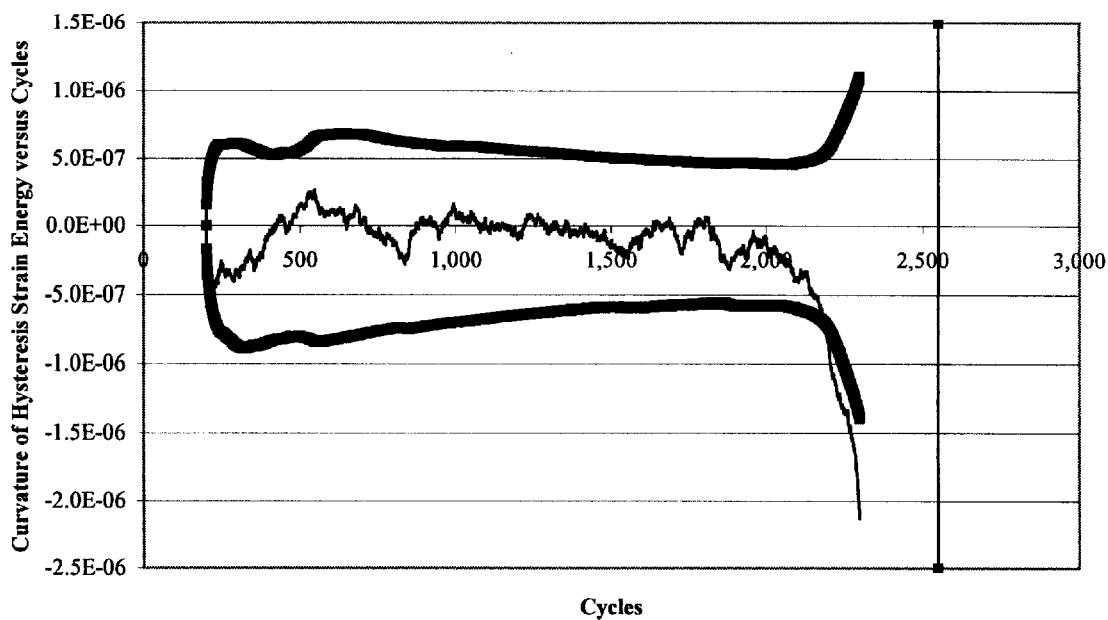
FIGS. 81–88 show the curvature functions of the HSE functions in FIGS. 65–72 with upper and lower control limit functions, as discussed in Example III below.
Figure 82:
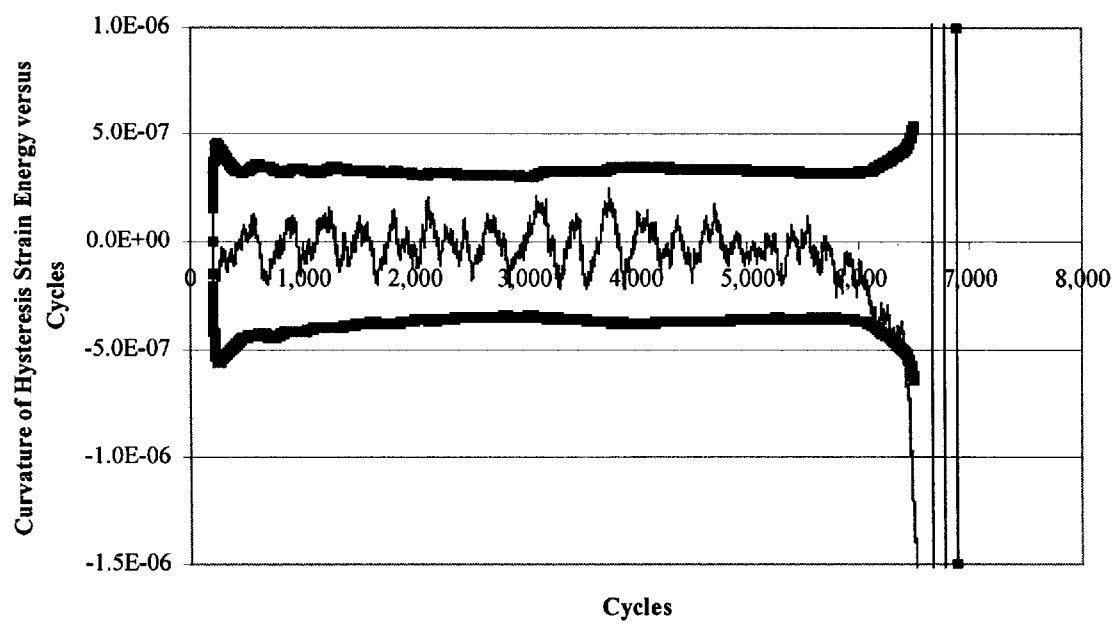
Figure 83:
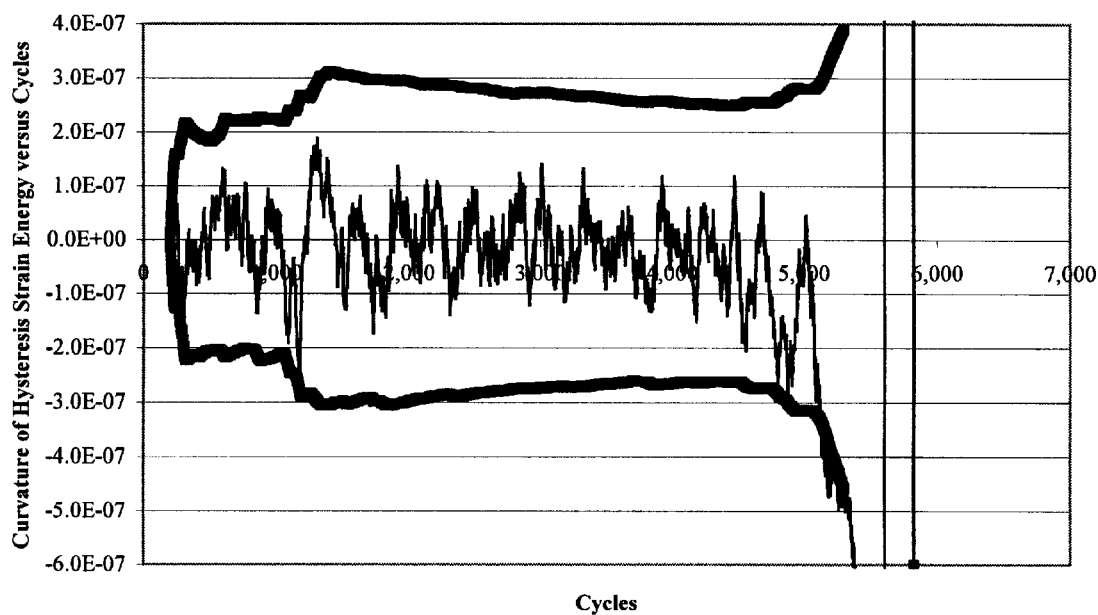
Figure 84:
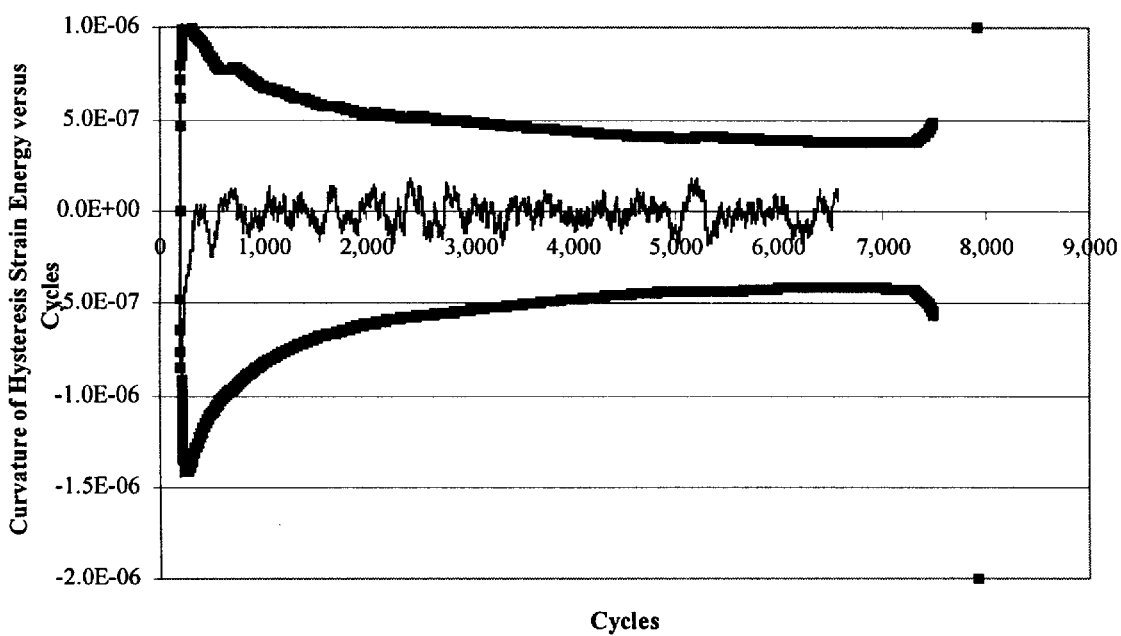
Figure 85:
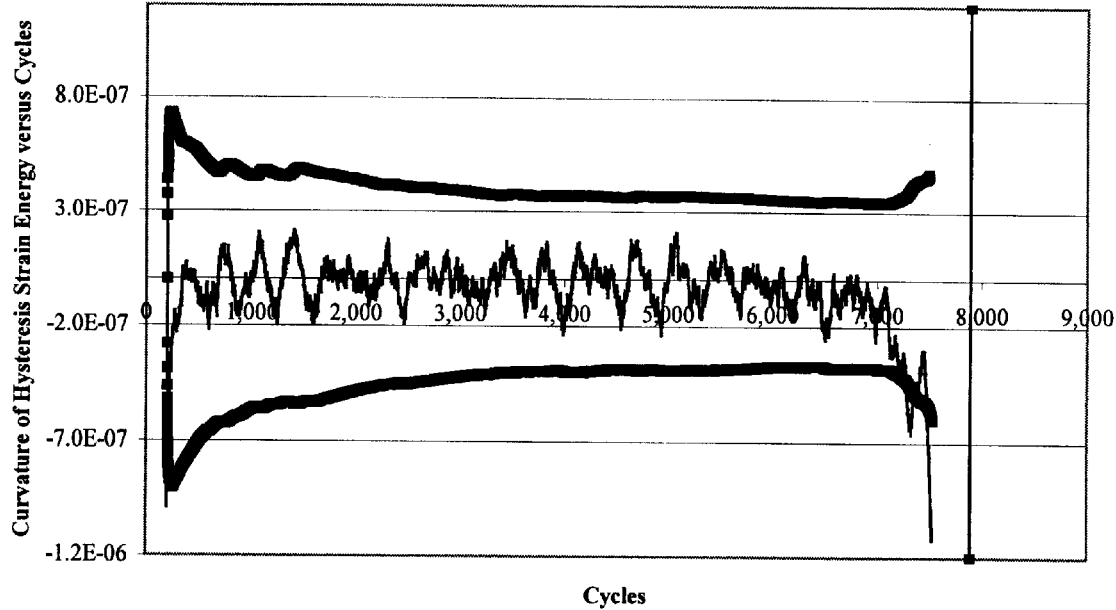
Figure 86:
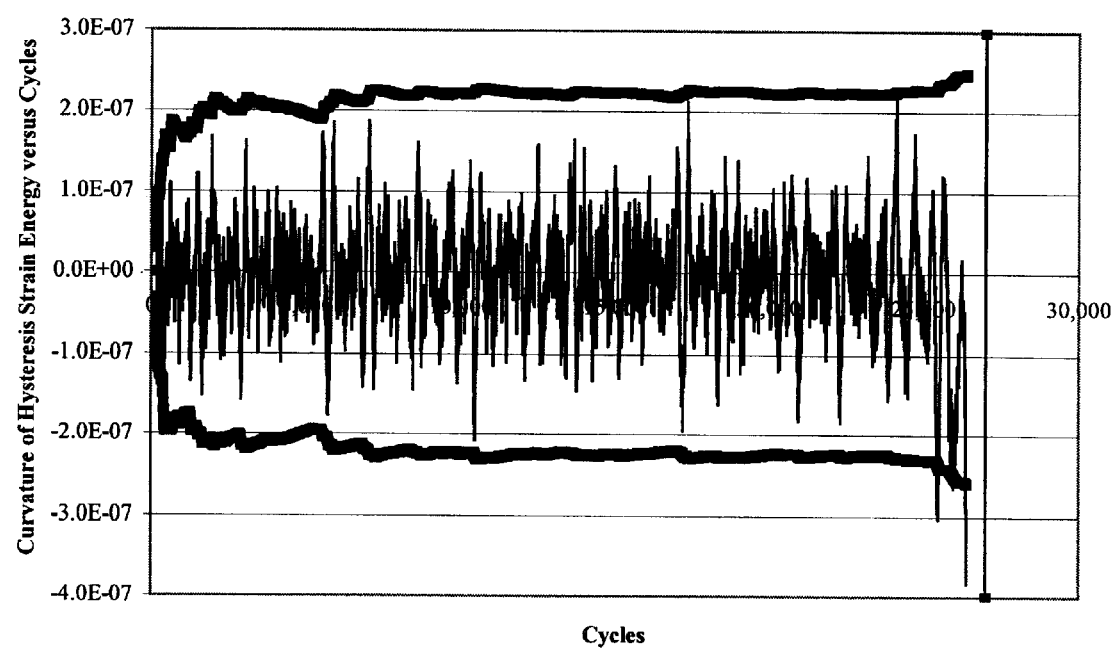
Figure 87:
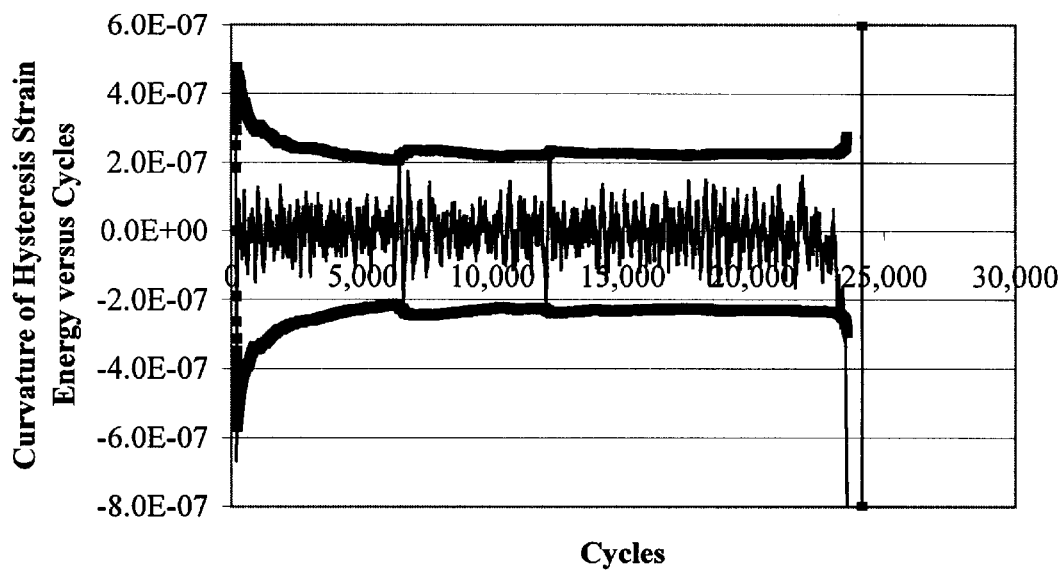
Figure 88:
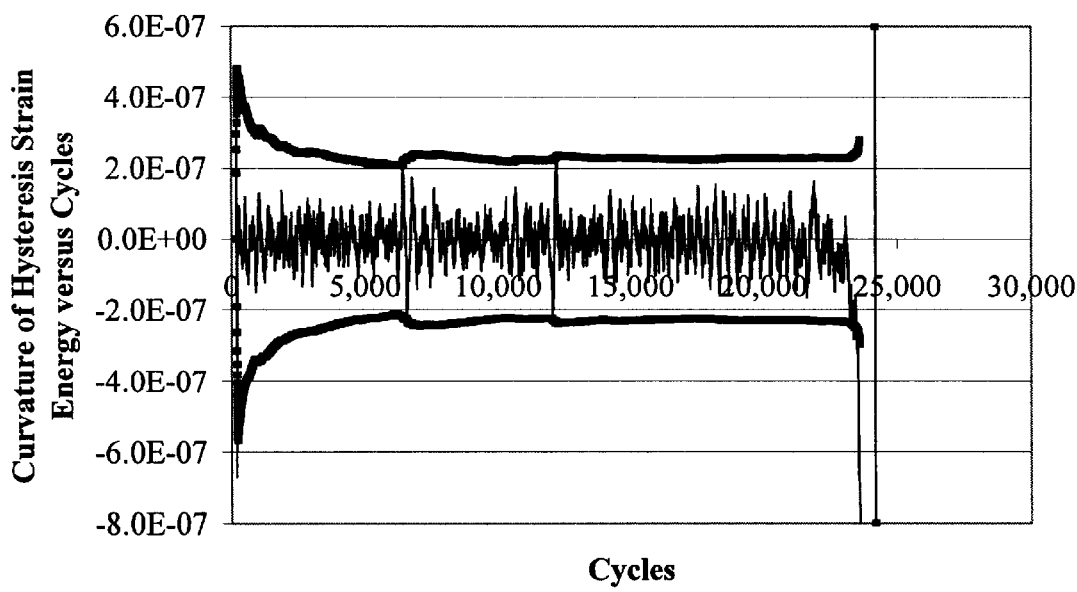

The sample material used for the tension-tension test was unclad 2024-T3 aluminum alloy with a thickness of 0.090 inches. The coupons were machined to an ASTM E466 standard fatigue specimen with cross-sectional dimensions of 1.22 inches long by 0.5 inches wide at the gage section. To simulate MSD situations, a single No. 55 hole (0.052 inches) was drilled in the center of each specimen's gage section. FIG. 55 is a sketch of a coupon specimen, showing placement of the drilled hole.

Apparatus and procedures were as described above for Examples I and II, with data collection rates of 2,000/ channel/second. Eight specimens designated TM2-MSD-1 through TM2-MSD-8 were fatigue tested in tension at R=0.1. Fatigue test results are shown in Table 5 in FIG. 56. FIGS. 57–64 are plots of the input strain energy versus number of cycles for samples TM2-MDS-1 through TM2-MDS-8. FIGS. 65–72 are plots of the hysteresis strain energy versus number of cycles for samples TM2-MDS-1 through TM2-MDS-8. FIGS. 73–80 -show the slope functions of the HSE functions in FIGS. 65–72 with upper and lower control limit functions. FIGS. 81–88 show the curvature functions of the HSE functions in FIGS. 65–72 with upper and lower control limit functions.

The table and the drawings show that the initial HSE consumption per fatigue cycle varies from approximately 0.07 in-lb for 17,333 psi to about 0.92 in-lb for 52,000 psi to 0.62 in-lb for 44,444 psi to about 0.3 in-lb for 33,333 psi. The HSE is relatively constant until it falls sharply at failure. The HSE curves were smoothed with the nonlinear, quadratic, zero-phase filter of the invention using a window of 200 cycles. Table 5 shows the predictive reliability of the intersection of the slope and/or curvature lines with the limit functions. Table 5 also shows the plateau value of the HSE, and illustrates the dependence of this value on the stress level.

EXAMPLE IV

A series of tests was performed on different specimens in corroded and uncorroded states, with some specimens artificially damaged to simulate MSD. For these tests, coupons of unclad 2024-T3 aluminum alloy, with a thickness of 0.090 inches, were used. The coupons were machined to an ASTM E466 standard fatigue specimen with cross-sectional dimensions of 1.22 inches long by 0.5 inches wide in the gage section for the 1-inch extensometer used. MSD was simulated by drilling a No. 15 hole (0.180 inches) in the center of the gage section.

For each experiment, the two data variables tensile load and tensile strain in the reduced section were recorded. Loading was performed on a servohydraulic test machine having a 25,000 lb. tensile capacity at room temperature. Fatigue loading frequency was 0.1 Hz. Data were recorded by a National Instruments PCI 16XE-50 General Purpose I/O System of 16-bit resolution. Data recording frequency was approximately 2,000/channel/second, producing about 200 measurements of each variable over each fatigue cycle. Load cell voltage variations were on the order of about 0.1% (10 mV) of full scale (10 V), or 10 lb. Measurement resolution was 1 lb in load measurement (about 10 psi) and 5 $\mu\epsilon$ in strain measurement.

Figure 89A:
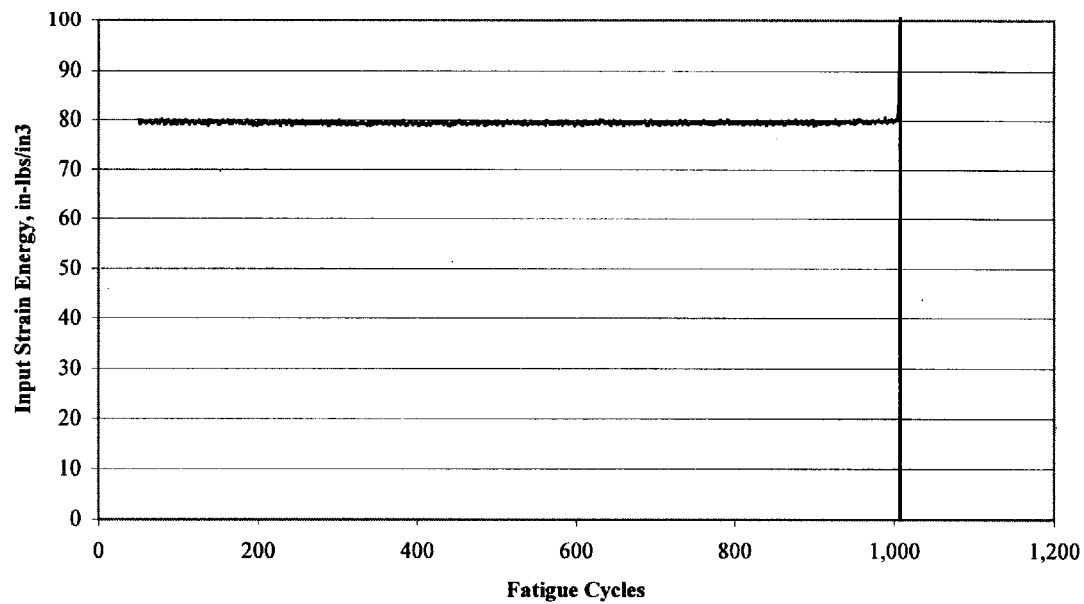
FIG. 89 shows the data curves for a tension-tension test of an aluminum coupon treated to simulate multiple site damage and corrosion, the curves showing: (a) the input strain energy; (b) the hysteresis strain energy (HSE); (c) the slope of the HSE curve, with upper and lower control limit functions, and (d) the curvature of the HSE curve, with upper and lower control limit functions.
Figure 89B:
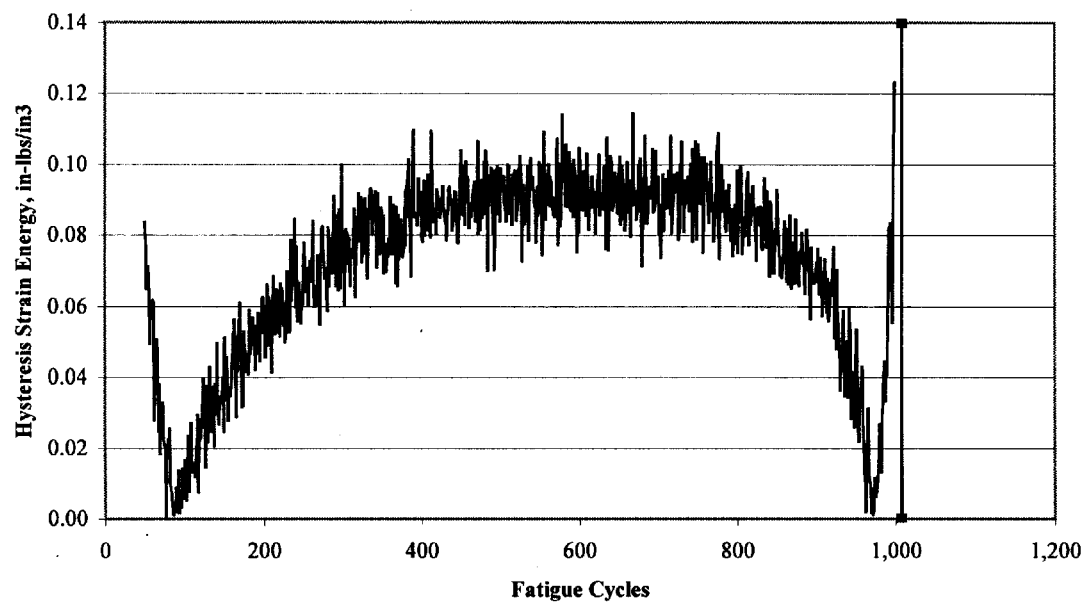
Figure 89:
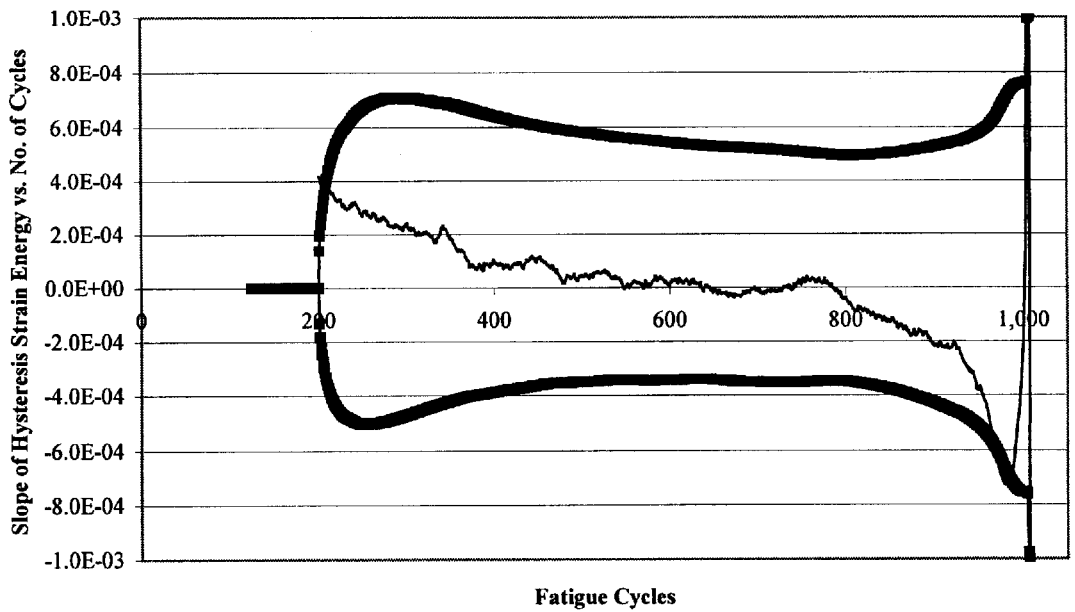
Figure 89:
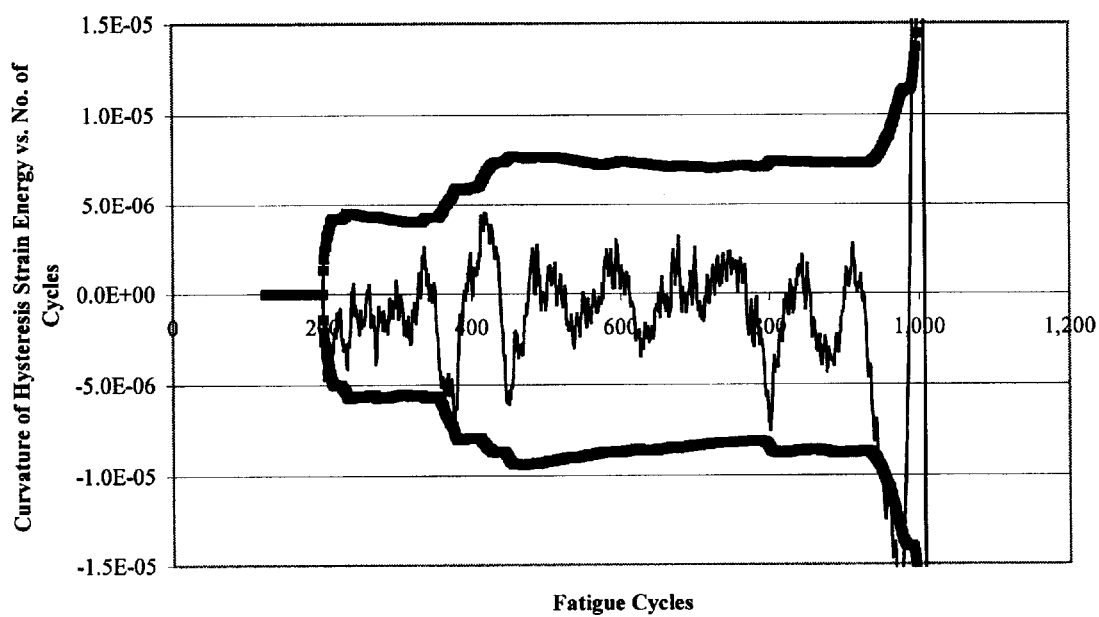
Figure 90A:
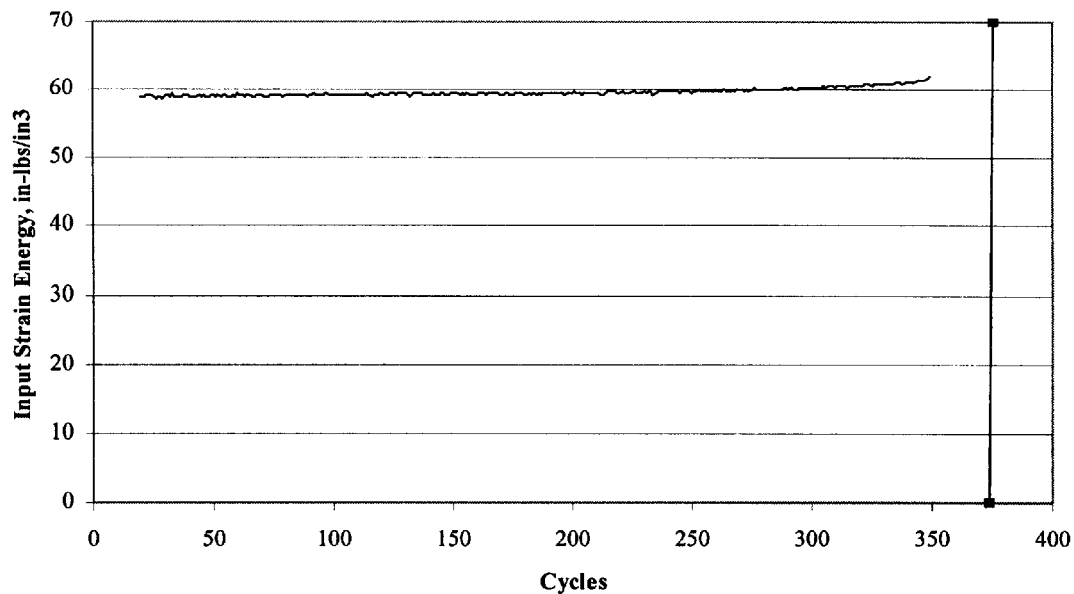
FIG. 90 shows the data curves for a tension-tension test of a notched aluminum coupon, the curves showing: (a) the input strain energy; (b) the hysteresis strain energy (HSE); (c) the slope of the HSE curve, with upper and lower control limit functions, and (d) the curvature of the HSE curve, with upper and lower control limit functions.
Figure 90B:
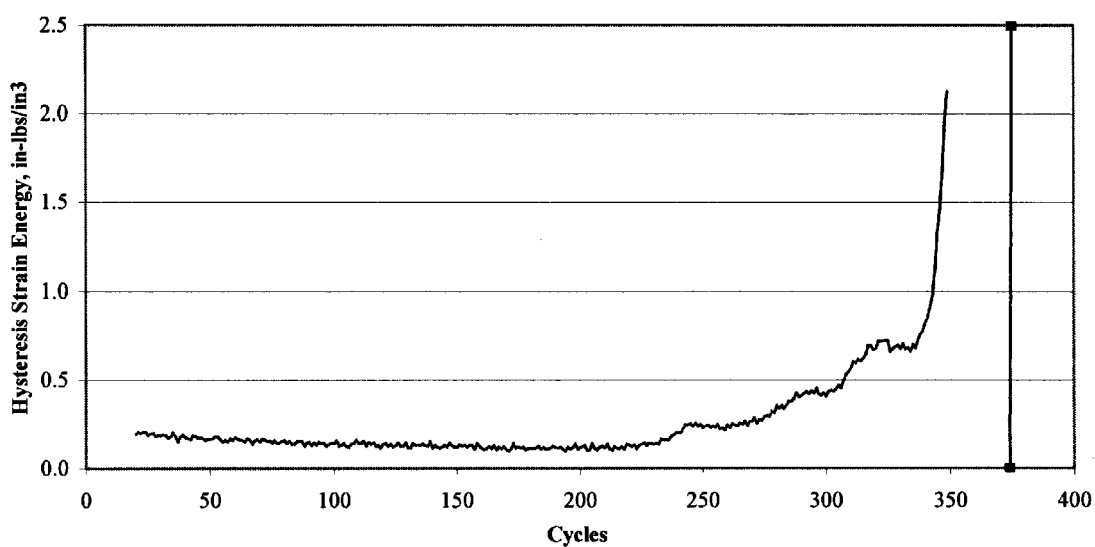
Figure 90C:
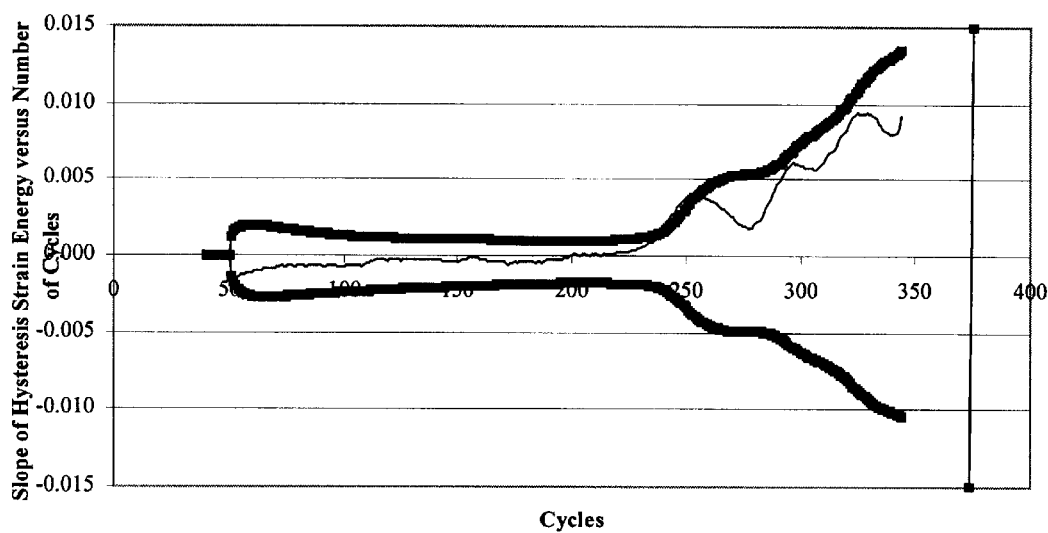
Figure 90D:
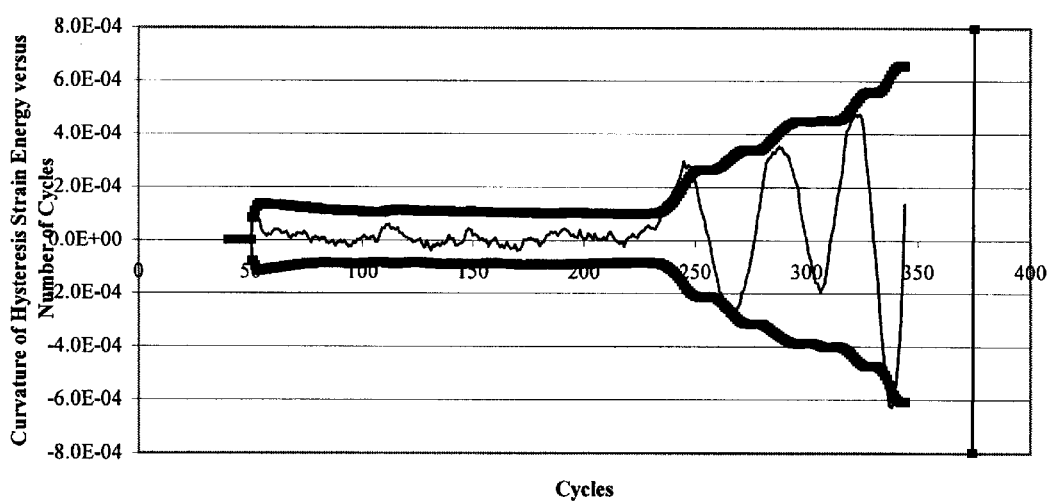
Figure 91A:
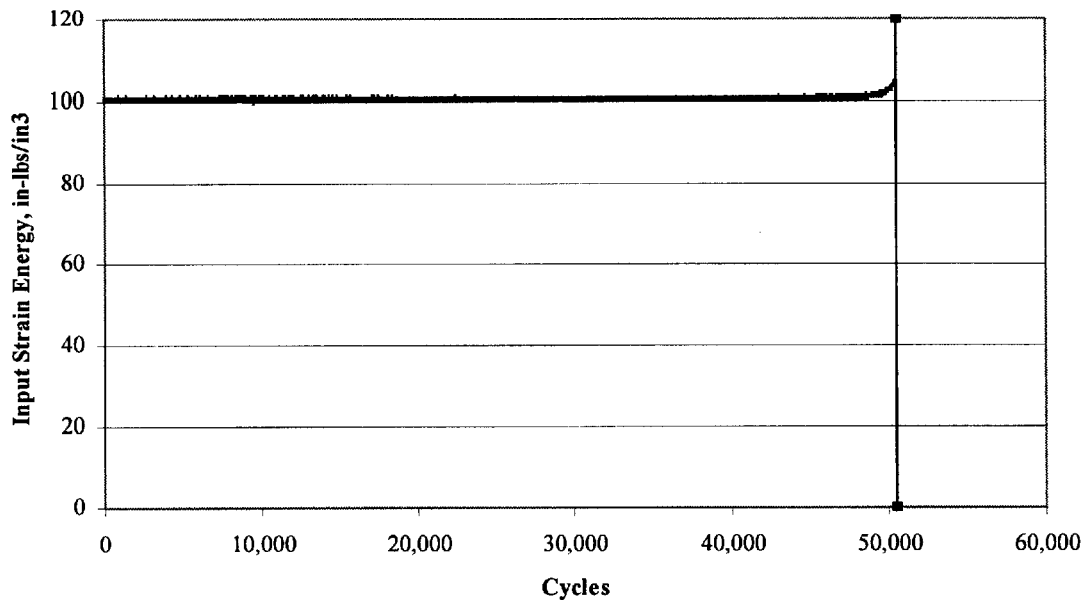
FIG. 91 shows the data curves for a tension-tension test of a corroded, unnotched aluminum coupon, the curves showing: (a) the input strain energy; (b) the hysteresis strain energy (HSE); (c) the slope of the HSE curve, with upper and lower control limit functions, and (d) the curvature of the HSE curve, with upper and lower control limit functions.
Figure 91B:
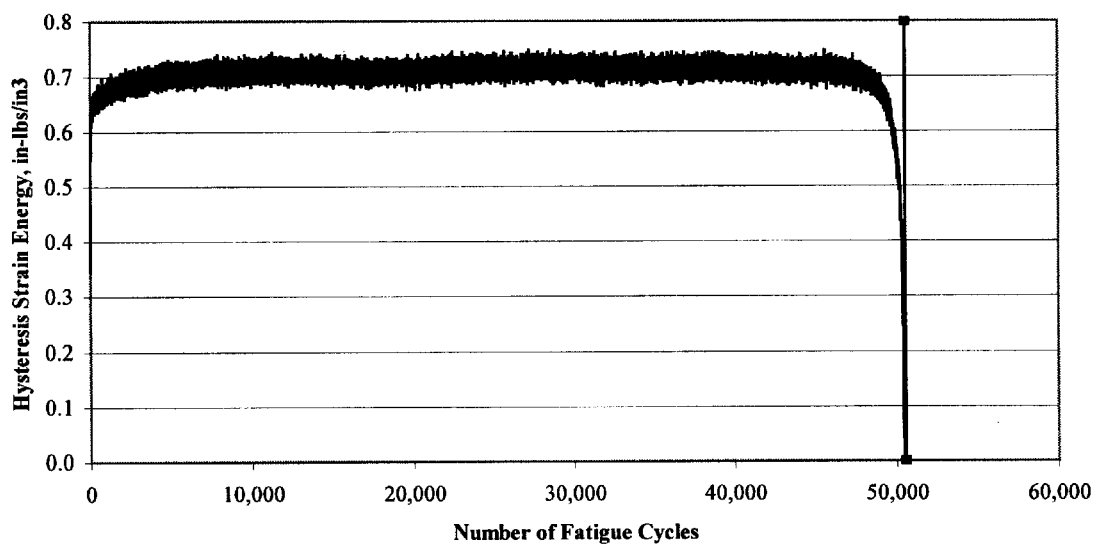
Figure 91C:
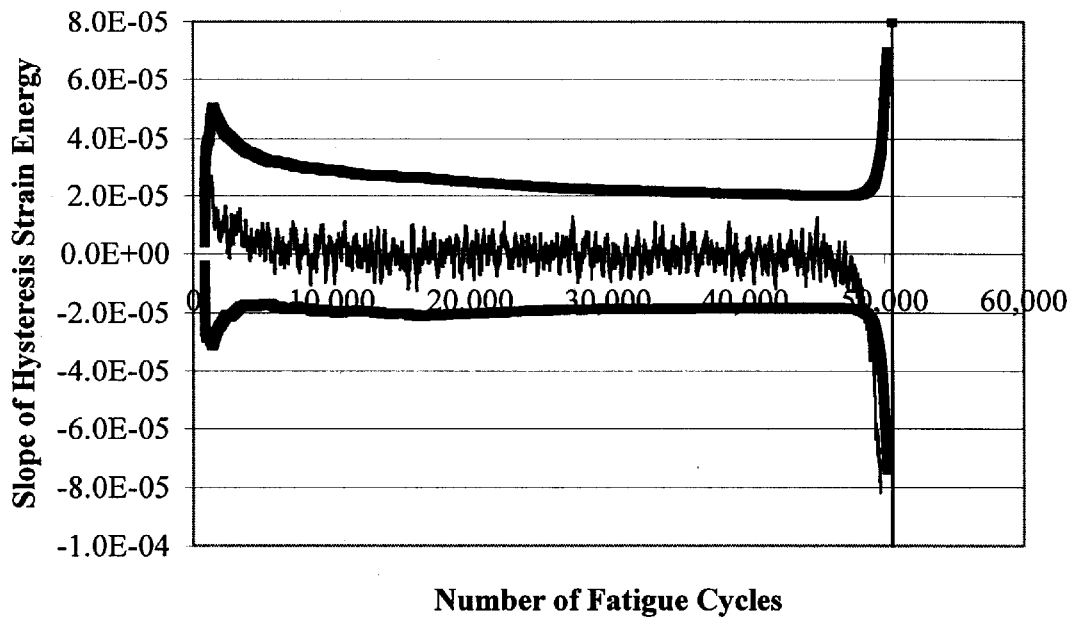
Figure 91D:
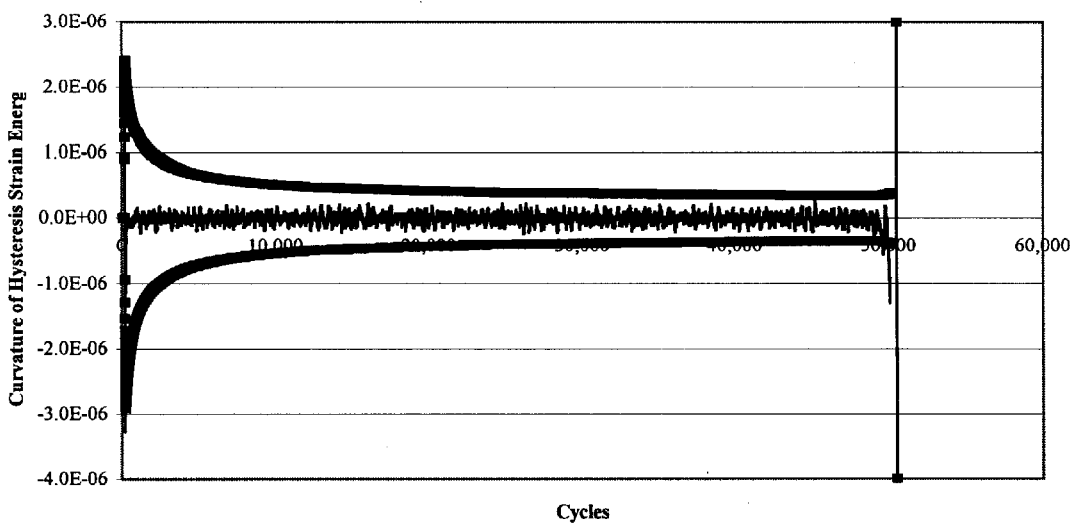

One test was conducted for an aluminum tension-tension coupon having the 0.180 inch hole to simulate MSD. The test coupon had been artificially corroded to simulate corrosion typically encountered in aircraft environmental exposure. The nominal stress test was 37,044 psi (gross section). FIGS. 89($a$–$d$) show the data graphically for: (a) the input strain energy (ISE); (b) HSE; (c) the slope of HSE, with upper and lower control limit functions; and (d) the curvature of HSE, with upper and lower control limit functions. The observed response showed a gradual increase in HSE to a level of about 0.09 in-lb/in$^3$, followed by a sharp drop. Even though this sample failed after only 1,008 cycles, the use of the slope and curvature functions with control limit functions provided a reliable indication of imminent failure.

An aluminum coupon was tension-tension tested in an uncorroded state, with a 0.18 by 0.010 inch horizontal notch cut into the gage portion by electric discharge machining. Stress was constant at 38,519 psi. FIG. 90 shows: (a) the ISE curve; (b) the HSE curve; (c) the slope of HSE, with upper and lower control limit functions; and (d) the curvature of HSE, with upper and lower control limit functions for this sample. In this sample, HSE reached a plateau of about 0.2 in-lb/in$^3$ for the early portion of fatigue life, and a rise started at about 70% of life. A sharp rise occurred during the final 10% of life. Using the convergence of the slope and/or curvature functions with a respective limit function, visible in FIG. 90($c$) and 90($d$), provided easy early recognition of the approach of final failure.

Another aluminum coupon, corroded but unnotched, was tension-tension tested at a constant stress of 52,000 psi. The ISE, HSE, slope, and curvature functions as described above are shown in FIGS. 91($a$–$d$), and the data are compared with the data from Example II as set forth in Table 6 in FIG. 92. These data show that the method is at least as effective for providing an indication of imminent failure in corroded materials as for uncorroded materials.

Figure 93A:
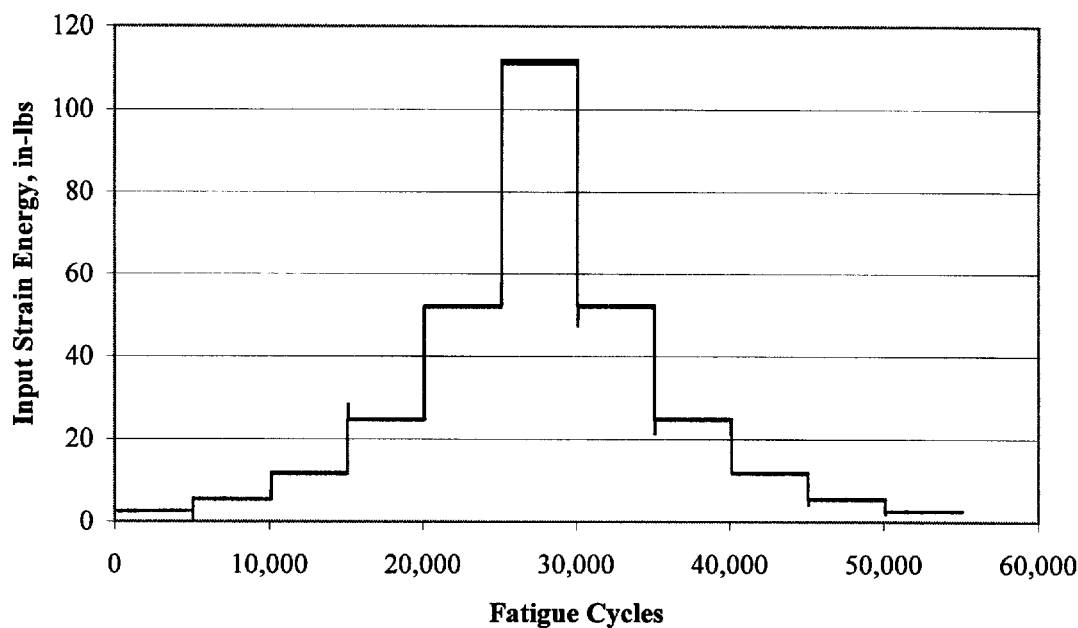
FIG. 93 shows plots of stair step fatigue amplitude for an uncorroded, unnotched aluminum coupon as described in Example IV below, the data showing (a) ISE and (b) HSE.
Figure 93B:
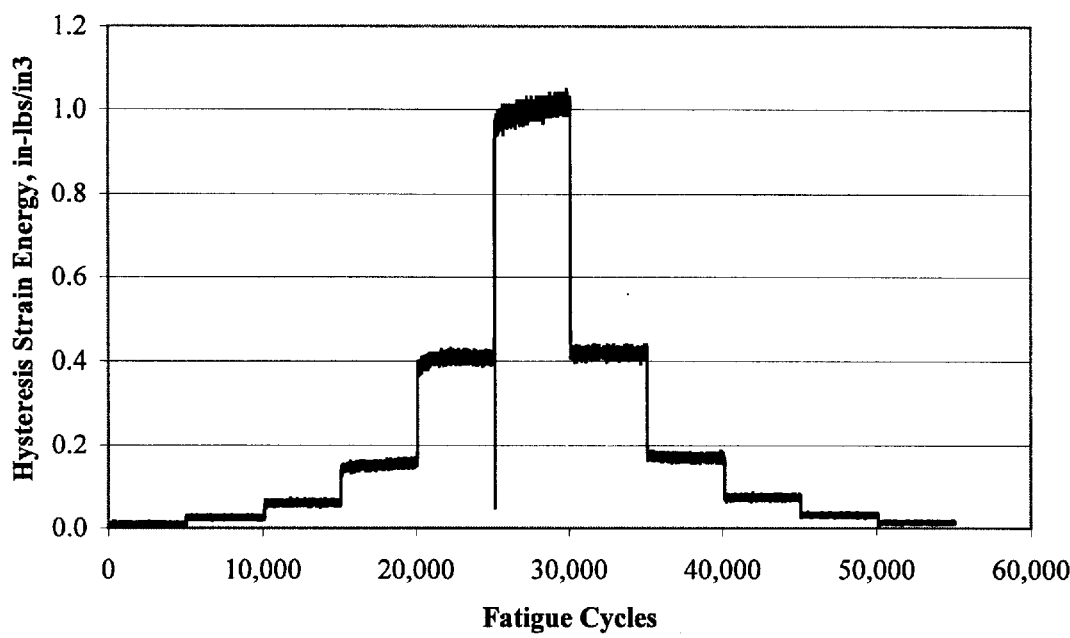
Figure 94A:
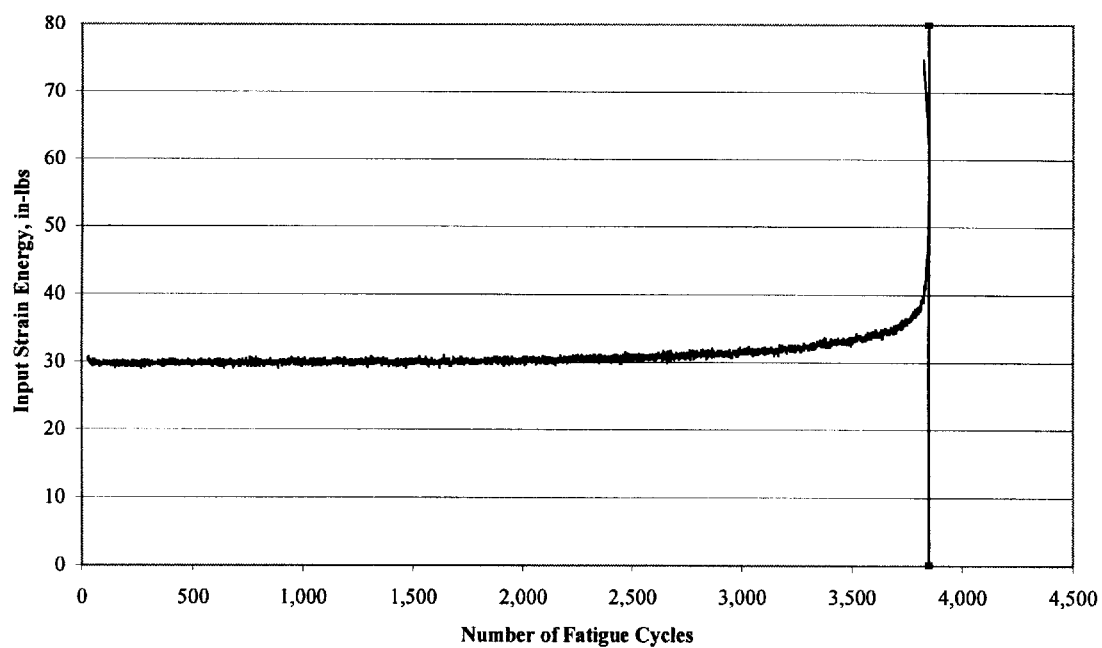
FIG. 94 shows the data curves for a tension-tension Mode I crack growth test of a tapered ASTM A-36 steel cylindrical, corroded and notched as described in Example IV, the curves showing: (a) the input strain energy; (b) the hysteresis strain energy (HSE); (c) the slope of the HSE curve, with upper and lower control limit functions, and (d) the curvature of the HSE curve, with upper and lower control limit functions.
Figure 94B:
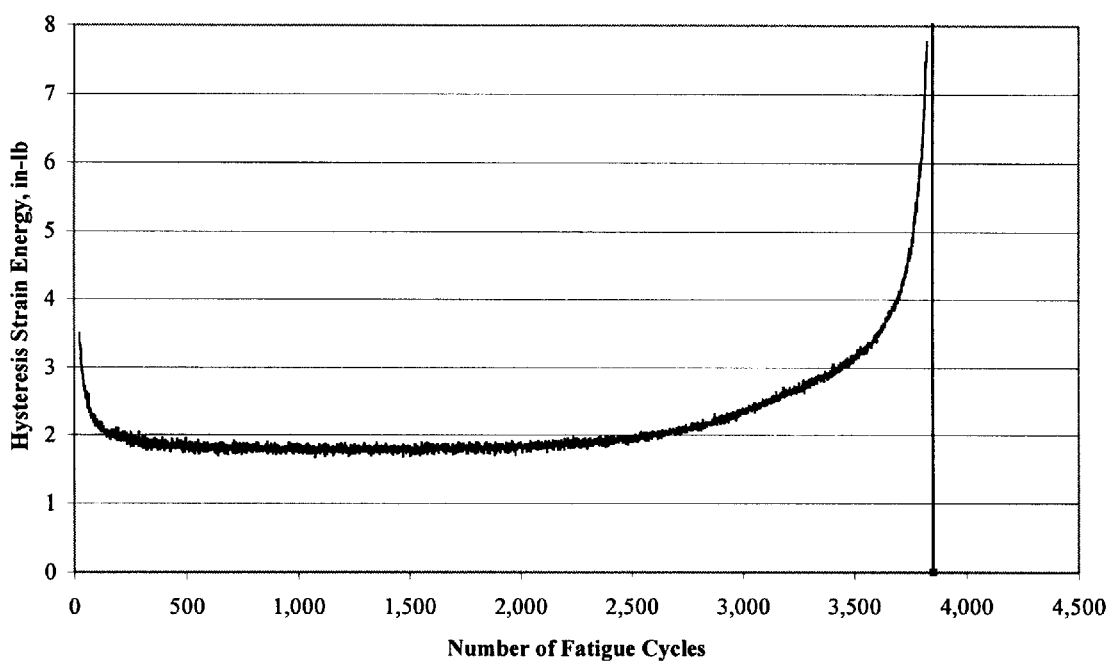
Figure 94C:
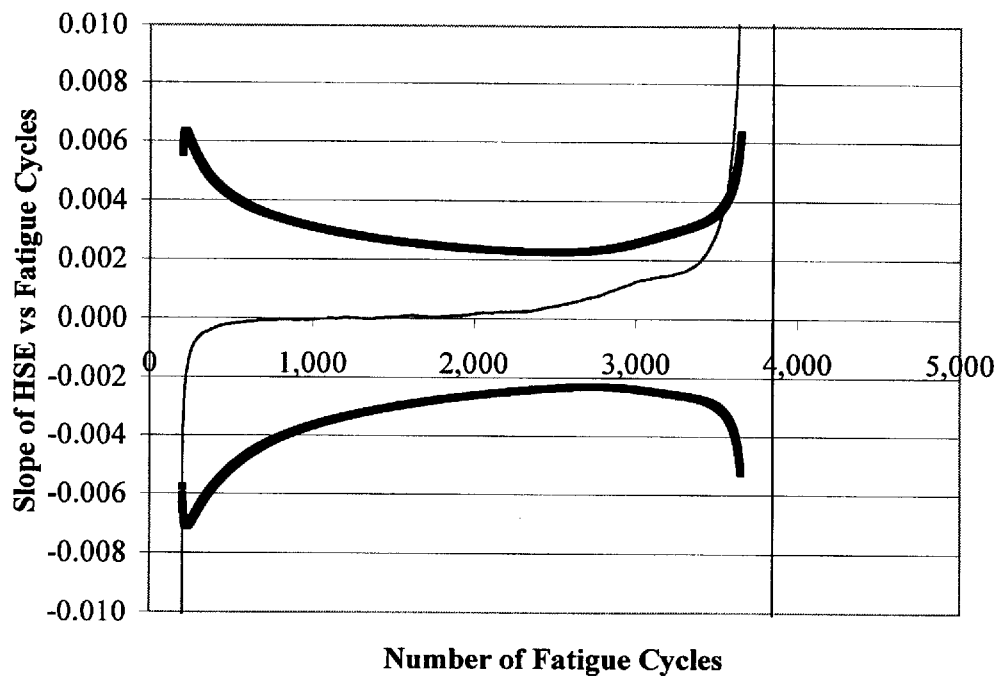
Figure 94D:
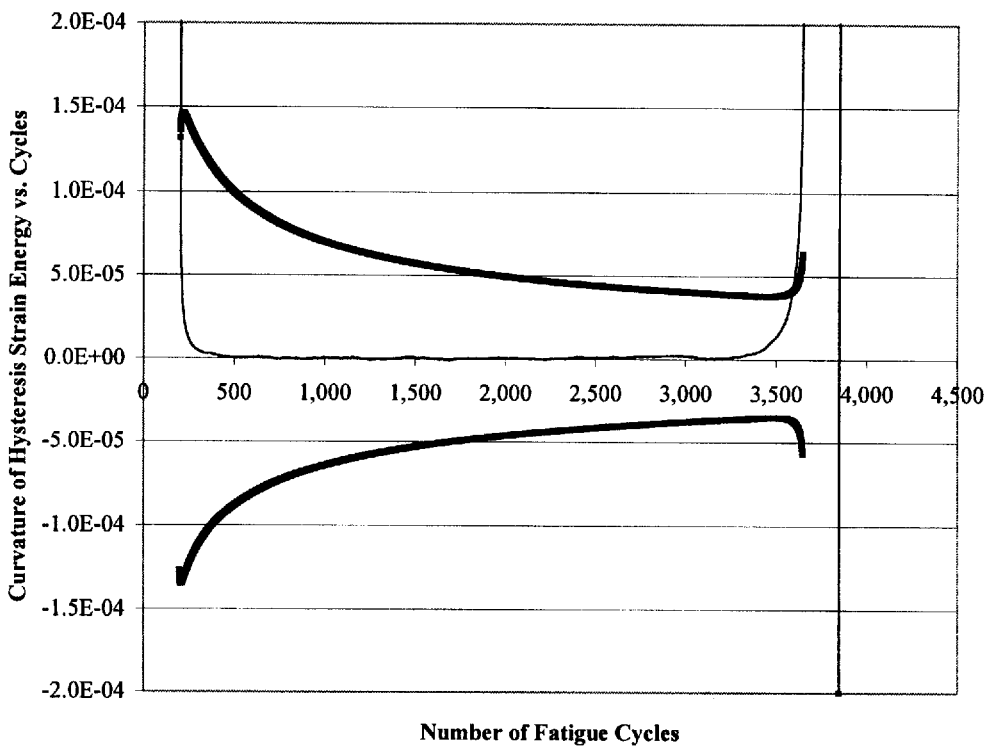

A test to record stair step fatigue amplitude was performed, using an unnotched, uncorroded aluminum coupon. The sample was subjected to a series of fatigue cycle stages of 5,000 cycles each, with the fatigue amplitude varying in equal logarithm of stress amplitude intervals between 8,000 psi and 52,000 psi. The ISE and HSE results of this test are shown, respectively, in FIGS. 93($a$) and 93($b$).

Another test was made of the method for a tension-tension Mode I crack growth test, this time using a tapered ASTM A-36 low carbon construction steel cylindrical coupon. The coupon was artificially corroded and a 0.165 inch deep circumferential notch was made. The specimen was tested with a maximum load amplitude of 42,222 lbs. and a minimum load amplitude of 4,222 lbs. at a loading frequency of about 0.1 Hz until failure at 3,850 cycles. The ISE, HSE, slope, and curvature functions as described above are shown in FIGS. 94($a$–$d$). This test confirmed the utility of the invention for use with this material.

EXAMPLE V

The series of tests in this example confirmed the utility of the invention in cases where stress corrosion or creep dominated as the primary cause of crack growth. The materials and apparatus used were as described above. The test coupons were unclad 2024-T3 aluminum coupons machined as described above.

To test low temperature creep, an uncorroded, notched coupon was loaded in tension to a nominal stress-intensity factor of 20.2 ksi√ in (nominal stress of 36,900 psi). The notch was 0.180 inches. The coupon was held at the nominal stress load for 1.063 hours, at which point the load was increased to 38,750 psi nominal stress and held there until failure at a total time of 169.383 hours. Periodically, to test corrosion effects, a 3.5% saline solution was dropped into the notched area. The data readings were static load and extensometer displacement, measured versus time. Initial input energy was calculated, and the changes to this integral over time were calculated as a function of time under load.

Figure 95:
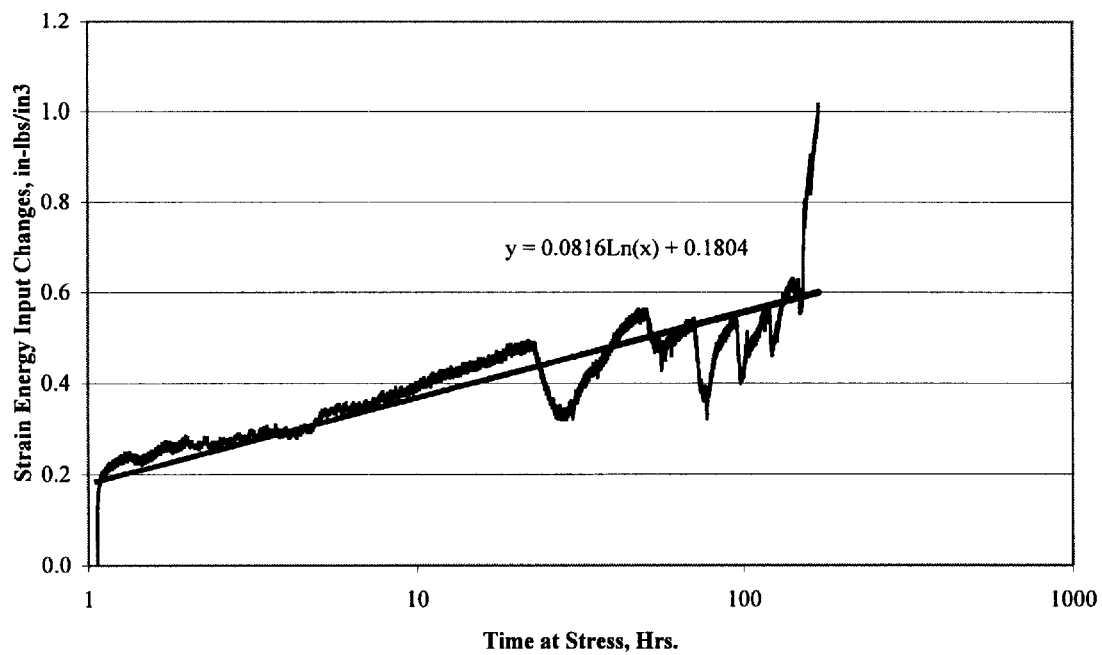
FIG. 95 is a plot of changes to stored strain energy versus logarithmic time under load, and the slope thereof, for a notched, uncorroded aluminum coupon as described in Example V, below.
Figure 96:
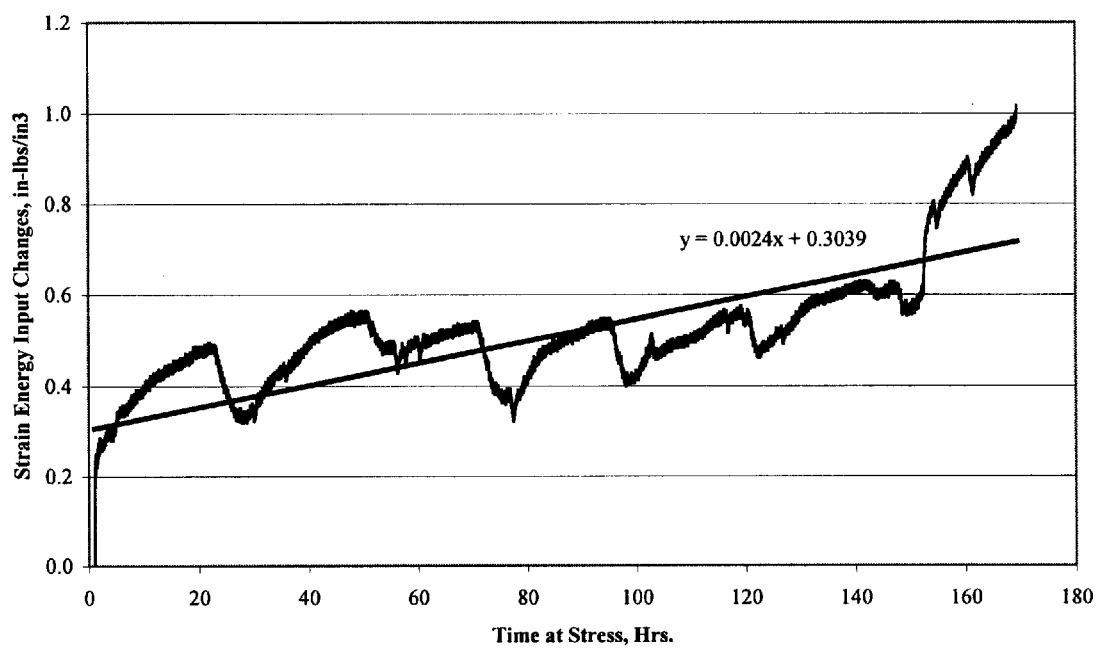
FIG. 96 is a plot of changes to stored strain energy versus linear time under load, and the slope thereof, for a notched uncorroded aluminum coupon as described in Example V, below.

This test effectively tested both creep processes and stress-corrosion processes. Changes to stored strain energy versus time under load, referred to herein as HSE for convenience (as noted above), and the slope of this HSE are shown in FIGS. 95 and 96. The plot in FIG. 95 is scaled to show logarithmic time, thus emphasizing the initial linear rate of change of energy versus logarithmic time characteristic of creep processes. FIG. 96 is plotted against linear time, showing the characteristics of stress-corrosion rate processes. The energy changes are cyclic in nature as a result of the periodic addition of the corrosion simulator, the 3.5% saline solution. Each peak and valley represents the interval represented by the addition of a new drop of solution in the crack tip, followed by the dissipation of the solution, followed by a new drop. The final rise in value is a reliable indicator of imminent failure due to stress corrosion, failure occurring immediately after these indicators.

Figure 97:
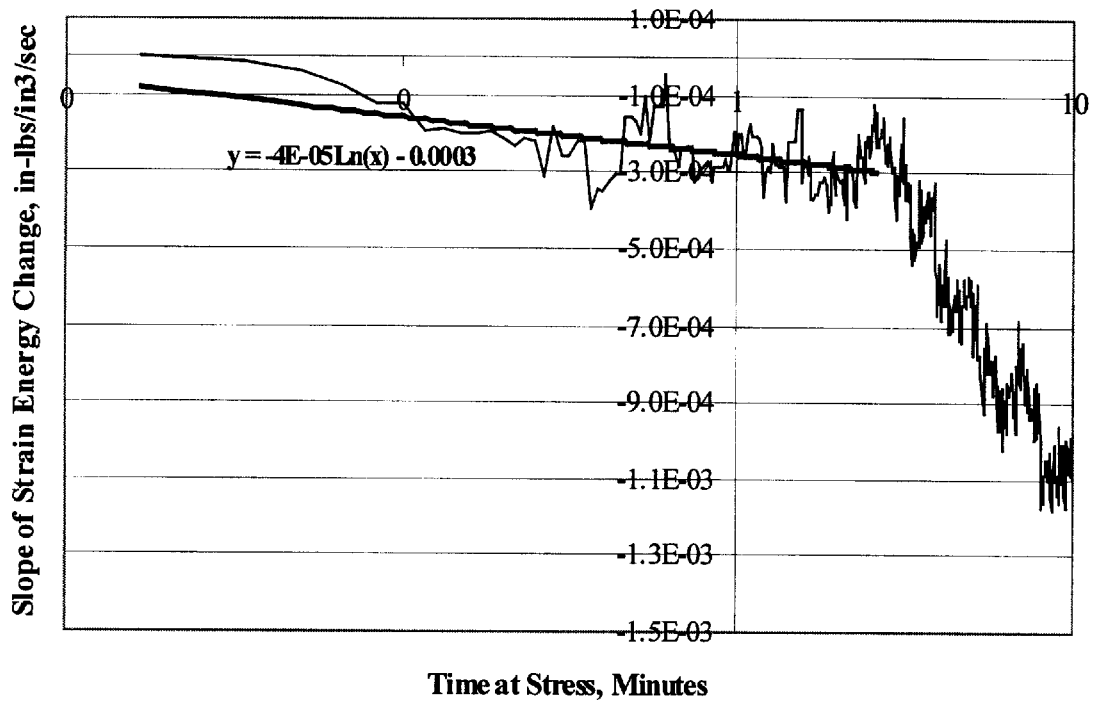
FIG. 97 is a plot of changes to stored strain energy versus logarithmic time for a notched corroded aluminum coupon as described in Example V, below.
Figure 98:
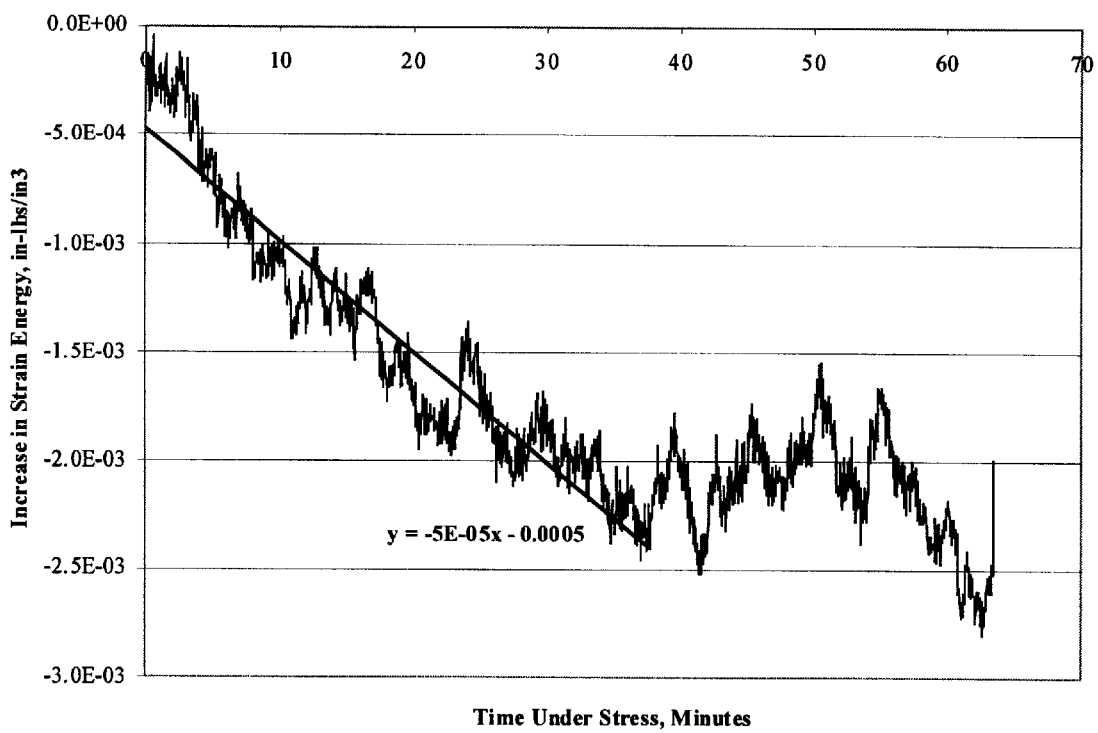
FIG. 98 is a plot of changes to stored strain energy versus linear time for a notched corroded aluminum coupon as described in Example V, below.
Figure 99:
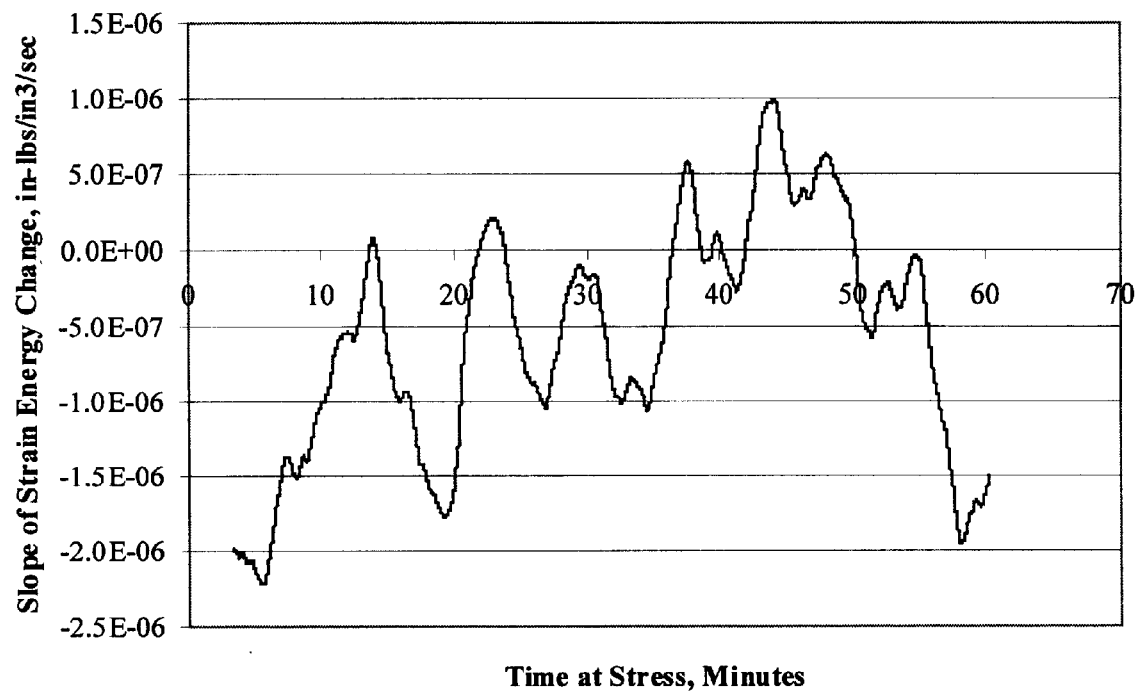
FIG. 99 is a plot of the slope of the curve shown in FIG. 98.
Figure 100:
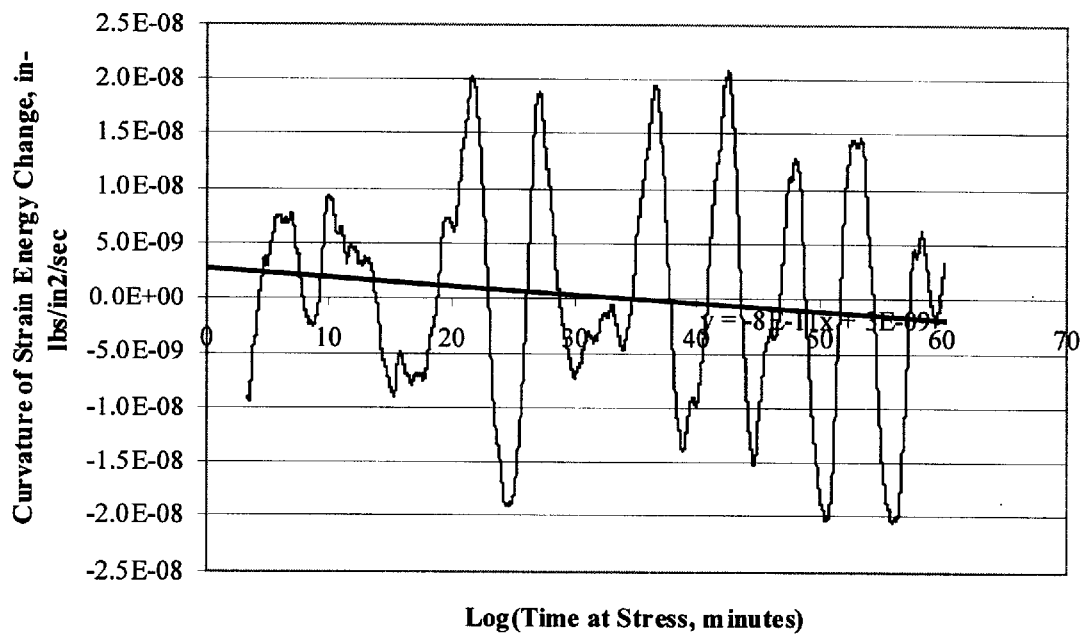
FIG. 100 is a plot of the curvature of the curve shown in FIG. 98.
Figure 101:
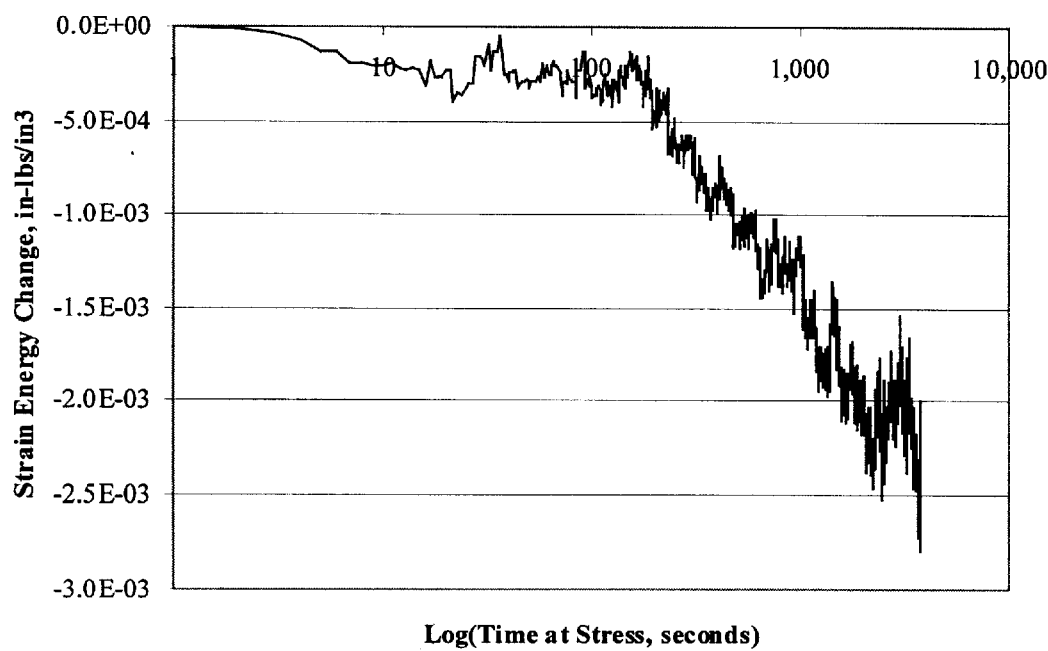
FIG. 101 is an expanded plot of the curve in FIG. 97, showing the entirety of the data set for the test described in Example V, below.

A similar test was conducted using a corroded, notched aluminum coupon with periodic addition of the saline solution. This specimen was held at a constant nominal stress of 42,000 psi, with failure occurring after 63.45 minutes. The results are plotted in FIGS. 97–101. FIG. 97 shows HSE (strain energy input change) as a function of logarithmic time, emphasizing creep characteristics. The curve initially, for about the first 100 seconds, follows that expected for creep processes, after which another process begins to dominate, the latter characteristic of stress corrosion. The peaks and valleys caused by the corrosive effect of the periodic addition of saline is noticeable. FIG. 98 plots the curve of HSE against linear time as a measure of stress corrosion. FIG. 99 is the plot of slope using linear time, the peaks and valleys being very visible. The sharp drop signalling impending end of life is clear in this plot. FIG. 100 is the plot of the curvature of the HSE curve. FIG. 101 shows the entirety of the HSE curve plotted against logarithmic time, again demonstrating the sharp drop near the end of life.

The test results from the Examples confirm the utility of the invention for use with the four main conditions affecting crack growth. Different steps for detecting the indicative end-stage trend in crack growth rate are set forth, and a wide variety of sensors are available for providing real-time data. The associated processors can be separate or integrated, and may consist of specially designed, dedicated circuits of preprogrammed general purpose processors. The output signal may activate a physical signal such as an audio alarm, or consist of graphic representations. There are thus numerous adaptations and variations that can be made without departing from the spirit and scope of the invention, which are set forth in the following claims

What is claimed is:

1. A method for the nonlinear detection of imminent failure in a structural element, the method comprising the steps:

sensing load- and strain- or load- and displacement-related data for said structural element;

generating a crack-growth rate function relating said data to an interval;

deriving from said crack-growth rate function at least one indicator function;

monitoring trends in said at least one indicator function;

and providing an indication when said monitoring detects an end-stage trend in said at least one indicator function.

2. The method according to claim 1, wherein said step of deriving comprises deriving a filtered function resulting from passing said crack-growth rate function through a nonlinear zero-phase filter means.

3. The method according to claim 2, wherein said at least one indicator function is a function selected from the group comprising the slope, the curvature, and both slope and curvature derived from said filtered function.

4. The method according to claim 1, wherein said monitoring comprises deriving from said indicator function at least one limit function and comparing said indicator function to said limit function to determine when said indicator function and said limit function converge.

5. The method according to claim 3, wherein said monitoring comprises deriving from said indicator function at least one limit function and comparing said indicator function to said limit function to determine when said indicator function and said limit function converge.

6. Apparatus for detecting an indication of imminent failure of a structural member, said apparatus comprising:

at least one sensor for sensing load- and strain- or load- and displacement-related data representative, respectively, of a load and strain or a load and displacement in a critical area to which said member is subject;

interval counting means for counting a desired interval and providing an interval count associated with said data;

first processor operatively connected to said sensor means and said interval counting means for providing a crack growth rate function relating data to said interval count;

second processor for deriving from said crack growth rate function at least one indicator function;

means for monitoring said at least one indicator function and detecting trends in said function;

and output means providing an indication when said monitoring means detects the onset of an end-stage trend in said at least one indicator function.

7. Apparatus according to claim 6, wherein said second processor comprises means for deriving a filtered function resulting from passing said crack-growth rate function through a nonlinear zero-phase filter means, and said filtered function is said indicator function.

8. Apparatus according to claim 6, wherein said second processor comprises means for deriving a filtered function resulting from passing said crack-growth rate function through a nonlinear zero-phase filter means and means for deriving from said filtered function a slope function, a curvature function, or both a slope and a curvature function, and wherein said indicator function is a function selected from the group consisting of said slope function, said curvature function, and both said slope and said curvature function.

9. Apparatus according to claim 6, wherein said means for monitoring comprises means for deriving from said indicator function at least one limit function and means for comparing said limit function and said indicator function, and means for detecting when said limit function and said indicator function converge.

10. Apparatus according to claim 6, wherein said first processor, said second processor, and said means for monitoring are incorporated in a single integrated processor.

11. Apparatus according to claim 6, wherein said sensor comprises optic fibers embedded in said structural member.

12. A method for indicating the approach of the end of useful life for a structural member subject to subcritical cracking, said method comprising:

sensing hysteresis strain energy data from said structural element;

deriving a hysteresis strain energy curve from said hysteresis strain energy data;

smoothing said hysteresis curve by passing said hysteresis strain energy curve through a nonlinear zero-phase filter means;

deriving at least one indicator function from said smoothed hysteresis strain energy curve, said indicator function selected from the group consisting of the slope of said smoothed hysteresis strain energy curve, the curvature of said smoothed hysteresis strain energy curve, and both the slope and curvature of said smoothed hysteresis strain energy curve;

monitoring trends in said at least one indicator function to detect the onset of an end-stage crack growth-rate trend; and providing an output indicative of the approach of the end of useful life for said element when said monitoring detects the onset of an end-stage crack growth-rate trend.

13. A method for indicating the approach of the end of useful life for a structural member subject to subcritical cracking, said method comprising:

sensing hysteresis strain energy data from said structural element;

deriving an hysteresis strain energy curve from said hysteresis strain energy data;

smoothing said hysteresis strain energy curve by passing said hysteresis strain energy curve through a nonlinear zero-phase filter means;

deriving at least one indicator function from said smoothed hysteresis strain energy curve, said indicator function selected from the group consisting of said smoothed hysteresis strain energy curve, the slope of said smoothed hysteresis strain energy curve, the curvature of said smoothed hysteresis strain energy curve, and both the slope and curvature of said smoothed hysteresis strain energy curve;

deriving from said indicator function at least one limit function;

comparing said indicator function with said limit function;

providing an output indicative of the approach of the end of useful life for said element when said indicator function and said limit function converge.

* * * * *